(12) United States Patent
Binggeli et al.

(10) Patent No.: US 7,348,349 B2
(45) Date of Patent: Mar. 25, 2008

(54) OXAZOLE DERIVATIVES

(75) Inventors: Alfred Binggeli, Binningen (CH); Markus Boehringer, Moehlin (CH); Uwe Grether, Loerrach (DE); Hans Hilpert, Muenchenstein (CH); Georges Hirth, Huningue (FR); Hans-Peter Maerki, Basel (CH); Markus Meyer, Neuenburg (DE); Peter Mohr, Basel (CH); Fabienne Ricklin, Hombourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 413 days.

(21) Appl. No.: 11/183,360

(22) Filed: Jul. 18, 2005

(65) Prior Publication Data

US 2005/0267180 A1   Dec. 1, 2005

Related U.S. Application Data

(62) Division of application No. 10/679,604, filed on Oct. 6, 2003, now Pat. No. 6,969,725.

(30) Foreign Application Priority Data

Oct. 7, 2002   (EP)   ................... 02022286

(51) Int. Cl.
*A61K 31/421* (2006.01)
*C07D 263/30* (2006.01)

(52) U.S. Cl. .................. 514/374; 548/235; 548/236

(58) Field of Classification Search .............. 548/235, 548/236; 514/374
See application file for complete search history.

(56) References Cited

U.S. PATENT DOCUMENTS

| | | | |
|---|---|---|---|
| 6,248,897 B1 | 6/2001 | Ando et al. | |
| 6,251,926 B1 | 6/2001 | Momose et al. | |
| 6,498,174 B1 | 12/2002 | Collins et al. | |
| 6,642,389 B2 | 11/2003 | Binggeli et al. | |
| 6,969,725 B2 * | 11/2005 | Binggeli et al. | ............. 514/374 |

FOREIGN PATENT DOCUMENTS

| | | |
|---|---|---|
| WO | WO 91/19702 | 12/1991 |
| WO | WO 00 08002 | 2/2000 |
| WO | WO 01/21602 | 3/2001 |
| WO | WO 02 16331 | 2/2002 |
| WO | WO 02 92084 | 11/2002 |

OTHER PUBLICATIONS

Keller et al., Trends Endocrin. Metab., 4, pp. 291-296 (1993).
McDougald et al., Current Biology, 5, pp. 618-621 (1995).
Guerre-Millo et al., J. Biol. Chem., 275, pp. 16638-16642 (2000).
Haigh et al., Tetrahedron: Asymmetry 10, pp. 1353-1367 (1999).
Einsiedel et al., Bioorg. Med. Chem. Lett., 10, pp. 2041-2044 (2000).
Nichols et al., Anal. Biochem., 257, pp. 112-119 (1998).
Balfour et al., Drugs, 57, pp. 921-930 (1999).

* cited by examiner

*Primary Examiner*—Golam M. M. Shameem
(74) *Attorney, Agent, or Firm*—George W. Johnston; Dennis P. Tramaloni; Brian C. Remy

(57) ABSTRACT

The present invention relates to compounds of formula (I)

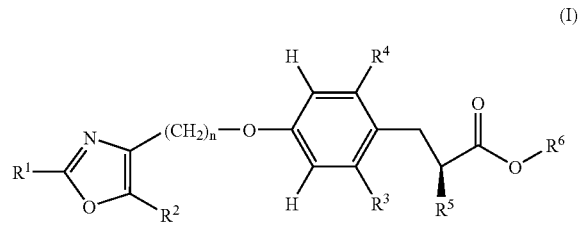

wherein wherein $R^1$, $R^2$, $R^3$, $R^4$, $R^5$, $R^6$ and n are as described herein. The compounds of the present invention can be used as medicaments for the treatment and/or prevention of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases (such as e.g. crown disease, inflammatory bowel disease, collitis, pancreatitis, cholestasis/fibrosis of the liver, and diseases that have an inflammatory component such as e.g. Alzheimer's disease or impaired/improvable cognitive function) and proliferative diseases.

30 Claims, No Drawings

OXAZOLE DERIVATIVES

PRIORITY TO RELATED APPLICATIONS

This application is a division of prior application Ser. No. 10/679,604, filed Oct. 6, 2003, now U.S. Pat. No. 6,969,725 which claims the benefit of European Application No. 02022286.5, filed Oct. 7, 2002; each of which is hereby incorporated by reference in its entirety.

BACKGROUND OF THE INVENTION

The present invention is concerned with novel oxazole derivatives, their manufacture and their use as medicaments.

Peroxisome Proliferator Activated Receptors (PPAR's) are members of the nuclear hormone receptor super family, which are ligand-activated transcription factors regulating gene expression. Various subtypes thereof have been identified and cloned. These include PPARα, PPARβ (also known as PPARδ), and PPARγ. There exist at least two major isoforms of PPARγ. While PPARγ1 is ubiquitously expressed in most tissues, the longer isoform PPARγ2 is almost exclusively found in adipocytes. In contrast, PPARα is predominantly expressed in the liver, kidney and heart. PPAR's modulate a variety of body responses including glucose- and lipid-homeostasis, cell differentiation, inflammatory responses and cardiovascular events.

Diabetes is a disease in which a patient's ability to control glucose levels in blood is impaired, because he has partially lost the ability to respond properly to the action of insulin. In type II diabetes (T2D), often referred to as non-insulin dependent diabetes mellitus (NIDDM), which afflicts 80-90% of all diabetic patients in developed countries, the Isles of Langerhans in the pancreas still produce insulin. However, the target organs, mainly muscle, liver and adipose tissue, exhibit a profound resistance to insulin stimulation, and the body compensates by producing unphysiologically high levels of insulin. In later stage of disease, however, insulin secretion decreases due to exhaustion of the pancreas. In addition to that T2D is a metabolic-cardiovascular disease syndrome.

Among the comorbidities associated with T2D are for example insulin resistance, dyslipidemia, hypertension, endothelial dysfunction and inflammatory atherosclerosis. Current first line treatment for diabetes generally involves low fat—and glucose—diet and exercise. However, compliance can be moderate and as the disease progresses, treatment with hypoglycemic drugs, e.g. sulfonylureas or metformin, becomes necessary. A promising new class of drugs has recently been introduced that resensitizes patients to their own insulin (insulin sensitizers), thereby reverting blood glucose and triglyceride levels to normal, and thus abolishing, or at least reducing, the requirement for exogenous insulin. Pioglitazone (Actos™) and rosiglitazone (Avandia™) belong to the thiazolidinediones (TZD) class of PPARγ-agonists and were the first representatives who had been approved for NIDDM in several countries. These compounds, however, suffer from side effects including rare but severe liver toxicity (as seen with troglitazone), and they increase body weight in humans. Therefore, new, better and more efficacious drugs for the treatment of NIDDM are urgently needed. Recent studies provide evidence that a coagonism on PPARα and PPARγ would result in compounds with enhanced therapeutic potential, i.e. such compounds should improve the lipid profile in addition to the normalization of glucose- and insulin-levels (Keller and Wahli: Trends Endocrin. Metab. 1993; 4:291-296, Macdonald and Lane: Current Biology Vol. 5 pp. 618-621 (1995)). Recent observations suggest furthermore that there is an independent PPARα mediated effect on insulin-sensitization that could result secondary to the reduction in lipids (Guerre-Millo et al; J Biol Chem 2000; 275: 16638-16642). Consequently, the incorporation of PPARα activity into PPARγ agonists is expected to give rise to more efficacious drugs for the treatment and/or prevention of diabetes.

SUMMARY OF THE INVENTION

The present invention relates to compounds of the formula (I)

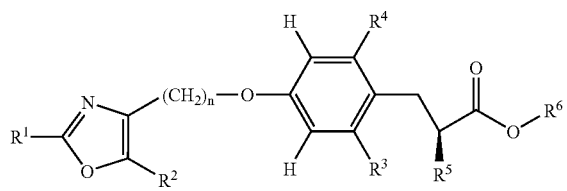

(I)

wherein $R^1$, $R^2$, $R^3$, $R^4$, $R^5$, $R^6$ and n are as described herein, or pharmaceutically acceptable salts and/or pharmaceutically acceptable esters thereof.

The novel compounds of the present invention exceed the compounds known in the art, inasmuch as they bind to and activate both, PPARα and PPARγ, simultaneously and very efficiently. Therefore, these compounds combine the antiglycemic effect of PPARγ activation with the anti-dyslipidemic effect of PPARα activation. Consequently, plasma glucose and insulin are reduced (=insulin sensitization), triglycerides lowered and HDL cholesterol increased (=improved lipid profile). In addition, such compounds may also lower LDL cholesterol, decrease blood pressure and counteract inflammatory atherosclerosis. Since multiple facets of the T2D disease syndrome are addressed by PPARα and γ coagonists, they are expected to have an enhanced therapeutic potential compared to the compounds already known in the art.

The compounds of the present invention further exhibit improved pharmacological properties compared to known compounds.

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine.

The term "protecting group" refers to groups such as e.g. acyl, alkoxycarbonyl, aryloxycarbonyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "fluoro-lower-alkyl" refers to lower-alkyl groups which are mono- or multiply substituted with fluorine. Examples of fluoro-lower-alkyl groups are e.g. $CF_3$, $CF_3CH_2$ and $(CF_3)_2CH$.

The term "alkoxy" refers to the group R'—O—, wherein R' is alkyl. The term "lower-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy.

The term "fluoro-lower-alkoxy" refers to the group R"—O—, wherein R" is fluoro-lower-alkyl. Examples of fluoro-lower-alkoxy groups are e.g. $CF_3$—O, $CF_3CH_2$—O and $(CF_3)_2CH$—O.

The term "lower-alkenyl", alone or in combination signifies a straight-chain or branched hydrocarbon residue comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower-alkenyloxy" means a group R"—O—, wherein R" is lower-alkenyl. Examples of lower-alkenyloxy groups are butenyloxy, particularly but-3-enyloxy.

The term "fluoro-lower-alkenyloxy" refers to lower-alkenyloxy groups as defined above, which are mono- or multiply substituted with fluorine. Examples of fluoro-lower-alkenyloxy groups are e.g. (Z) or (E) 4,4,4-trifluoro-but-2-en-1-yl.

The term "aryl" relates to the phenyl or naphthyl group, preferably the phenyl group, which can optionally be mono- or multiply-substituted, particularly mono-, di- or tri-substituted by halogen, hydroxy, CN, $CF_3$, $NO_2$, $NH_2$, N(H, lower-alkyl), $N(lower-alkyl)_2$, carboxy, aminocarbonyl, lower-alkyl, fluoro-lower-alkyl, lower-alkoxy, phenyl and/or phenyloxy. Preferred substituents are halogen, lower-alkyl, fluoro-lower-alkyl and/or lower-alkoxy.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can comprise 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are e.g. thienyl and furyl which can optionally be substituted as described above, preferably with halogen, $CF_3$, lower-alkyl and/or lower-alkoxy.

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

DETAILED DESCRIPTION OF THE INVENTION

In detail, the present invention relates to compounds of formula (I)

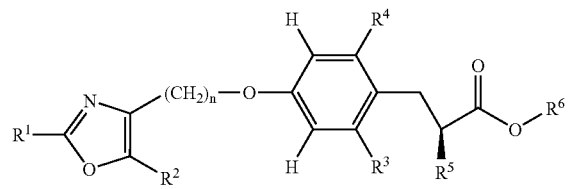

(I)

wherein
$R^1$ is aryl or heteroaryl;
$R^2$ is hydrogen, lower-alkyl, or fluoro-lower-alkyl;
$R^3$ and $R^4$ independently from each other are hydrogen, hydroxy, halogen, lower-alkyl, fluoro-lower-alkyl, hydroxy-lower-alkyl, lower-alkoxy-lower-alkyl, lower-alkoxy, fluoro-lower-alkoxy, hydroxy-lower-alkoxy, lower-alkoxy-lower-alkoxy, or lower-alkenyl,
wherein at least one of $R^3$ and $R^4$ is not hydrogen;
$R^5$ is lower-alkoxy, fluoro-lower-alkoxy, lower-alkenyloxy, fluoro-lower-alkenyloxy, aryloxy, aryl-lower-alkoxy, or aryl-fluoro-lower-alkoxy;
$R^6$ is hydrogen or lower-alkyl;
n is 1, 2 or 3;
or pharmaceutically acceptable salts and/or pharmaceutically acceptable esters thereof.

Preferred are the compounds of formula (I)

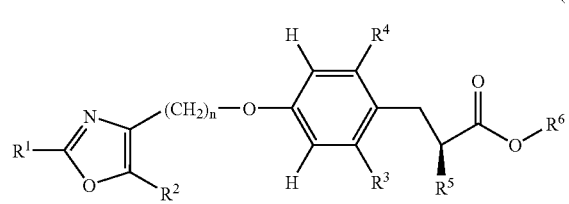

(I)

wherein
$R^1$ is aryl or heteroaryl;
$R^2$ is hydrogen, lower-alkyl, or fluoro-lower-alkyl;
$R^3$ and $R^4$ independently from each other are hydrogen, hydroxy, halogen, lower-alkyl, fluoro-lower-alkyl, hydroxy-lower-alkyl, lower-alkoxy-lower-alkyl, lower-alkoxy, fluoro-lower-alkoxy, hydroxy-lower-alkoxy, lower-alkoxy-lower-alkoxy, or lower-alkenyl,
wherein at least one of $R^3$ and $R^4$ is not hydrogen;
$R^5$ is lower-alkoxy, fluoro-lower-alkoxy, lower-alkenyloxy, fluoro-lower-alkenyloxy, aryloxy, aryl-lower-alkoxy, or aryl-fluoro-lower-alkoxy;
$R^6$ is hydrogen or lower-alkyl;
n is 1;

or pharmaceutically acceptable salts and/or pharmaceutically acceptable esters thereof.

The compounds of formula (I) as described above comprise an asymmetric carbon which is adjacent to $R^5$. The carbon atom to which $R^5$ is attached is of the S configuration according to the Cahn-Ingold-Prelog-Convention.

Compounds of formula (I) as defined above, wherein $R^1$ is aryl are preferred.

Compounds, wherein $R^1$ is phenyl optionally substituted with 1 to 3 substituents independently selected from the group consisting of lower-alkyl, lower-alkoxy, halogen, and fluoro-lower-alkyl are also preferred, with those compounds wherein $R^1$ is phenyl optionally substituted with 1 to 2 substituents independently selected from the group consisting of lower-alkyl, lower-alkoxy, and halogen being more preferred, and with those compounds wherein $R^1$ is phenyl, 2-methyl-phenyl, 4-isopropoxy-phenyl, 4-fluoro-3-methyl-phenyl, 2-fluoro-phenyl, 4-isopropyl-phenyl, 2-ethoxy-4-fluoro-phenyl, 3-methoxy-phenyl, or 4-tert-butyl-phenyl being particularly preferred. Compounds, in which $R^1$ is phenyl substituted with methyl and/or fluorine are preferred, particularly 2-methyl-phenyl or 2-fluoro-phenyl.

Furthermore, compounds as defined above in which $R^2$ is hydrogen or lower-alkyl are preferred, with hydrogen or methyl being particularly preferred. Hydrogen and methyl individually constitute separate preferred embodiments. Compounds in which $R^2$ is lower alkyl, preferably methyl, are also preferred.

Compounds of formula (I), wherein $R^3$ and $R^4$ independently from each other are hydrogen, hydroxy, halogen, lower-alkyl, fluoro-lower-alkyl, or lower-alkoxy, wherein at least one of $R^3$ and $R^4$ is not hydrogen also relate to a preferred embodiment of the present invention. Compounds, wherein $R^3$ is hydrogen or methyl are preferred. Hydrogen and methyl individually relate to preferred embodiments of the present invention. Compounds as defined above, wherein $R^4$ is methyl, ethyl, fluoro, chloro, trifluoromethyl, hydroxy, methoxy, ethoxy, or isopropoxy are particularly preferred. Preferably, $R^3$ is hydrogen and $R^4$ is lower-alkyl, particularly methyl.

Another preferred embodiment of the present invention relates to compounds of formula (I) as defined above, wherein $R^5$ is lower-alkoxy, more preferably methoxy or ethoxy, more preferably ethoxy. Other preferred compounds are those, wherein $R^6$ is hydrogen.

Preferred compounds are those, wherein $R^1$ is phenyl substituted with methyl and/or fluorine, $R^2$ is lower-alkyl, $R^3$ is hydrogen, $R^4$ is lower-alkyl, $R^5$ is lower-alkoxy, and $R^6$ is hydrogen. More preferred compounds are those, wherein $R^1$ is 2-methyl-phenyl or 2-fluoro-phenyl, $R^2$ is methyl, $R^3$ is hydrogen, $R^4$ is methyl, $R^5$ is ethoxy, and $R^6$ is hydrogen.

Compounds of formula (I), wherein n is 1, 2 or 3, individually relate to preferred embodiments of the present invention.

The pharmaceutically acceptable salts of the compound of formula (I) and the pharmaceutically acceptable esters of the compounds of formula (I) individually constitute preferred embodiments of the present invention. Particularly preferred are compounds of formula (I).

Preferred compounds of general formula (I) are those selected from the group consisting of (S)-2-Ethoxy-3-[2-methyl-4-(5-methyl-2-o-tolyl-oxazol-4-ylmethoxy)-phenyl]-propionic acid,
(S)-2-Ethoxy-3-{4-[2-(4-isopropoxy-phenyl)-5-methyl-oxazol-4-ylmethoxy]-2-methyl-phenyl}-propionic acid,
(S)-2-Ethoxy-3-[2-methyl-4-(5-methyl-2-phenyl-oxazol-4-ylmethoxy)-phenyl]-propionic acid,
(S)-3-{4-[2-(3,5-Dimethoxy-phenyl)-5-methyl-oxazol-4-ylmethoxy]-2-methyl-phenyl}-2-ethoxy-propionic acid,
(S)-2-Ethoxy-3-{4-[2-(4-fluoro-3-methyl-phenyl)-5-methyl-oxazol-4-ylmethoxy]-2-methyl-phenyl}-propionic acid,
(S)-2-Ethoxy-3-{4-[2-(2-fluoro-phenyl)-5-methyl-oxazol-4-ylmethoxy]-2-methyl-phenyl}-propionic acid,
(S)-3-(4-{2-[2-(4-Chloro-phenyl)-5-methyl-oxazol-4-yl]-ethoxy}-2-methyl-phenyl)-2-ethoxy-propionic acid,
(S)-2-Ethoxy-3-[2-ethyl-4-(5-methyl-2-phenyl-oxazol-4-ylmethoxy)-phenyl]-propionic acid,
(S)-2-Ethoxy-3-{2-ethyl-4-[2-(4-fluoro-3-methyl-phenyl)-5-methyl-oxazol-4-ylmethoxy]-phenyl}-propionic acid,
(S)-2-Ethoxy-3-{2-ethyl-4-[2-(2-fluoro-phenyl)-5-methyl-oxazol-4-ylmethoxy]-phenyl}-propionic acid,
(S)-2-Ethoxy-3-[2-ethyl-4-(5-methyl-2-o-tolyl-oxazol-4-ylmethoxy)-phenyl]-propionic acid,
(S)-2-Ethoxy-3-{2-ethyl-4-[2-(4-isopropoxy-phenyl)-5-methyl-oxazol-4-ylmethoxy]-phenyl}-propionic acid,
(S)-2-Ethoxy-3-[2-fluoro-4-(5-methyl-2-phenyl-oxazol-4-ylmethoxy)-phenyl]-propionic acid,
(S)-2-Ethoxy-3-{2-fluoro-4-[2-(2-fluoro-phenyl)-5-methyl-oxazol-4-ylmethoxy]-phenyl}-propionic acid,
(S)-3-[2-Chloro-4-(5-methyl-2-phenyl-oxazol-4-ylmethoxy)-phenyl]-2-ethoxy-propionic acid,
(S)-3-{2-Chloro-4-[2-(4-fluoro-3-methyl-phenyl)-5-methyl-oxazol-4-ylmethoxy]-phenyl}-2-ethoxy-propionic acid,
(S)-3-{2-Chloro-4-[2-(4-isopropoxy-phenyl)-5-methyl-oxazol-4-ylmethoxy]-phenyl}-2-ethoxy-propionic acid,
(S)-3-{2-Chloro-4-[2-(2-fluoro-phenyl)-5-methyl-oxazol-4-ylmethoxy]-phenyl}-2-ethoxy-propionic acid,
(S)-3-[2-Chloro-4-(5-methyl-2-o-tolyl-oxazol-4-ylmethoxy)-phenyl]-2-ethoxy-propionic acid,
(S)-3-{2-Chloro-4-[2-(2-methoxy-phenyl)-5-methyl-oxazol-4-ylmethoxy]-phenyl}-2-ethoxy-propionic acid,
(S)-2-Ethoxy-3-[4-(5-methyl-2-phenyl-oxazol-4-ylmethoxy)-2-trifluoromethyl-phenyl]-propionic acid,
(S)-2-Ethoxy-3-{4-[2-(2-fluoro-phenyl)-5-methyl-oxazol-4-ylmethoxy]-2-trifluoromethyl-phenyl}-propionic acid,
(S)-3-{2-Hydroxy-4-[2-(5-methyl-2-phenyl-oxazol-4-yl)-ethoxy]-phenyl}-2-methoxy-propionic acid,
(S)-2-Ethoxy-3-[2-methoxy-4-(5-methyl-2-phenyl-oxazol-4-ylmethoxy)-phenyl]-propionic acid,
(S)-2-Ethoxy-3-{4-[2-(4-isopropyl-phenyl)-5-methyl-oxazol-4-ylmethoxy]-2-methoxy-phenyl}-propionic acid,
(S)-2-Ethoxy-3-{4-[2-(4-fluoro-3-methyl-phenyl)-5-methyl-oxazol-4-ylmethoxy]-2-methoxy-phenyl}-propionic acid,
(S)-2-Ethoxy-3-{4-[2-(4-isopropoxy-phenyl)-5-methyl-oxazol-4-ylmethoxy]-2-methoxy-phenyl}-propionic acid,
(S)-3-{4-[2-(3-Chloro-phenyl)-5-methyl-oxazol-4-ylmethoxy]-2-methoxy-phenyl}-2-ethoxy-propionic acid,
(S)-3-[2,6-Dimethyl-4-(5-methyl-2-phenyl-oxazol-4-ylmethoxy)-phenyl]-2-ethoxy-propionic acid,
(S)-2-Ethoxy-3-{4-[2-(4-isopropoxy-phenyl)-5-methyl-oxazol-4-ylmethoxy]-2,6-dimethyl-phenyl}-propionic acid,
(S)-2-Ethoxy-3-{4-[2-(4-isopropyl-phenyl)-5-methyl-oxazol-4-ylmethoxy]-2,6-dimethyl-phenyl}-propionic acid,
(S)-3-{4-[2-(3-Chloro-phenyl)-5-methyl-oxazol-4-ylmethoxy]-2,6-dimethyl-phenyl}-2-ethoxy-propionic acid,
(S)-2-Ethoxy-3-{4-[2-(4-fluoro-3-methyl-phenyl)-5-methyl-oxazol-4-ylmethoxy]-2,6-dimethyl-phenyl}-propionic acid,
(S)-3-{4-[2-(3,5-Dichloro-phenyl)-5-methyl-oxazol-4-ylmethoxy]-2-methyl-phenyl}-2-ethoxy-propionic acid,
(S)-3-{4-[2-(3,5-Dimethyl-phenyl)-5-methyl-oxazol-4-ylmethoxy]-2-methyl-phenyl}-2-ethoxy-propionic acid,
(S)-2-Ethoxy-3-{2-methyl-4-[5-methyl-2-(2-trifluoromethyl-phenyl)-oxazol-4-ylmethoxy]-phenyl}-propionic acid, (S)-2-Ethoxy-3-{2-methyl-4-[5-methyl-2-(3-trifluoromethyl-phenyl)-oxazol-4-ylmethoxy]-phenyl}-propionic acid,
(S)-2-Ethoxy-3-{4-[2-(4-fluoro-phenyl)-5-methyl-oxazol-4-ylmethoxy]-2-methyl-phenyl}-propionic acid,
(S)-2-Ethoxy-3-{2-methyl-4-[5-methyl-2-(4-trifluoromethyl-phenyl)-oxazol-4-ylmethoxy]-phenyl}-propionic acid,
(S)-2-Ethoxy-3-{4-[2-(4-isopropyl-phenyl)-5-methyl-oxazol-4-ylmethoxy]-2-methyl-phenyl}-propionic acid,
(S)-2-Ethoxy-3-{2-methyl-4-[5-methyl-2-(3,4,5-trimethoxy-phenyl)-oxazol-4-ylmethoxy]-phenyl}-propionic acid,
(S)-2-Ethoxy-3-(4-{2-[2-(2-ethoxy-4-fluoro-phenyl)-5-methyl-oxazol-4-yl]-ethoxy}-2-methyl-phenyl)-propionic acid,
(S)-2-Ethoxy-3-{2-methyl-4-[3-(5-methyl-2-phenyl-oxazol-4-yl)-propoxy]-phenyl}-propionic acid,
(S)-2-Ethoxy-3-[2-methyl-4-(2-phenyl-oxazol-4-ylmethoxy)-phenyl]-propionic acid,
(S)-3-{4-[2-(2-Chloro-phenyl)-oxazol-4-ylmethoxy]-2-methyl-phenyl}-2-ethoxy-propionic acid,
(S)-2-Ethoxy-3-{4-[2-(3-methoxy-phenyl)-oxazol-4-ylmethoxy]-2-methyl-phenyl}-propionic acid,
(S)-3-{4-[2-(4-tert-Butyl-phenyl)-5-methyl-oxazol-4-ylmethoxy]-2-ethoxy-phenyl}-2-ethoxy-propionic acid,
(S)-2-Ethoxy-3-{2-ethoxy-4-[2-(4-isopropoxy-phenyl)-5-methyl-oxazol-4-ylmethoxy]-phenyl}-propionic acid,
(S)-3-{4-[2-(3-Chloro-phenyl)-5-methyl-oxazol-4-ylmethoxy]-2-ethoxy-phenyl}-2-ethoxy-propionic acid,
(S)-2-Ethoxy-3-{2-ethoxy-4-[2-(5-methyl-2-phenyl-oxazol-4-yl)-ethoxy]-phenyl}-propionic acid,
(S)-2-Ethoxy-3-{2-ethoxy-4-[3-(5-methyl-2-phenyl-oxazol-4-yl)-propoxy]-phenyl}-propionic acid,
(S)-3-{4-[2-(4-tert-Butyl-phenyl)-5-methyl-oxazol-4-ylmethoxy]-2-isopropoxy-phenyl}-2-ethoxy-propionic acid, and
(S)-2-Ethoxy-3-[2-fluoro-4-(5-methyl-2-o-tolyl-oxazol-4-ylmethoxy)-phenyl]-propionic acid,
and pharmaceutically acceptable salts and/or pharmaceutically acceptable esters thereof.

Particularly preferred compounds of formula (I) are those selected from the group consisting of
(S)-2-Ethoxy-3-[2-methyl-4-(5-methyl-2-o-tolyl-oxazol-4-ylmethoxy)-phenyl]-propionic acid,
(S)-2-Ethoxy-3-{4-[2-(4-isopropoxy-phenyl)-5-methyl-oxazol-4-ylmethoxy]-2-methyl-phenyl}-propionic acid,
(S)-2-Ethoxy-3-[2-methyl-4-(5-methyl-2-phenyl-oxazol-4-ylmethoxy)-phenyl]-propionic acid,
(S)-2-Ethoxy-3-{4-[2-(4-fluoro-3-methyl-phenyl)-5-methyl-oxazol-4-ylmethoxy]-2-methyl-phenyl}-propionic acid,
(S)-2-Ethoxy-3-{4-[2-(2-fluoro-phenyl)-5-methyl-oxazol-4-ylmethoxy]-2-methyl-phenyl}-propionic acid,
(S)-2-Ethoxy-3-{2-ethyl-4-[2-(4-fluoro-3-methyl-phenyl)-5-methyl-oxazol-4-ylmethoxy]-phenyl}-propionic acid,
(S)-2-Ethoxy-3-[2-fluoro-4-(5-methyl-2-phenyl-oxazol-4-ylmethoxy)-phenyl]-propionic acid,
(S)-3-[2-Chloro-4-(5-methyl-2-phenyl-oxazol-4-ylmethoxy)-phenyl]-2-ethoxy-propionic acid,
(S)-3-{2-Chloro-4-[2-(4-fluoro-3-methyl-phenyl)-5-methyl-oxazol-4-ylmethoxy]-phenyl}-2-ethoxy-propionic acid,
(S)-3-{2-Chloro-4-[2-(2-fluoro-phenyl)-5-methyl-oxazol-4-ylmethoxy]-phenyl}-2-ethoxy-propionic acid,
(S)-2-Ethoxy-3-[4-(5-methyl-2-phenyl-oxazol-4-ylmethoxy)-2-trifluoromethyl-phenyl]-propionic acid,
(S)-3-{2-Hydroxy-4-[2-(5-methyl-2-phenyl-oxazol-4-yl)-ethoxy]-phenyl}-2-methoxy-propionic acid,
(S)-2-Ethoxy-3-{4-[2-(4-isopropyl-phenyl)-5-methyl-oxazol-4-ylmethoxy]-2-methoxy-phenyl}-propionic acid,
(S)-3-[2,6-Dimethyl-4-(5-methyl-2-phenyl-oxazol-4-ylmethoxy)-phenyl]-2-ethoxy-propionic acid,
(S)-2-Ethoxy-3-{4-[2-(4-isopropyl-phenyl)-5-methyl-oxazol-4-ylmethoxy]-2,6-dimethyl-phenyl}-propionic acid,
(S)-2-Ethoxy-3-(4-{2-[2-(2-ethoxy-4-fluoro-phenyl)-5-methyl-oxazol-4-yl]-ethoxy}-2-methyl-phenyl)-propionic acid,
(S)-2-Ethoxy-3-{2-methyl-4-[3-(5-methyl-2-phenyl-oxazol-4-yl)-propoxy]-phenyl}-propionic acid,
(S)-2-Ethoxy-3-{4-[2-(3-methoxy-phenyl)-oxazol-4-ylmethoxy]-2-methyl-phenyl}-propionic acid,
(S)-3-{4-[2-(4-tert-Butyl-phenyl)-5-methyl-oxazol-4-ylmethoxy]-2-ethoxy-phenyl}-2-ethoxy-propionic acid, and
(S)-3-{4-[2-(4-tert-Butyl-phenyl)-5-methyl-oxazol-4-ylmethoxy]-2-isopropoxy-phenyl}-2-ethoxy-propionic acid,
and pharmaceutically acceptable salts and/or pharmaceutically acceptable esters thereof.

Other particularly preferred compounds of formula (I) are those selected from the group consisting of
(S)-2-Ethoxy-3-[2-methyl-4-(5-methyl-2-o-tolyl-oxazol-4-ylmethoxy)-phenyl]-propionic acid,
(S)-2-Ethoxy-3-{4-[2-(4-isopropoxy-phenyl)-5-methyl-oxazol-4-ylmethoxy]-2-methyl-phenyl}-propionic acid,
(S)-2-Ethoxy-3-[2-methyl-4-(5-methyl-2-phenyl-oxazol-4-ylmethoxy)-phenyl]-propionic acid,
(S)-2-Ethoxy-3-{4-[2-(4-fluoro-3-methyl-phenyl)-5-methyl-oxazol-4-ylmethoxy]-2-methyl-phenyl}-propionic acid,
(S)-2-Ethoxy-3-{4-[2-(2-fluoro-phenyl)-5-methyl-oxazol-4-ylmethoxy]-2-methyl-phenyl}-propionic acid,
(S)-2-Ethoxy-3-{2-ethyl-4-[2-(4-fluoro-3-methyl-phenyl)-5-methyl-oxazol-4-ylmethoxy]-phenyl}-propionic acid,
(S)-2-Ethoxy-3-[2-fluoro-4-(5-methyl-2-phenyl-oxazol-4-ylmethoxy)-phenyl]-propionic acid,
(S)-3-[2-Chloro-4-(5-methyl-2-phenyl-oxazol-4-ylmethoxy)-phenyl]-2-ethoxy-propionic acid,
(S)-3-{2-Chloro-4-[2-(4-fluoro-3-methyl-phenyl)-5-methyl-oxazol-4-ylmethoxy]-phenyl}-2-ethoxy-propionic acid,
(S)-3-{2-Chloro-4-[2-(2-fluoro-phenyl)-5-methyl-oxazol-4-ylmethoxy]-phenyl}-2-ethoxy-propionic acid,
(S)-2-Ethoxy-3-[4-(5-methyl-2-phenyl-oxazol-4-ylmethoxy)-2-trifluoromethyl-phenyl]-propionic acid,
(S)-2-Ethoxy-3-{4-[2-(4-isopropyl-phenyl)-5-methyl-oxazol-4-ylmethoxy]-2-methoxy-phenyl}-propionic acid,
(S)-3-[2,6-Dimethyl-4-(5-methyl-2-phenyl-oxazol-4-ylmethoxy)-phenyl]-2-ethoxy-propionic acid,
(S)-2-Ethoxy-3-{4-[2-(4-isopropyl-phenyl)-5-methyl-oxazol-4-ylmethoxy]-2,6-dimethyl-phenyl}-propionic acid,
(S)-2-Ethoxy-3-{4-[2-(3-methoxy-phenyl)-oxazol-4-ylmethoxy]-2-methyl-phenyl}-propionic acid,
(S)-3-{4-[2-(4-tert-Butyl-phenyl)-5-methyl-oxazol-4-ylmethoxy]-2-ethoxy-phenyl}-2-ethoxy-propionic acid, and
(S)-3-{4-[2-(4-tert-Butyl-phenyl)-5-methyl-oxazol-4-ylmethoxy]-2-isopropoxy-phenyl}-2-ethoxy-propionic acid,
and pharmaceutically acceptable salts and/or pharmaceutically acceptable esters thereof.

Each of the compounds mentioned above individually constitutes a preferred embodiment of the present invention, particularly (S)-2-Ethoxy-3-{4-[2-(2-fluoro-phenyl)-5-methyl-oxazol-4-ylmethoxy]-2-methyl-phenyl}-propionic acid and pharmaceutically acceptable salts and/or pharmaceutically acceptable esters thereof. Another example of a preferred individual compound is (S)-2-Ethoxy-3-[2-methyl-4-

(5-methyl-2-o-tolyl-oxazol-4-ylmethoxy)-phenyl]-propionic acid and pharmaceutically acceptable salts and/or pharmaceutically acceptable esters thereof. Compounds as described above, which are not pharmaceutically acceptable salts and/or pharmaceutically acceptable esters are preferred.

Compounds of formula (I) have one or more asymmetric carbon atoms and can exist in the form of optically pure enantiomers, optically pure diastereoisomers or mixtures of diastereoisomers. The optically active forms can be obtained for example by resolution of the racemates, by asymmetric synthesis or asymmetric chromatography (chromatography with a chiral adsorbens or eluant). The invention embraces all forms, wherein the asymmetric carbon to which $R^5$ is attached is of the S configuration.

It will be appreciated, that the compounds of general formula (I) in this invention may be derivatised at functional groups to provide derivatives which are capable of conversion back to the parent compound in vivo. Physiologically acceptable and metabolically labile derivatives, which are capable of producing the parent compounds of general formula (I) in vivo are also within the scope of this invention.

A further aspect of the present invention is the process for the manufacture of compounds of formula (I) as defined above, which process comprises removing a protecting group in a compound of formula (II)

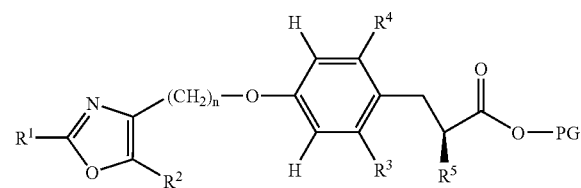

(II)

wherein $R^1$, $R^2$, $R^3$, $R^4$, $R^5$ and n are as defined before and PG is a protecting group.

Possible protecting groups PG in compounds of formula (II) are e.g. lower-alkyl-, β-trimethylsilylethyl- and β-trichloroethyl-esters, which can be used for the protection of the corresponding carboxy group. Lower-alkyl-ester protecting groups can be removed in the presence of a base such as e.g. LiOH or NaOH in a solvent such as e.g. $H_2O$, ethanol, tetrahydrofuran, or dioxan, or in a mixture of such solvents, e.g. in a temperature range of 10-50° C. The β-trichloroethyl-ester protecting group can be removed in the presence of Zn in acetic acid, e.g. in a temperature range of 10-50° C. The β-trimethylsilylethyl-ester protecting group can be removed in the presence of tetrabutylammonium fluoride in tetrahydrofuran, e.g. in a temperature range of 20-65° C. Methods for converting a compound of formula (I) as defined above to a pharmaceutically acceptable salt are known in the art.

The invention further relates to compounds of formula (I) as defined above, when manufactured according to a process as defined above.

As described above, the compounds of formula (I) of the present invention can be used as medicaments for the treatment and/or prevention of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases (such as e.g. crown disease, inflammatory bowel disease, collitis, pancreatitis, cholestasis/fibrosis of the liver, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment and/or prevention of non-insulin dependent diabetes mellitus is preferred.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prevention of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably non-insulin dependent diabetes mellitus.

In another embodiment, the invention relates to a method for the treatment and/or prevention of diseases which are modulated by PPARα and/or PPARγ agonists, which method comprises administering a compound of formula (I) to a human or animal.

Preferred examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably for the treatment and/or prevention of non-insulin dependent diabetes mellitus.

The invention further relates to the use of compounds as defined above for the treatment and/or prevention of diseases which are modulated by PPARα and/or PPARγ agonists. Preferred examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably non-insulin dependent diabetes mellitus.

In addition, the invention relates to the use of compounds as defined above for the preparation of medicaments for the treatment and/or prevention of diseases which are modulated by PPARα and/or PPARγ agonists. Preferred examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably non-insulin dependent diabetes mellitus. Such medicaments comprise a compound as defined above.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

Homochiral compounds of formula (I) (compounds 10 and 11 in scheme 1 and compounds 6 and 7 in scheme 3) can be prepared according to the methods depicted in scheme 1 and 3 or by analogous methods.

Racemates of compounds of formula (I) [compounds 9 and compounds 10 in scheme 2 and compounds 9 and 11 in scheme 4] can e.g. be synthesized according to the methods depicted in scheme 2 or 4 or by analogous methods. The optically pure (S) enantiomer can then be prepared from racemates of compounds of formula (I) by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent.

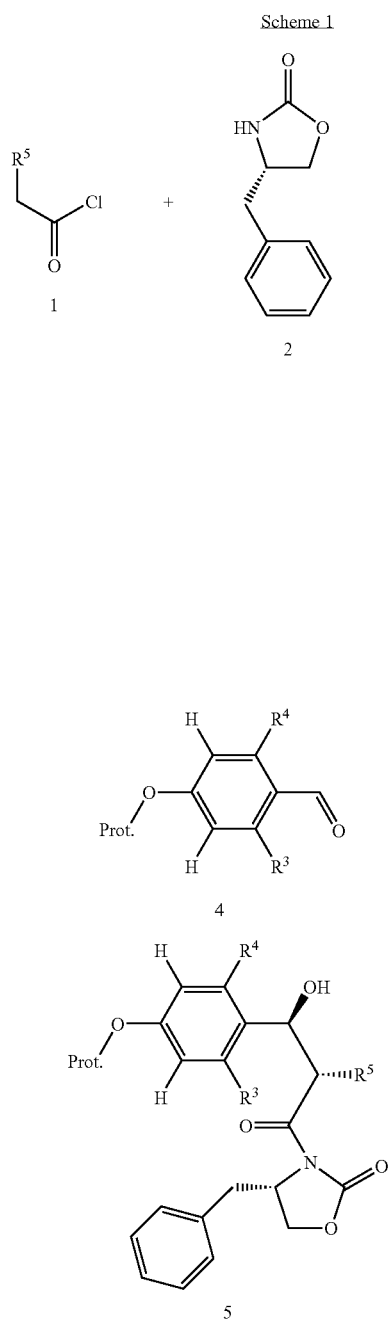

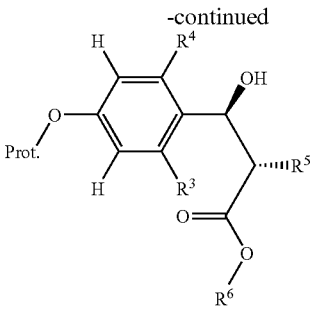

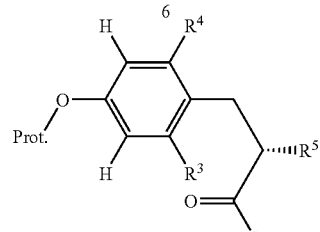

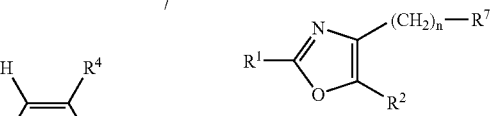

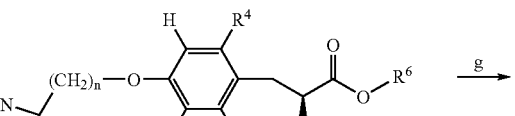

Homochiral alpha-alkoxy-phenyl-propionic acid esters of formula 10 and free acids of formula 11 can be prepared according to the method depicted in scheme 1 or by analogous methods known in the art.

The well known chiral auxiliary 2 [(S)-4-benzyl-oxazolidin-2-one] is condensed with an alkoxy-acetyl chloride 1 in the presence of a strong base like n-butyl lithium in an inert solvent like tetrahydrofuran at temperatures around −78° C. to produce building block 3 (step a). The latter is then treated according to literature precedence [Tetrahedron Asymmetry (1999), 10, 1353-1367] with dibutylboron-triflate and a tertiary amine like triethylamine in dichloromethane to generate the corresponding boron enolate, which is subsequently reacted at low temperatures with aldehydes 4 (prepared as outlined in scheme 5) resulting in compounds 5 (step b). In these aldol products 5, one of all four possible stereoisomers is strongly predominating (stereochemistry as indicated without rigorous proof with respect to the benzylic position). Compounds 5 are converted into phenolic intermediates 8 via a three step sequence encompassing: i) carefully controlled ester formation using only a minimal excess of alcoholate in the corresponding alcohol as solvent or in solvents like tetrahydrofuran or dioxane at temperatures ranging from −20° C. to room temperature to give ester compounds 6 (step c); ii) removal of the benzylic hydroxy group in 6 with a reducing agent like e.g. triethylsilane in the presence of a Lewis acid, like boron-trifluoride, or a protic acid, like trifluoroacetic acid, in a suitable solvent like trifluoroacetic acid itself or dichloromethane between 0° C. and 60° C. to yield protected phenol compounds 7 (step d); iii) ensuing removal of the protecting group, e.g. a benzyl group, by standard technology, e.g. catalytic hydrogenation using hydrogen and a catalyst like palladium or by using dimethyl sulfide and boron trifluoride diethyl etherate in a solvent like dichloromethane between room temperature and the reflux temperature of the solvent to give phenolic compounds 8 (step e); the order of the three reaction steps c, d, e is interchangeable, and catalytic hydrogenation can also be used for the simultaneous removal of the benzylic hydroxy function and a benzyl protecting group, preferably using palladium on charcoal as catalyst in the presence of an acid like oxalic acid in solvents like alcohols at temperatures around room temperature and a hydrogen pressure up to 100 bar.

Aryl-oxazole compounds 9 (prepared as outlined in schemes 6 and 7) are condensed with phenols 8 according to well known procedures: if $R^7$ represents a hydroxy group e.g. via Mitsunobu-reaction, with triphenylphosphine and di-tert-butyl-, diisopropyl- or diethyl-azodicarboxylate as reagents; this transformation is preferably carried out in a solvent like toluene, dichloromethane or tetrahydrofuran at ambient temperature. Alternatively, if $R^7$ represents a halide, mesylate or tosylate moiety, the aryl-oxazole compounds 9 can be reacted with phenols 8 in solvents like N,N-dimethylformamide, acetonitrile, acetone or methyl-ethyl ketone in the presence of a weak base like cesium or potassium carbonate at a temperature ranging from room temperature to 140° C., preferably around 50° C. to yield ether compounds 10 (step f). Those can optionally be hydrolyzed according to standard procedures, e.g. by treatment with an alkali hydroxide like LiOH or NaOH in a polar solvent mixture like tetrahydrofuran/ethanol/water leading to carboxylic acids 11 (step g). If carefully controlled reaction conditions are applied as detailed in the experimental part, hardly any racemisation occurs during this reaction sequence. The optical purity of compounds 10 and 11 can be determined by chiral HPLC or by $^1$H-NMR-spectroscopy in the presence of a chiral solvent like 1-(9-anthryl)-2,2,2-trifluoro-ethanol and has been found higher than 95% in all cases exemplified.

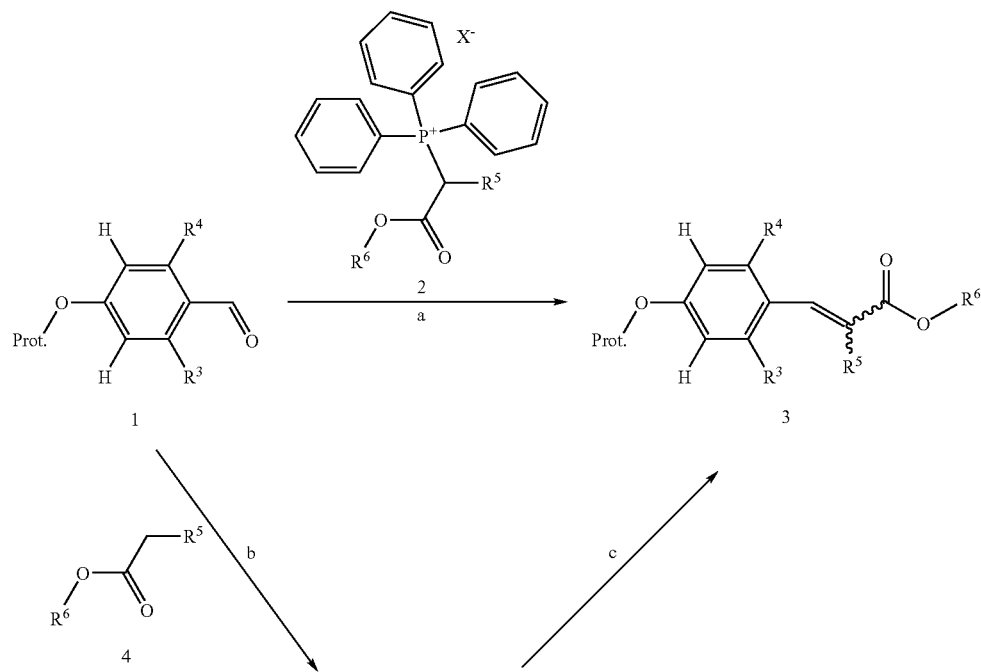

Scheme 2

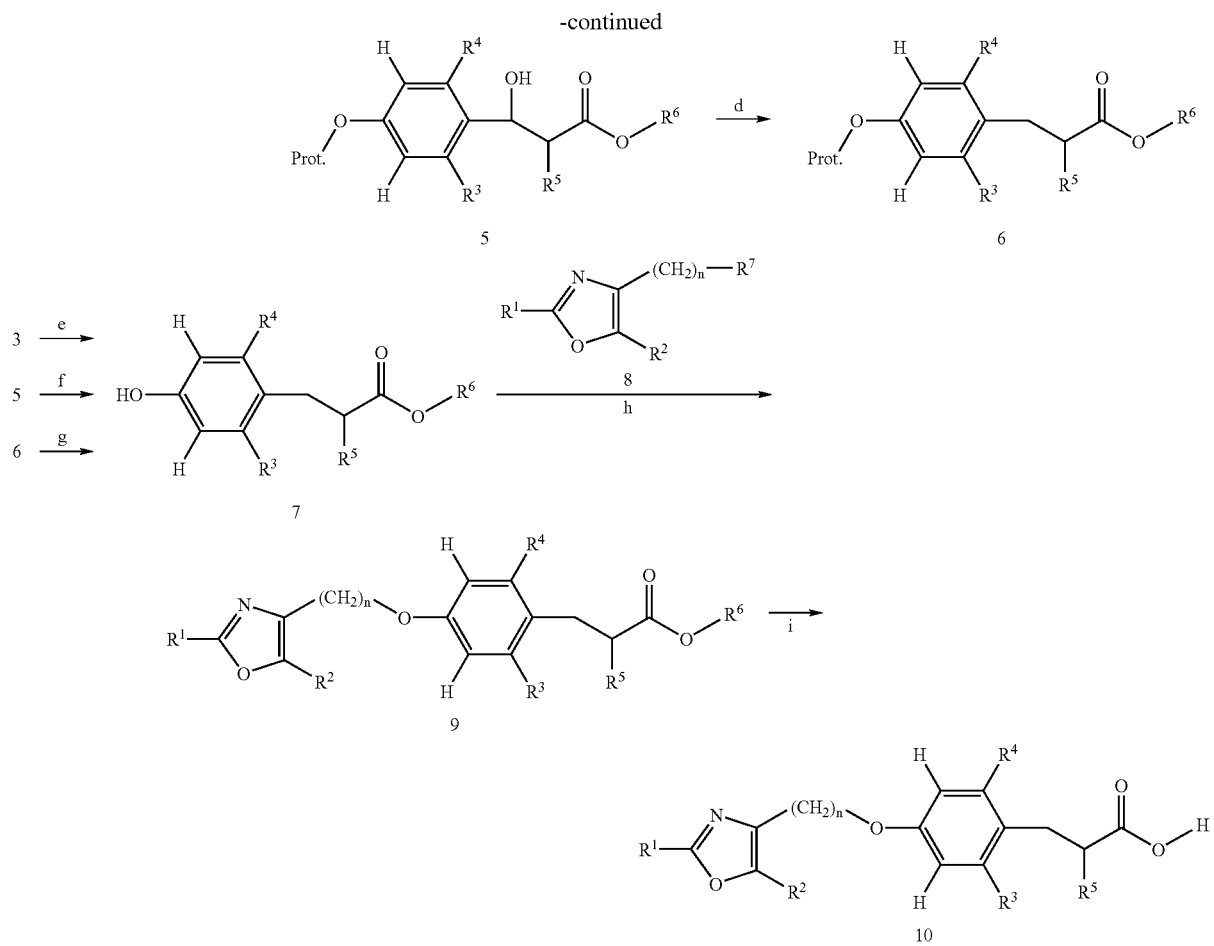

Aldehydes 1 (prepared as outlined in scheme 5) can be reacted with a Wittig salt 2 such as (1,2-diethoxy-2-oxoethyl)triphenyl phosphonium chloride or (1,2-dimethoxy-2-oxoethyl)triphenyl phosphonium bromide in solvents like isopropanol, dichloromethane or tetrahydrofuran or mixtures thereof in the presence of a base like potassium carbonate, 1,8-diazabicyclo[5.4.0]undec-7-ene (DBU) or 1,1,3,3-tetramethyl-guanidine, preferably between 0° C. and the reflux temperature of the solvents, giving acrylic esters 3 as E and/or Z isomers (step a). Hydrogenation of acrylic esters 3 using palladium on charcoal as catalyst, preferably at room temperature and 1 atm. pressure of hydrogen, in solvents like methanol, ethanol, tetrahydrofuran, acetic acid, dichloromethane and mixtures thereof, affords racemic esters 7, provided that the protecting group can be cleaved reductively (step e).

Alternatively, aldehydes 1 are reacted with the enolate of alkoxy-acetic acid esters 4 (preferably the lithium-enolate, prepared at −78° C. by treatment of 4 with a strong, non-nucleophilic base like lithium diisopropylamide in an inert solvent like tetrahydrofuran), preferably at temperatures around −78° C., in solvents like tetrahydrofuran giving the aldol product 5 as a mixture of diasteromers (step b). Removal of the benzylic hydroxy group as described above for the conversion of compounds 6 to compounds 7 in scheme 1 yields racemic esters 6 (step d); ensuing removal of the protecting group, e.g. a benzyl group, can then be performed by standard technology as described for the conversion of compounds 7 to compounds 8 in scheme 1 to give phenolic compounds 7 (step g). Catalytic hydrogenation can also be used to convert in one step benzyl protected hydroxy compounds 5 into phenolic compounds 7 (step f) as described for the conversion of compounds 6 to compounds 8 in scheme 1. The cleavage of the protective function can also be performed before the removal of the benzylic hydroxy group; in such a case, similar reaction conditions can be chosen for the removal of the benzylic hydroxy group as just described for the transformation of compounds 5.

As an alternative method, compounds 5 can be treated with catalytic amounts of an acid like para toluene sulfonic acid in a solvent like benzene or toluene, preferably under conditions allowing the removal of the water formed (e.g. with a Dean Stark trap or in the presence of molecular sieves) at temperatures between room temperature and the reflux temperature of the solvents to yield acrylic esters 3 (step c).

The transformation of phenolic intermediates 7 into esters 9 and/or acids 10 can be performed in perfect analogy as described for homochiral phenolic intermediates 8 in scheme 1 (steps h and i).

Scheme 3
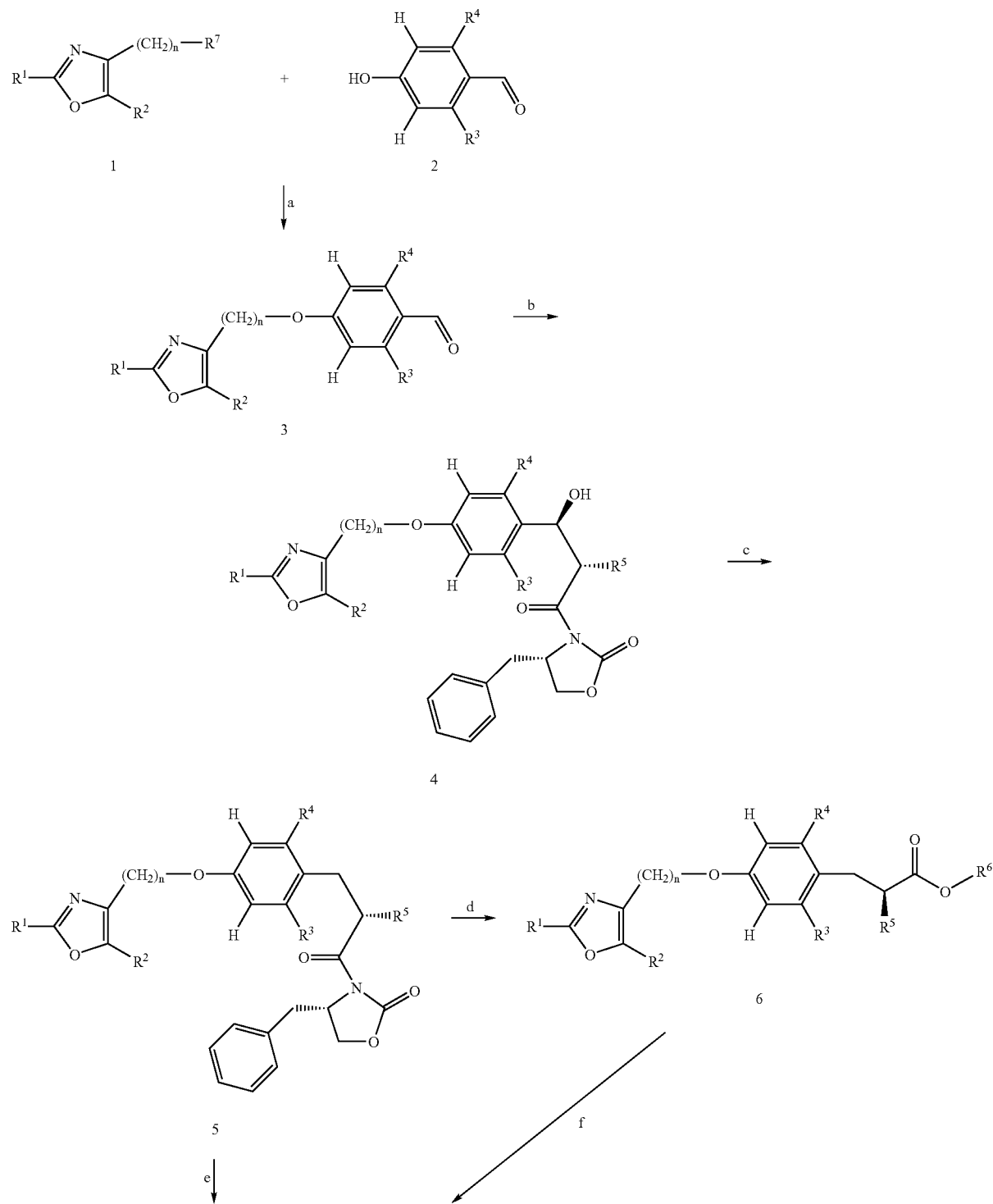

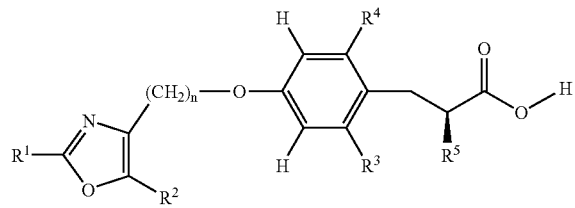

Homochiral alpha-alkoxy-phenyl-propionic acid esters of formula 6 and free acids of formula 7 can also be prepared according to a linear synthetic sequence depicted in scheme 3. Thus, reaction types already described in scheme 1 are used in a different order beginning with the condensation of aryl-oxazole synthons 1 (prepared as outlined in schemes 6 and 7) with phenols 2 (prepared as outlined in scheme 5) affording ether compounds 3 bearing an aldehyde moiety (step a). In case $R^3$ and/or $R^4$ contain a functional group, which might not be compatible with the following reaction steps, e.g. $R^3$ and/or $R^4$ might be a phenolic OH-function, then a protective group should be attached to such a functional group, e.g. a tert-butly-dimethyl-silyl moiety. Such a protective group can then be removed at a suitable stage later in the reaction sequence.

These ether compounds 3 are then reacted with the chiral synthons (compounds 3 in scheme 1) to form aldol-adducts 4 (step b). Removal of the benzylic hydroxy function in compounds 4 leads to compounds 5 (step c), which can be converted into the corresponding esters 6 (step d) or acids 7 (step e) as described for the analogous reactions in scheme 1 and 2, respectively.

Optionally, ester compounds 6 can be hydrolysed to acids 7 (step f). The optical purity of compounds 6 and 7 can be determined by chiral HPLC or by $^1$H-NMR-spectroscopy in the presence of a chiral solvent like 1-(9-anthryl)-2,2,2-trifluoro-ethanol and has been found to be higher than 95% in all cases exemplified.

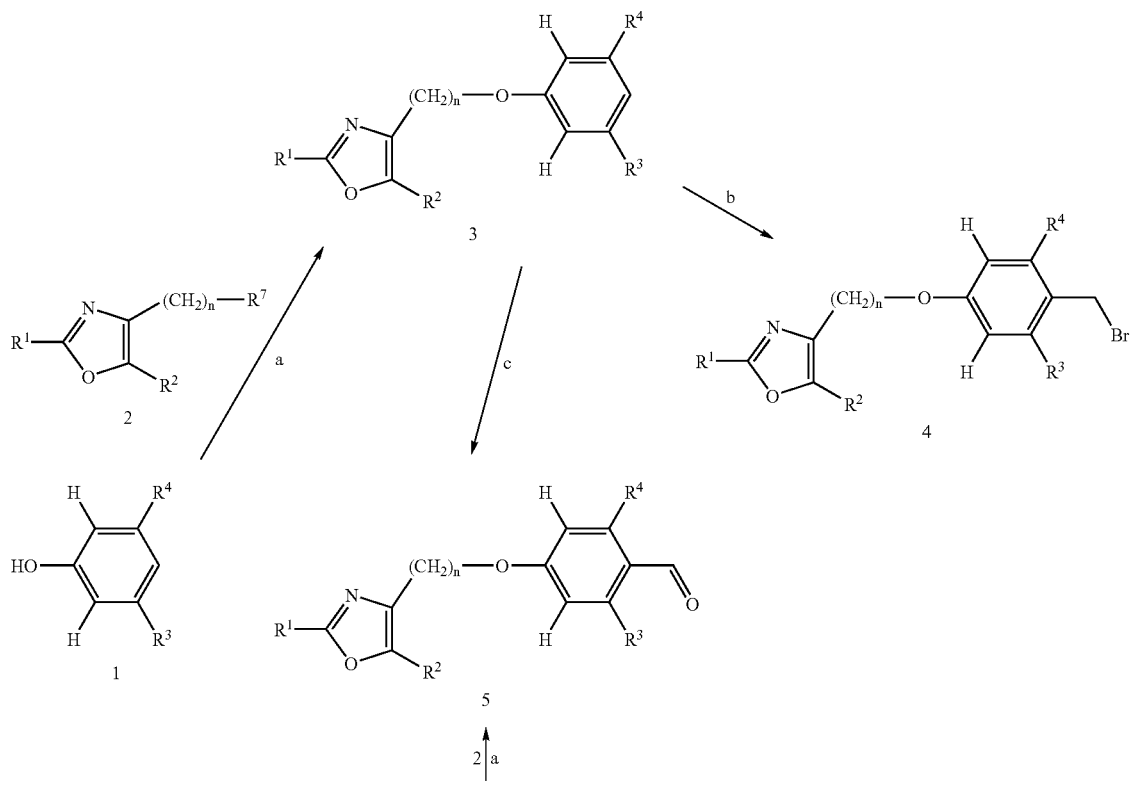

Scheme 4

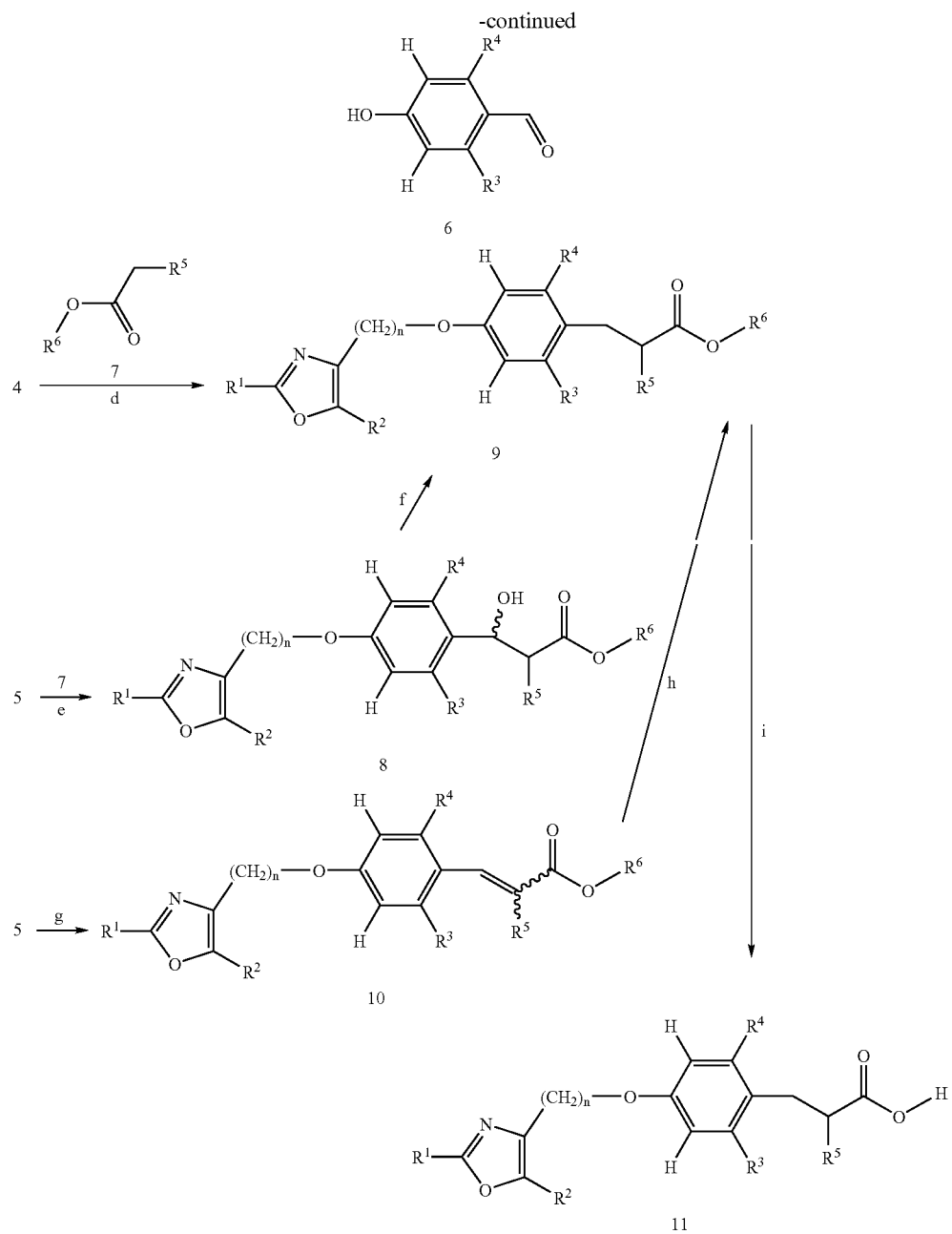

Aryl-oxazole compounds 2 (prepared as outlined in schemes 6 and 7) are condensed with phenols 1 or aldehydes 6 (prepared as outlined in scheme 5) in perfect analogy as described for homochiral phenolic intermediates 8 and aryl-oxazole compounds 9 in scheme 1; thus ether compounds 3 or aldehydes 5 are obtained (step a). The former are then subjected to bromomethylation, e.g. by treatment with tri-oxane and HBr, preferably 62% aq. HBr, in an inert solvent, preferably dichloromethane, preferably at 0° C. giving a highly reactive, often quite unstable electrophile 4 (step b). The electrophile 4 is suitable to alkylate an enolate of alkoxy-acetic acid esters 7 ($R^6$=lower alkyl), preferably the lithium-enolate, prepared at −78° C. by treatment of 7 with a strong, non-nucleophilic base like lithium diisopropyla-mide in an inert solvent like tetrahydrofuran, to give esters 9 (step d). To increase the reactivity of the enolate nucleo-phile, the reaction is preferably performed in the presence of a cosolvent like hexamethylphosphoramide (HMPA) or 1,3-dimethyl-3,4,5,6-tetrahydro-2(1H)-pyrimidinone (DMPU).

Alternatively, aldehyde compounds 5, which are also available from ether intermediates 3 by Vilsmeier formyla-tion or through formylation with dichloromethyl methyl ether in the presence of titanium tetrachloride, preferably in dichloromethane at temperatures between −78° C. and the reflux temperature of the solvent (step c), are reacted with an enolate of alkoxy-acetic acid esters 7 as described for the analogous reaction of compounds 1 and compounds 4 in scheme 2 giving the aldol products 8 as a mixture of diasteromers (step e). Removal of the benzylic hydroxy group in compounds 8 leads to racemic esters 9 (step f), as described for the analogous reactions in scheme 1, 2 and 3, respectively.

Alternatively, aldehydes 5 can be reacted with a Wittig salt as described for the conversion of compounds 1 to compounds 3 in scheme 2 giving acrylic esters 10 as E and/or Z isomers (step g). Hydrogenation of acrylic esters 10 as described for the analogous reaction in scheme 2 leads to compounds 9 (step h). Hydrolysis of racemic ester compounds 9 can be performed in perfect analogy as described for homochiral compounds 10 in scheme 1 leading to carboxylic acids 11 (step i).

Aldehydes 4 (scheme 1), aldehydes 1 (scheme 2), aldehydes 2 (scheme 3), and aldehydes 6 (scheme 4) are known or can be synthesized by methods known in the art. Examples for possible syntheses of these key intermediates are given in scheme 5.

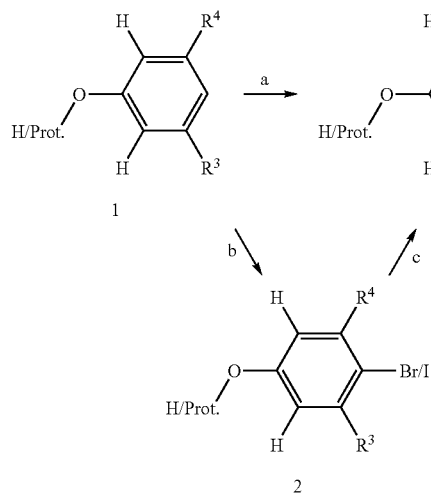

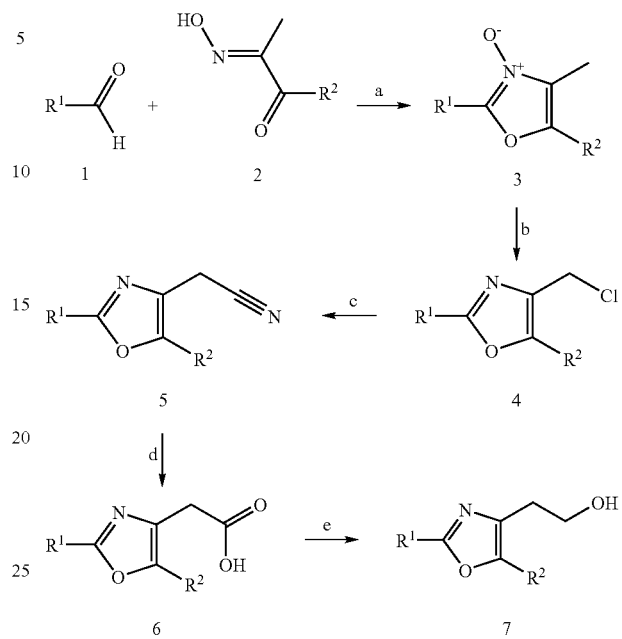

Known phenols 1 can be transformed into aldehydes 3 either by known formylation reactions such as e.g. the Vilsmeier formylation, by treatment with hexamethylene tetramine under acidic conditions, e.g. in the presence of sulfuric acid or, preferably, with trifluoroacetic acid as solvent between 0° C. and the reflux temperature of trifluoroacetic acid, or by formylation with dichloromethyl methyl ether in the presence of titanium tetrachloride, preferably in dichloromethane at temperatures between −78° C. and the reflux temperature of the solvent (step a); alternatively, a two step procedure might be used: introduction of a halogen atom into the para position, e.g. by use of N-bromo- or N-iodo-succinimide, e.g. in a mixture of concentrated sulfuric acid and tetrahydrofuran preferably at ambient temperature, followed by a metal halogen exchange, realized by treatment with an alkyl-lithium reagent like n-butyllithium, preferably at temperatures around −78° C., and quenching the resulting aryl-Li with a formyl transfer reagent like N,N-dimethylformamide or N-formyl-piperidine (steps b and c). Alternatively, a carbonylation reaction can be used for the introduction of the formyl group in step c, e.g. by use of sodium formate, bis(triphenylphosphine) palladium(II) dichloride and CO gas in a solvent like N,N-dimethylformamide, preferably at temperatures around 100° C.

Aldehydes 1 are commercially available or known. They are condensed with diketo-monoximes 2 according to literature precedence (Diels, O.; Riley, K.; Chem Ber (1915), 48, 897) in the presence of a strong acid, typically HCl, in a polar solvent like AcOH to yield the oxazole-N-oxides 3 (step a). Subsequent treatment with $POCl_3$ in dichloromethane under reflux provides the corresponding primary chlorides 4 (Goto, Y.; Yamazaki, M.; Hamana, M.; Chem Pharm Bull (1971), 19, 2050, step b. The primary chlorides 4 are either used as such or transformed according to well established methods into the corresponding primary alcohols [e.g. with acetic acid in the presence of sodium iodide, potassium carbonate at elevated temperature and subsequent saponification of the acetate formed (e.g. with lithium hydroxide in ethanol/water at room temperature)]. Alternatively, the primary chlorides 4 are further elaborated via $S_N2$-reaction with NaCN to give, via nitrils 5 (step c), exhaustive hydrolysis (step d) and reduction (step e), e.g. with borane in tetrahydrofuran, the building blocks 7. Hydroxy-ethyl compounds 7 or the hydroxymethyl compounds prepared form primary chlorides 4 correspond to or can be converted into compounds 9 (scheme 1), 8 (scheme 2), 1 (scheme 3) or 2 (scheme 4) e.g. by treatment with methanesulfonyl chloride in dichloromethane in the presence of a base like triethylamine preferably in a temperature range between −20° C. and room temperature or by reaction with carbon tetrachloride or carbon tetrabromide and triphenylphosphine in solvents like tetrahydrofuran preferably in a temperature range between room temperature and the reflux temperature of the solvents; thus yielding compounds 9 (scheme 1), 8 (scheme 2), 1 (scheme 3) or 2 (scheme 4) as methanesulfonates, chlorides or bromides, respectively.

4-Chloromethyl-2-aryl or 2-heteroaryl-oxazoles 4 with $R^2$ equal hydrogen are preferably prepared from the corresponding aryl or heteroaryl carboxamides and 1,3-dichloroacetone as described e.g. in Bioorg. Med. Chem. Lett. (2000), 10(17), 2041-2044.

Scheme 7

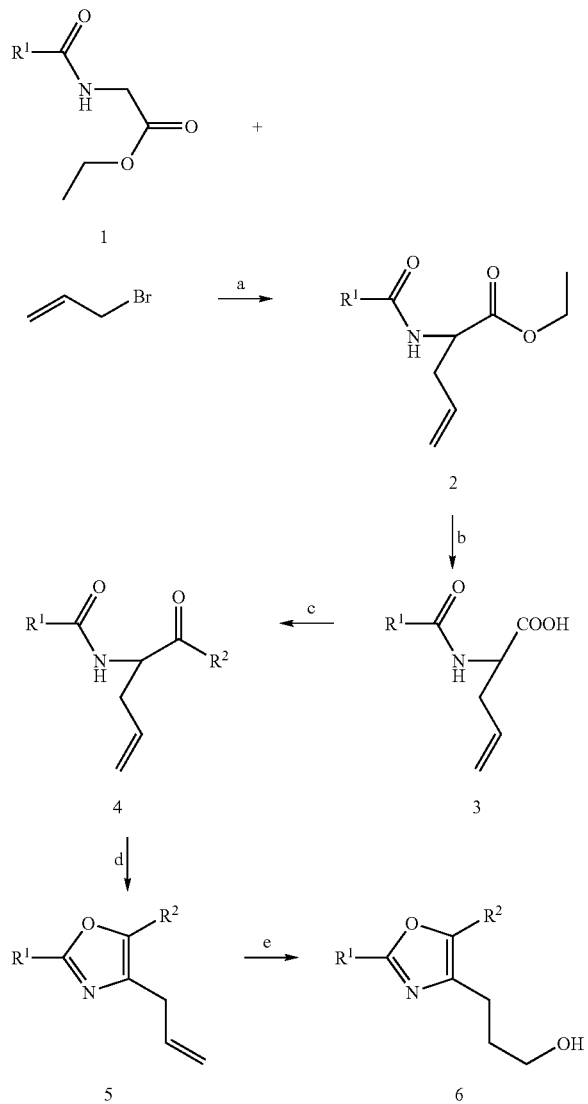

N-Acyl-glycine esters 1 are either commercially available, known, or can be prepared by standard operations of N-acylation. Mono-allylated esters 2 can easily be obtained by double deprotonation of 1 with a strong, non-nucleophilic base like LiHMDS in an aprotic solvent like THF, typically at −78° C., followed by treatment with allyl bromide to produce selectively the C-alkylated products 2 (step a). Standard hydrolysis generates intermediate acids 3 (step b), which are then transformed, following well established literature precedence (J. Med. Chem. (1996), 39, 3897), into compounds 4 (step c). Ring-closure to the oxazole using trifluoro-acetic acid and trifluoro-acetic anhydride or Burgess-reagent (methyl-N-triethylammoniosulfonyl-carbamate) generates key intermediates 5 (step d), which, finally, are elaborated via hydroboration to the target alcohols 6, e.g. with 9-BBN in THF and ensuing oxidative work-up with $H_2O_2$ and NaOH (step e). Alcohols 6 correspond to or can be converted into compounds 9 (scheme 1), 8 (scheme 2), 1 (scheme 3) or 2 (scheme 4) e.g. by treatment with methanesulfonyl chloride in dichloromethane in the presence of a base like triethylamine preferably in a temperature range between −20° C. and room temperature or by reaction with carbon tetrachloride or carbon tetrabromide and triphenylphosphine in solvents like tetrahydrofuran preferably in a temperature range between room temperature and the reflux temperature of the solvents; thus yielding compounds 9 (scheme 1), 8 (scheme 2), 1 (scheme 3) or 2 (scheme 4) as methanesulfonates, chlorides or bromides, respectively.

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257: 112-119.

Full-length cDNA clones for human PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in E. coli strain BL21 (pLysS) cells by standard methods (Ref: Current Protocols in Molecular Biology, Wiley Press, edited by Ausubel et al.).

Radioligand Binding Assay

PPARα receptor binding was assayed in TKE10 (10 mM Tris-HCl, pH 8, 50 mM KCl, 2 mM EDTA, 0.1 mg/ml fatty acid free BSA and 10 mM DTT). For each 96 well 2.4 ug equivalent of GST-PPARα-LBD fusion protein and radioligand, e.g. 40000 dpm 2(S)-(2-benzoyl-phenylamino)-3-{4-[1,1-ditritio-2-(5-methyl-2-phenyl-oxazol-4-yl)-ethoxy]-phenyl}-propionic acid, were incubated in 100 ul volume at RT for 2 hrs. Bound ligand was removed from unbound ligand by solid phase separation using MultiScreen plates (Millipore) filled with 80 ul of SG25 according to the manufacturer's recommendations.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 ug SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containig the recptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% O2:5% $CO_2$ atmosphere. Cells were seeded in 6 well plates at a density of $10^5$ Cells/well and then transiently batch-transfected with either the pFA-PPARγ-LBD or pFA-PPARα-LBD expression plasmids plus a reporter plasmid and an expression plasmid encoding the secretable form of alkaline phosphatase (SEAP) as a normalization control. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final DMSO concentration: 0.1%). Following incubation of the cells for 24 hours with substances, 50 ul of the supernatant was recovered and analyzed for SEAP activity (Roche Molecular Biochemicals). The remainder of the supernatant was discarded, 50 ul PBS was added per well followed by one volume of Luciferase Constant-Light Reagent (Roche Molecular Biochemicals) to lyse the cells and initiate the luciferase reaction. Luminescence for both SEAP and luciferase was measured in a Packard TopCount. Luciferase activity was normalized to the SEAP control and transcriptional activation in the presence of a test substance was expressed as fold-activation over cells incubated in the absence of the substance. EC50 values were calculated using the XLfit program (ID Business Solutions Ltd. UK).

The free acids of the compounds of the present invention ($R^6$ is hydrogen) exhibit $IC_{50}$ values of 0.1 nM to 50 μM, preferably 1 nM to 10 μM for PPARα and PPARγ. The compounds further exhibit $EC_{50}$ values of 0.1 nM to 50 μM, preferably 1 nM to 10 μM for PPARα and PPARγ. Compounds, in which $R^6$ is not hydrogen are converted in vivo to compounds in which $R^6$ is hydrogen. The following table shows measured values for some selected compounds of the present invention and for a compound already known in the art (e.g.: Rosiglitazone, Drugs 1999, Vol 57(6), 921-930).

|  | PPARα $IC_{50}$ | PPARγ $IC_{50}$ | PPARα $EC_{50}$ | PPARγ $EC_{50}$ |
|---|---|---|---|---|
| Example 2 | 30 nmol/l | 58 nmol/l | 163 nmol/l | 115 nmol/l |
| Example 3 | 87 nmol/l | 506 nmol/l | 57 nmol/l | 87 nmol/l |
| Example 5 | 155 nmol/l | 146 nmol/l | 38 nmol/l | 124 nmol/l |
| Example 9 | 196 nmol/l | 129 nmol/l | 21 nmol/l | 33 nmol/l |
| Example 17 | 73 nmol/l | 31 nmol/l | 186 nmol/l | 174 nmol/l |
| Example 23 | 52 nmol/l | 48 nmol/l | 306 nmol/l | 138 nmol/l |
| Example 25 | 177 nmol/l | 129 nmol/l | 26 nmol/l | 75 nmol/l |
| Example 29 | 2380 nmol/l | 1730 nmol/l | 213 nmol/l | 678 nmol/l |
| Example 37 | 74 nmol/l | 318 nmol/l | 14 nmol/l | 12 nmol/l |
| Example 43 | 131 nmol/l | 33 nmol/l | 150 nmol/l | 57 nmol/l |
| Rosiglitazone | inactive | 1090 nmol/l | inactive | 405 nmol/l |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules).

Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 0.1 mg to about 1000 mg, especially about 0.1 mg to about 100 mg, comes into consideration. Depending on the dosage it is convenient to administer the daily dosage in several dosage units.

The pharmaceutical preparations conveniently contain about 0.05-500 mg, preferably 0.05-100 mg of a compound of formula (I).

The following examples serve to illustrate the present invention in more detail. They are, however, not intended to limit its scope in any manner.

EXAMPLES

Abbreviations:
AcOEt=ethyl acetate, AcOH=acetic acid, nBu$_2$BOTf=dibutylboron triflate, n-BuLi=n-butyllithium, DBAD=di-tert-butyl azodicarboxylate, DBU=1,8-diazabicyclo[5.4.0]undec-7-ene, DEAD=diethyl azodicarboxylate, DIAD=diisopropyl azodicarboxylate, DMPU=1,3-dimethyl-3,4,5,6-tetrahydro-2(1H)-pyrimidinone, eq.=equivalents, h=hour(s), HPLC=high performance liquid chromatography, LDA=lithium diisopropylamide, min=minute(s), POCl$_3$=phosphorous oxychloride, THF=tetrahydrofuran.

Example 1 a] (S)-4-Benzyl-3-[(2S,3R)-3-(4-benzyloxy-2-methyl-phenyl)-2-ethoxy-3-hydroxy-propionyl]-oxazolidin-2-one (S)-4-Benzyl-3-ethoxyacetyl-oxazolidin-2-one (12.45 g, 47 mmol) (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, *Tetrahedron: Asymmetry* 1999, 10, 1353-1367) was dissolved in dry dichloromethane (270 ml) under an argon atmosphere and the solution was cooled to −78° C. Triethylamine (7.98 ml, 57 mmol) was added, followed by the slow addition, over approximately 20 min, of di-n-butylboron triflate (1 M solution in dichloromethane, 50 ml, 50 mmol) such that the reaction temperature was kept below −70° C. The mixture was stirred at −78° C. for 50 min, the cooling bath was replaced with an ice bath and the mixture stirred at 0° C. for additional 50 min before being recooled to −78° C. A solution of 4-benzyloxy-2-methyl-benzaldehyde (10.7 g, 47 mmol) in dry dichloromethane (130 ml) was added over ca. 45 min, such that the reaction temperature was maintained below −70° C. The resulting mixture was stirred at −78° C. for 45 min, warmed from −78° C. to 0° C. and stirred at 0° C. for a further 1.5 h. The reaction mixture was poured onto ice water/brine and extracted two times with dichloromethane. The combined extracts were washed with brine and dried over sodium sulfate. The solvent was removed under reduced pressure and the residue purified by column chromatography (silica gel, cyclohexane/AcOEt) to give 22.3 g (45.6 mmol, 96%) of the title compound as colorless oil. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353-1367.

MS: 512.3 (M+Na)$^+$, 472.3, 447.2, 387.2, 327.2, 295.3, 267.3, 232.1, 175.1.

b] (2S,3R)-3-(4-Benzyloxy-2-methyl-phenyl)-2-ethoxy-3-hydroxy-propionic acid methyl ester A 5.4 M solution of sodium methoxide (7.3 ml, 39.5 mmol) was added to an ice-cooled and stirred suspension of (S)-4-benzyl-3-[(2S,3R)-3-(4-benzyloxy-2-methyl-phenyl)-2-ethoxy-3-hydroxy-propionyl]-oxazolidin-2-one (17.6 g, 36 mmol) in dry methanol (87 ml). The mixture was stirred at 0° C. for 15 min, quenched and neutralized by the addition of dilute aqueous hydrochloric acid (1.0 M). The solution was concentrated under reduced pressure and the residue dissolved in ice water/ethyl acetate 1/1. The layers were separated and the aqueous layer was extracted two times with ethyl acetate. The combined organic layers were washed with ice water and dried over sodium sulfate. The solvent was removed under reduced pressure and the residue purified by column chromatography (silica gel, cyclohexane/AcOEt) to give 8.6 g (25 mmol, 69%) of the title compound as light yellow oil. According to $^1$H-NMR spectroscopy, one single diastereomer was obtained.

MS: 367.2 (M+Na)$^+$, 362.2 (M+NH$_4$)$^+$, 327.3, 299.3, 239.3, 211.2.

c] (2S)-3-(4-Benzyloxy-2-methyl-phenyl)-2-ethoxy-propionic acid methyl ester

Triethylsilane (23 ml, 145 mmol) was added to a vigorously stirred, ice-cooled solution of (2S,3R)-3-(4-benzyloxy-2-methyl-phenyl)-2-ethoxy-3-hydroxy-propionic acid methyl ester (5 g, 14.5 mmol) in trifluoroacetic acid (84 ml) under an argon atmosphere. The mixture was stirred at 0° C. for 30 min and for additional 2 h at ambient temperature. The solution was poured onto crashed ice and extracted with ethyl acetate. The organic layer was washed two times with water and neutralized with saturated aqueous sodium bicarbonate solution. The ethyl acetate layer was washed with brine and dried over sodium sulfate. The solvent was removed under reduced pressure to give a colorless oil which was purified by column chromatography (silica gel, cyclohexane/AcOEt) to yield 2.15 g (6.5 mmol, 45%) of the title compound as colorless oil.

MS: 351.2 (M+Na)$^+$, 346.3 (M+NH$_4$)$^+$, 283.2, 276.2, 223.2, 195.5.

d] (2S)-2-Ethoxy-3-(4-hydroxy-2-methyl-phenyl)-propionic acid methyl ester

A solution of (2S)-3-(4-benzyloxy-2-methyl-phenyl)-2-ethoxy-propionic acid methyl ester (3.6 g, 11 mmol) in methanol (300 ml) was hydrogenated over 10% palladium on charcoal (1 g) at ambient temperature for 2 h. The catalyst was filtered off and the solvent evaporated under reduced pressure to give 2 g (8.4 mmol, 77%) of the title compound as yellow liquid which was used in the next step without further purification.

MS: 261.2 (M+Na)$^+$, 256.1 (M+NH$_4$)$^+$, 239.3 (M+H)$^+$, 193.2, 151.1.

e] 4-Chloromethyl-5-methyl-2-o-tolyl-oxazole

2-Methyl-benzaldehyde (19.3 ml, 166 mmol) was dissolved in acetic acid (175 ml) and treated with diacetyl monooxime (16.8 g, 166 mmol). A stream of dry HCl was bubbled for 2 h at 0° C. and for additional 2 h at ambient temperature through the solution (slightly exothermic). The reaction mixture was poured onto ice water and extracted two times with dichloromethane. The combined extracts were washed with water, saturated aqueous sodium bicarbonate solution (until a pH of 8 was adjusted) and brine. The organic layer was dried over sodium sulfate and the solution was concentrated to a volume of approximately 100 ml under reduced pressure. Chloroform (200 ml) was added and the solution was brought to a volume of approximately 100 ml under reduced pressure. Chloroform (100 ml) was added and the solution of crude 4,5-dimethyl-2-o-tolyl-oxazole 3-oxide was cooled to 0° C. A solution of phosphorous oxychloride (16.7 ml, 183 mmol) in chloroform (175 ml) was added within 10 min. The reaction mixture was heated under reflux for 12 h, cooled to 0° C. and made basic (pH 10) by carefully adding concentrated aqueous NH$_3$ solution. The suspension was poured onto ice water and extracted two times with dichloromethane. The combined extracts were washed with ice water/brine and dried over sodium sulfate. Removal of the solvent under reduced pressure gave a yellow oil which was purified by column chromatography (silica gel, cyclohexane/AcOEt) to yield 29 g (131 mmol, 79%) of the title compound as yellow oil, which solidified upon standing.

MS: 221.1 (M)$^+$, 186.1, 118.0, 89.0, 43.1.

f] (S)-2-Ethoxy-3-[2-methyl-4-(5-methyl-2-o-tolyl-oxazol-4-ylmethoxy)-phenyl]-propionic acid methyl ester A mixture of (S)-2-ethoxy-3-(4-hydroxy-2-methyl-phenyl)-propionic acid methyl ester (80 mg, 0.34 mmol), 4-chloromethyl-5-methyl-2-o-tolyl-oxazole (82 mg, 0.37 mmol), cesium carbonate (120 mg, 0.37 mmol) and a trace of potassium iodide were suspended in acetone (8 ml). The suspension was heated under reflux for 5 h, the solvent evaporated under reduced pressure and the residue dissolved in 2 N HCl/ice water 1/1 and ethyl acetate. The layers were separated and the aqueous layer was extracted two times with ethyl acetate. The combined organic layers were washed two times with brine and dried over sodium sulfate. The solvent was removed under reduced pressure and the residue purified by column chromatography (silica gel, cyclohexane/AcOEt) to give 100 mg (0.24 mmol, 70%) of the title compound as yellow oil.

MS: 446.2 (M+Na)$^+$, 424.3 (M+H)$^+$, 345.1, 269.2, 229.2, 215.4, 186.3.

g] (S)-2-Ethoxy-3-[2-methyl-4-(5-methyl-2-o-tolyl-oxazol-4-ylmethoxy)-phenyl]-propionic acid To a solution of (S)-2-ethoxy-3-[2-methyl-4-(5-methyl-2-o-tolyl-oxazol-4-ylmethoxy)-phenyl]-propionic acid methyl ester (100 mg, 0.24 mmol) in THF/methanol 2/1 (1.5 ml) was added a 1 N aqueous LiOH solution (1.4 ml, 1.4 mmol). The reaction mixture was stirred for 1.5 h at ambient temperature, neutralized with 1 N aqueous HCl solution under ice cooling and concentrated under reduced pressure. The residue was dissolved in 1 N HCl/ice water 1/1 and ethyl acetate, the layers were separated and the aqueous layer was extracted with ethyl acetate. The combined organic layers were washed with ice water/brine 1/1, dried over sodium sulfate and the solvent was evaporated in vacuo to give the title compound (88 mg, 0.21 mmol, 91%) as off-white solid, which was crystalized from dichloromethane/hexane to afford colorless crystals. According to chiral HPLC of the corresponding methyl ester (Chiralcel-ODH), the enantiomeric excess amounts to 98.6%.

MS: 408.5 (M−H)$^-$, 362.3, 305.4, 280.9, 255.1, 216.6.

Example 1a a] 3-(4-Benzyloxy-2-methyl-phenyl)-2-ethoxy-3-hydroxy-propionic acid ethyl ester (mixture of stereoisomers)

To a −78° C. cold 2 M solution of lithium diisopropylamide (305 mmol) in THF/n-heptane (152.4 ml) was added a solution of ethoxy-acetic acid ethyl ester (45.2 ml, 331 mmol) in tetrahydrofuran (240 ml) within 1.5 h under an argon atmosphere. The mixture was stirred for 30 min. A solution of 4-benzyloxy-2-methyl-benzaldehyde (30 g, 132.6 mmol) in tetrahydrofuran (420 ml) was added dropwise over a period of 50 min. The reaction mixture was stirred 2 h at −78° C., poured onto ice water/aqueous ammonium chloride solution 1/1 and extracted two times with ethyl acetate. The combined extracts were washed three times with ice water/brine 1/1 and dried over sodium sulfate. The solvent was removed under reduced pressure and the residue purified by column chromatography (silica gel, n-heptane/AcOEt) to give 48.8 g (136.2 mmol) of the title compound as a mixture of stereoisomers as yellow oil.

MS: 376.4 (M+NH$_4$)$^+$, 341.4, 186.5.

b] (Z)-3-(4-Benzyloxy-2-methyl-phenyl)-2-ethoxy-acrylic acid ethyl ester

To a solution of 3-(4-benzyloxy-2-methyl-phenyl)-2-ethoxy-3-hydroxy-propionic acid ethyl ester (mixture of stereoisomers; 48.8 g, 136.2 mmol) in N,N-dimethylformamid (500 ml) was added sulfuric acid (19.6 ml, 96%). The reaction mixture was heated to 100° C. for 2.5 h, cooled to ambient temperature, poured onto ice water/saturated aqueous NaHCO$_3$ solution 1/1 and extracted two times with ethyl acetate. The combined extracts were washed with ice water/brine 1/1 and dried over sodium sulfate. The solvent was removed under reduced pressure to give 46.1 g (135.4 mmol) of crude (Z)-3-(4-benzyloxy-2-methyl-phenyl)-2-ethoxy-acrylic acid ethyl ester which was used in the next step without further purification.

MS: 358.3 (M+NH$_4$)$^+$, 341.4 (M+H)$^+$, 292.4, 222.4, 187.4.

c] (Z)-2-Ethoxy-3-(4-hydroxy-2-methyl-phenyl)-acrylic acid ethyl ester

To a solution of (Z)-3-(4-benzyloxy-2-methyl-phenyl)-2-ethoxy-acrylic acid ethyl ester (46.1 g, 135.4 mmol) in dichloromethane (500 ml) was added BF3.OEt$_2$ (186 ml, 677 mmol, 46%) and dimethyl sulfide (149 ml, 2.03 mol). The reaction mixture was stirred at ambient temperature for 14 h, poured onto ice water and extracted two times with dichloromethane. The combined extracts were washed with ice water/brine 1/1 and dried over sodium sulfate. The solvent was removed under reduced pressure and the residue purified by column chromatography (silica gel, n-heptane/AcOEt) to give 23.1 g (92.3 mmol, 68% over three steps) of the title compound as yellow crystals.

MS: 248.9 (M+H)$^-$, 219.9.

d] (Z)-2-Ethoxy-3-[2-methyl-4-(5-methyl-2-o-tolyl-oxazol-4-ylmethoxy)-phenyl]-acrylic acid ethyl ester In analogy to the procedure described in example 1 f], (Z)-2-ethoxy-3-(4-hydroxy-2-methyl-phenyl)-acrylic acid ethyl ester was reacted with 4-chloromethyl-5-methyl-2—o— tolyl-oxazole (example 1 f]) in the presence of cesium carbonate and potassium iodide to yield (Z)-2-ethoxy-3-[2-methyl-4-(5-methyl-2-o-tolyl-oxazol-4-ylmethoxy)-phenyl]-acrylic acid ethyl ester as colorless crystals.

MS: 458.4 (M+Na)$^+$, 436.4 (M+H)$^+$, 291.5, 187.5.

e] (Z)-2-Ethoxy-3-[2-methyl-4-(5-methyl-2-o-tolyl-oxazol-4-ylmethoxy)-phenyl]-acrylic acid To a solution of (Z)-2-ethoxy-3-[2-methyl-4-(5-methyl-2-o-tolyl-oxazol-4-ylmethoxy)-phenyl]-acrylic acid ethyl ester (6.8 g, 15.6 mmol) in THF/methanol 2/1 (102 ml) was added a 3 M aqueous NaOH solution (26 ml, 78 mmol). The reaction mixture was stirred for 3 h at ambient temperature, concentrated under reduced pressure, diluted with ice water and acidified with with 1 M aqueous HCl solution. Twofold extraction with ethyl acetate was followed by washing of the combined extracts with ice water/brine 1/1 (three times) and drying of the organic layer over sodium sulfate. The solvent was removed under reduced pressure and the crude product crystallized from dichloromethane/n-heptane to give the title compound (6.3 g, 15.5 mmol, 99%) as colorless crystals.

MS: 406.3 (M−H)$^-$, 334.2, 255.2.

f] (S)-2-Ethoxy-3-[2-methyl-4-(5-methyl-2-o-tolyl-oxazol-4-ylmethoxy)-phenyl]-propionic acid In analogy to the procedure described in example 6a c], (Z)-2-ethoxy-3-[2-methyl-4-(5-methyl-2-o-tolyl-oxazol-4-ylmethoxy)-phenyl]-acrylic acid was hydrogenated for 16 h at 60 bar of hydrogen at 40° C. in dichloromethane/methanol/30% aqueous NaOH solution 1/1/0.04 using [Ru (OAc)$_2$((+)-TMBTP)] catalyst to yield after work-up a black solid with an enantiomeric purity of 93% and a chemical purity of >99% according to HPLC. The crude product was purified by column chromatography (silica gel, n-heptane/ AcOEt/AcOH, two times) to give brown crystals which were recrystallized from ethyl acetate to afford the title compound as off-white crystals. According to chiral HPLC (Chiralcel-ODH column, 25 cm×4.6 mm, 97% heptane/3% iso-propanol with 0.15% trifluoroacetic acid, flow at 0.8 ml/min, 25° C., 274 nm. Retention times: R-acid 19.3 min, S-acid 21.6 min, α,β-unsaturated Z-acid 28.2 min), the enantiomeric excess amounts to 99.8%.

MS: 408.3 (M–H)$^-$, 362.2.

Example 2 a] 2-(4-Isopropoxy-phenyl)-4,5-dimethyl-oxazole 3-oxide; hydrochloride

Into a suspension of diacetyl monooxime (1 g, 9.9 mmol) and 4-isopropoxy-benzaldehyde (1.6 g, 9.9 mmol) in acetic acid (10 ml), dry hydrogen chloride was bubbled for 30 min under ice-cooling and for additional 45 min at ambient temperature. The reaction mixture was cooled to 0° C., diethyl ether (25 ml) was added within 5 min and the formed precipitate was filtered off and washed with ice-cold diethyl ether to yield the title compound (2.5 g, 8.8 mmol, 89%) as colorless crystals.

MS: 247.2 (M–HCl)$^+$, 205.1, 188.1, 121.2, 93.2, 43.3.

b] 4-Chloromethyl-2-(4-isopropoxy-phenyl)-5-methyl-oxazole

To a solution of 2-(4-isopropoxy-phenyl)-4,5-dimethyl-oxazole 3-oxide; hydrochloride (2.5 g, 8.8 mmol) in chloroform (12 ml) was added a solution of phosphorous oxychloride (1 ml, 11 mmol) in chloroform (12 ml) within 5 min. The reaction mixture was heated under reflux for 45 min, cooled to 0° C. and made basic (pH 10) by carefully adding concentrated aqueous NH$_3$ solution. The suspension was poured onto ice water and extracted two times with dichloromethane. The combined extracts were washed with ice water/brine and dried over sodium sulfate. Removal of the solvent under reduced pressure gave a brown oil which was purified by column chromatography (silica gel, dichloromethane) to yield 1.6 g (6 mmol, 60%) of the title compound as colorless oil.

MS: 266.3 (M+H)$^+$, 224.2, 188.3.

c] (S)-2-Ethoxy-3-{4-[2-(4-isopropoxy-phenyl)-5-methyl-oxazol-4-ylmethoxy]-2-methyl-phenyl}-propionic acid methyl ester In analogy to the procedure described in example 1 f], (2S)-2-ethoxy-3-(4-hydroxy-2-methyl-phenyl)-propionic acid methyl ester (example 1 d]) was reacted with 4-chloromethyl-2-(4-isopropoxy-phenyl)-5-methyl-oxazole in the presence of cesium carbonate and potassium iodide to yield (S)-2-ethoxy-3-{4-[2-(4-isopropoxy-phenyl)-5-methyl-oxazol-4-ylmethoxy]-2-methyl-phenyl}-propionic acid methyl ester as colorless liquid.

MS: 490.2 (M+Na)$^+$, 468.2 (M+H)$^+$, 269.2, 230.2, 188.3.

d] (S)-2-Ethoxy-3-{4-[2-(4-isopropoxy-phenyl)-5-methyl-oxazol-4-ylmethoxy]-2-methyl-phenyl}-propionic acid In analogy to the procedure described in example 1 g], (S)-2-ethoxy-3-{4-[2-(4-isopropoxy-phenyl)-5-methyl-oxazol-4-ylmethoxy]-2-methyl-phenyl}-propionic acid methyl ester was treated with LiOH to obtain (S)-2-ethoxy-3-{4-[2-(4-isopropoxy-phenyl)-5-methyl-oxazol-4-ylmethoxy]-2-methyl-phenyl}-propionic acid as colorless solid.

MS: 452.3 (M–H)$^-$, 343.0, 283.3, 246.8, 218.7.

Example 3 a] (S)-2-Ethoxy-3-[2-methyl-4-(5-methyl-2-phenyl-oxazol-4-ylmethoxy)-phenyl]-propionic acid methyl ester In analogy to the procedure described in example 1 f], (2S)-2-ethoxy-3-(4-hydroxy-2-methyl-phenyl)-propionic acid methyl ester (example 1 d]) was reacted with 4-chloromethyl-5-methyl-2-phenyl-oxazole in the presence of cesium carbonate and potassium iodide to yield (S)-2-ethoxy-3-[2-methyl-4-(5-methyl-2-phenyl-oxazol-4-ylmethoxy)-phenyl]-propionic acid methyl ester as colorless liquid.

MS: 432.3 (M+Na)$^+$, 410.3 (M+H)$^+$, 293.2, 269.2, 187.2, 172.2.

b] (S)-2-Ethoxy-3-[2-methyl-4-(5-methyl-2-phenyl-oxazol-4-ylmethoxy)-phenyl]-propionic acid In analogy to the procedure described in example 1 g], (S)-2-ethoxy-3-[2-methyl-4-(5-methyl-2-phenyl-oxazol-4-ylmethoxy)-phenyl]-propionic acid methyl ester was treated with LiOH to obtain (S)-2-ethoxy-3-[2-methyl-4-(5-methyl-2-phenyl-oxazol-4-ylmethoxy)-phenyl]-propionic acid as colorless solid, which was crystalized from hexane/dichloromethane to afford colorless crystals. According to chiral HPLC of the corresponding methyl ester (Chiralcel-OJ), the enantiomeric excess amounts to 99.0%.

MS: 394.2 (M–H)$^-$, 348.2, 293.2, 223.1.

Example 3a a] (Z)-2-Ethoxy-3-[2-methyl-4-(5-methyl-2-phenyl-oxazol-4-ylmethoxy)-phenyl]-acrylic acid ethyl ester In analogy to the procedure described in example 1 f], (Z)-2-ethoxy-3-(4-hydroxy-2-methyl-phenyl)-acrylic acid ethyl ester (example 1a c]) was reacted with 4-chloromethyl-5-methyl-2-phenyl-oxazole (example 3 a]) in the presence of cesium carbonate and potassium iodide to yield (Z)-2-ethoxy-3-[2-methyl-4-(5-methyl-2-phenyl-oxazol-4-ylmethoxy)-phenyl]-acrylic acid ethyl ester as colorless solid.

MS: 444.3 (M+Na)$^+$, 422.5 (M+H)$^+$, 267.5, 213.5.

b] (Z)-2-Ethoxy-3-[2-methyl-4-(5-methyl-2-phenyl-oxazol-4-ylmethoxy)-phenyl]-acrylic acid In analogy to the procedure described in example 1a f], (Z)-2-ethoxy-3-[2-methyl-4-(5-methyl-2-phenyl-oxazol-4-ylmethoxy)-phenyl]-acrylic acid ethyl ester was treated with NaOH to obtain (Z)-2-ethoxy-3-[2-methyl-4-(5-methyl-2-phenyl-oxazol-4-ylmethoxy)-phenyl]-acrylic acid as colorless solid.

MS: 394.3 (M+H)$^+$, 279.3, 249.3.

c] (S)-2-Ethoxy-3-[2-methyl-4-(5-methyl-2-phenyl-oxazol-4-ylmethoxy)-phenyl]-propionic acid In analogy to the procedure described in example 6a c], (Z)-2-ethoxy-3-[2-methyl-4-(5-methyl-2-phenyl-oxazol-4- ylmethoxy)-phenyl]-acrylic acid was hydrogenated in a 35 ml autoclave for 16 h at a hydrogen pressure of 60 bar at 40° C. in dichloromethane/methanol/30% aqueous NaOH solution 1/1/0.03 using [Ru(OAc)$_2$((+)-TMBTP)] catalyst to yield after work-up a black solid with an enantiomeric purity of 93% and a chemical purity of >99% according to HPLC. The crude product was purified by column chromatography (silica gel, n-heptane/AcOEt/AcOH, two times) to give brown crystals which were recrystallized from ethyl acetate to afford the title compound as colorless crystals. According to chiral HPLC (Chiralcel-OJH column, 25 cm×4.6 mm, 80% heptane/20% ethanol with 1.5% trifluoroacetic acid, flow at 0.8 ml/min, 25° C., 275 nm. Retention times: R-acid 26.4 min, S-acid 29.1 min, α,β-unsaturated Z-acid 32.6 min), the enantiomeric excess amounts to 99.2%.

MS: 394.2 (M−H)$^-$, 348.2.

Example 4 a] (S)-3-{4-[2-(3,5-Dimethoxy-phenyl)-5-methyl-oxazol-4-ylmethoxy]-2-methyl-phenyl}-2-ethoxy-propionic acid methyl ester In analogy to the procedure described in example 1 f], (2S)-2-ethoxy-3-(4-hydroxy-2-methyl-phenyl)-propionic acid methyl ester (example 1 d]) was reacted with 4-chloromethyl-2-(3,5-dimethoxy-phenyl)-5-methyl-oxazole (prepared from 3,5-dimethoxy-benzaldehyde and diacetyl monoxyme followed by treatment with POCl$_3$ in analogy to the procedures described in examples 2 a] and b]) in the presence of cesium carbonate and potassium iodide to yield (S)-3-{4-[2-(3,5-dimethoxy-phenyl)-5-methyl-oxazol-4-ylmethoxy]-2-methyl-phenyl}-2-ethoxy-propionic acid methyl ester as colorless liquid.

MS: 492.2 (M+Na)$^+$, 470.1 (M+H)$^+$, 273.2, 232.1, 205.2, 164.2.

b] (S)-3-{4-[2-(3,5-Dimethoxy-phenyl)-5-methyl-oxazol-4-ylmethoxy]-2-methyl-phenyl}-2-ethoxy-propionic acid In analogy to the procedure described in example 1 g], (S)-3-{4-[2-(3,5-dimethoxy-phenyl)-5-methyl-oxazol-4-ylmethoxy]-2-methyl-phenyl}-2-ethoxy-propionic acid methyl ester was treated with LiOH to obtain (S)-3-{4-[2-(3,5-dimethoxy-phenyl)-5-methyl-oxazol-4-ylmethoxy]-2-methyl-phenyl}-2-ethoxy-propionic acid as colorless solid.

MS: 454.3 (M−H)$^-$, 408.2, 364.1, 305.0, 255.0, 223.1.

Example 5 a] 2-(4-Fluoro-3-methyl-phenyl)-4,5-dimethyl-oxazole 3-oxide

Into a suspension of diacetyl monooxime (11 g, 108.6 mmol) and 4-fluoro-3-methyl-benzaldehyde (15 g, 108.6 mmol) in acetic acid (100 ml), dry hydrogen chloride was bubbled for 30 min under ice-cooling and for additional 45 min at ambient temperature. The reaction mixture was poured onto ice water and extracted two times with ethyl acetate. The combined extracts were washed with ice water, saturated aqueous sodium bicarbonate solution (until a pH of 8 was adjusted) and brine. The organic layer was dried over sodium sulfate and the solvent removed under reduced pressure to afford the title compound (12.3 g, 55.6 mmol, 51%) as yellow crystals.

MS: 222.1 (M+H)$^+$, 205.1, 176.1, 137.1, 109.1.

b] 4-Chloromethyl-2-(4-fluoro-3-methyl-phenyl)-5-methyl-oxazole

In analogy to the procedure described in example 2 b], 2-(4-fluoro-3-methyl-phenyl)-4,5-dimethyl-oxazole 3-oxide was treated with phosphorous oxychloride in chloroform to yield 4-chloromethyl-2-(4-fluoro-3-methyl-phenyl)-5-methyl-oxazole as colorless solid.

MS: 239.0 (M)$^+$, 204.1, 136.1, 43.2.

c] (S)-2-Ethoxy-3-{4-[2-(4-fluoro-3-methyl-phenyl)-5-methyl-oxazol-4-ylmethoxy]-2-methyl-phenyl}-propionic acid methyl ester In analogy to the procedure described in example 1 f], (2S)-2-ethoxy-3-(4-hydroxy-2-methyl-phenyl)-propionic acid methyl ester (example 1 d]) was reacted with 4-chloromethyl-2-(4-fluoro-3-methyl-phenyl)-5-methyl-oxazole in the presence of cesium carbonate and potassium iodide to yield (S)-2-ethoxy-3-{4-[2-(4-fluoro-3-methyl-phenyl)-5-methyl-oxazol-4-ylmethoxy]-2-methyl-phenyl}-propionic acid methyl ester as colorless liquid.

MS: 464.2 (M+Na)$^+$, 442.2 (M+H)$^+$, 349.1, 317.0, 280.2, 245.2, 204.1.

d] (S)-2-Ethoxy-3-{4-[2-(4-fluoro-3-methyl-phenyl)-5-methyl-oxazol-4-ylmethoxy]-2-methyl-phenyl}-propionic acid In analogy to the procedure described in example 1 g], (S)-2-ethoxy-3-{4-[2-(4-fluoro-3-methyl-phenyl)-5-methyl-oxazol-4-ylmethoxy]-2-methyl-phenyl}-propionic acid methyl ester was treated with LiOH to obtain (S)-2-ethoxy-3-{4-[2-(4-fluoro-3-methyl-phenyl)-5-methyl-oxazol-4-ylmethoxy]-2-methyl-phenyl}-propionic acid as colorless solid.

MS: 426.1 (M−H)$^-$, 348.4, 263.2, 174.8.

Example 6 a] (S)-2-Ethoxy-3-{4-[2-(2-fluoro-phenyl)-5-methyl-oxazol-4-ylmethoxy]-2-methyl-phenyl}-propionic acid methyl ester In analogy to the procedure described in example 1 f], (2S)-2-ethoxy-3-(4-hydroxy-2-methyl-phenyl)-propionic acid methyl ester (example 1 d]) was reacted with 4-chloromethyl-2-(2-fluoro-phenyl)-5-methyl-oxazole (prepared from 2-fluoro-benzaldehyde and diacetyl monoxyme followed by treatment with POCl$_3$ in analogy to the procedures described in examples 5 a] and 2 b]) in the presence of cesium carbonate and potassium iodide to yield (S)-2-ethoxy-3-{4-[2-(2-fluoro-phenyl)-5-methyl-oxazol-4-ylmethoxy]-2-methyl-phenyl}-propionic acid methyl ester as colorless liquid.

MS: 450.2 (M+Na)$^+$, 428.3 (M+H)$^+$, 368.0, 231.2, 190.3.

b] (S)-2-Ethoxy-3-{4-[2-(2-fluoro-phenyl)-5-methyl-oxazol-4-ylmethoxy]-2-methyl-phenyl}-propionic acid In analogy to the procedure described in example 1 g], (S)-2-ethoxy-3-{4-[2-(2-fluoro-phenyl)-5-methyl-oxazol-4-ylmethoxy]-2-methyl-phenyl}-propionic acid methyl ester was treated with LiOH to obtain (S)-2-ethoxy-3-{4-[2-(2-fluoro-phenyl)-5-methyl-oxazol-4-ylmethoxy]-2-methyl-phenyl}-propionic acid as colorless solid, which was crystalized from hexane/dichloromethane to afford colorless crystals. According to chiral HPLC of the corresponding methyl ester (Chiralcel-ODH), the enantiomeric excess amounts to 99.4%.

MS: 412.3 (M−H)⁻, 366.5, 278.4, 254.9, 223.1.

Example 6a a] (Z)-2-Ethoxy-3-{4-[2-(2-fluoro-phenyl)-5-methyl-oxazol-4-ylmethoxy]-2-methyl-phenyl}-acrylic acid ethyl ester In analogy to the procedure described in example 1 f], (Z)-2-ethoxy-3-(4-hydroxy-2-methyl-phenyl)-acrylic acid ethyl ester (example 1a c]) was reacted with 4-chloromethyl-2-(2-fluoro-phenyl)-5-methyl-oxazole (example 6 a]) in the presence of cesium carbonate and potassium iodide to yield (Z)-2-ethoxy-3-{4-[2-(2-fluoro-phenyl)-5-methyl-oxazol-4-ylmethoxy]-2-methyl-phenyl}-acrylic acid ethyl ester as colorless crystals.

MS: 462.4 (M+Na)⁺, 440.4 (M+H)⁺, 206.4.

b] (Z)-2-Ethoxy-3-{4-[2-(2-fluoro-phenyl)-5-methyl-oxazol-4-ylmethoxy]-2-methyl-phenyl}-acrylic acid In analogy to the procedure described in example 1a f], (Z)-2-ethoxy-3-{4-[2-(2-fluoro-phenyl)-5-methyl-oxazol-4-ylmethoxy]-2-methyl-phenyl}-acrylic acid ethyl ester was treated with NaOH to obtain (Z)-2-ethoxy-3-{4-[2-(2-fluoro-phenyl)-5-methyl-oxazol-4-ylmethoxy]-2-methyl-phenyl}-acrylic acid as colorless solid.

MS: 412.4 (M+H)⁺.

c] (S)-2-Ethoxy-3-{4-[2-(2-fluoro-phenyl)-5-methyl-oxazol-4-ylmethoxy]-2-methyl-phenyl}-propionic acid In a glove box (O₂ content≦2 ppm), a 185 ml stainless steel autoclave was charged with 11.5 g of (Z)-2-ethoxy-3-{4-[2-(2-fluoro-phenyl)-5-methyl-oxazol-4-ylmethoxy]-2-methyl-phenyl}-acrylic acid (28.0 mmol), 35 ml of dichloromethane, 35 ml of methanol, 2.5 ml of a 30% aqueous NaOH solution (14.0 mmol) and 22.6 mg (0.028 mmol) of [Ru(OAc)₂((+)-TMBTP)]. TMBTP is 4,4'-Bis(diphenylphosphino)-2,2',5,5'-tetramethyl-3,3'-dithiophene, its synthesis as (R) or (S) enantiomer is described in WO 96/01831 appl to Italfarmaco Sud and in T. Benincori et al, *J. Org. Chem.* 2000, 65, 2043. The complex [Ru(OAc)₂((+)-TMBTP)] has been synthesized in analogy to a general procedure reported in N. Feiken et al, *Organometallics* 1997, 16, 537, ³¹P-NMR (CDCl₃): δ1.4 ppm (s). The autoclave was sealed and the hydrogenation was run under stirring at 40° C. under 60 bar of hydrogen. After 16 h the autoclave was opened and the yellow-brown solution was rotary evaporated to dryness (50° C./5 mbar). The residue was dissolved in 60 ml of ethyl acetate, 60 ml of water and 3 ml of aqueous hydrochloric acid (25%). The organic layer was separated and evaporated to dryness (50° C./5 mbar) to afford 12 g of crude product as a solid with an enantiomeric purity of 92% and a chemical purity of >99% according to HPLC. The crude product was dissolved in dichloromethane, (S)-phenylethylamine (4.12 ml, 31.1 mmol) was added and the solvent removed under reduced pressure. The brown residue was crystallized from ethyl acetate to obtain colorless crystals which were suspended in ice water/ethyl acetate 1/1. The pH of the suspension was adjusted to 1 with 1 M aqueous hydrochloric acid, the layers were separated and the aqueous layer extracted two more times with ethyl acetate. The combined extracts were washed with ice water/brine 1/1, dried over sodium sulfate and the solvent removed in vacuo to obtain colorless crystals which were recrystallized from ethyl acetate to afford 8.45 g (20.4 mmol, 73%) of the title compound as colorless crystals. According to chiral HPLC (Chiralcel-ODH column, 25 cm×4.6 mm, 97% heptane/3% iso-propanol with 0.15% trifluoroacetic acid, flow at 0.7 ml/min, 25° C., 274 nm. Retention times: R-acid 30.2 min, S-acid 32.8 min, α,β-unsaturated Z-acid 39.1 min), the enantiomeric excess amounts to 100%.

MS: 412.0 (M−H)⁻.

Example 7 a] (S)-4-Benzyl-3-[(2S)-3-(4-benzyloxy-2-methyl-phenyl)-2-ethoxy-propionyl]-oxazolidin-2-one In analogy to the procedure described in example 1 c], (S)-4-benzyl-3-[(2S,3R)-3-(4-benzyloxy-2-methyl-phenyl)-2-ethoxy-3-hydroxy-propionyl]-oxazolidin-2-one (example 1 a]) was treated with triethylsilane in trifluoroacetic acid to yield the title compound as colorless liquid.

MS: 496.2 (M+Na)⁺, 491.3 (M+NH₄)⁺, 474.2 (M+H)⁺, 428.3, 352.3, 251.2, 175.2.

b] (S)-4-Benzyl-3-[(2S)-2-ethoxy-3-(4-hydroxy-2-methyl-phenyl)-propionyl]-oxazolidin-2-one In analogy to the procedure described in example 1 d], (S)-4-benzyl-3-[(2S)-3-(4-benzyloxy-2-methyl-phenyl)-2-ethoxy-propionyl]-oxazolidin-2-one was hydrogenated over 10% palladium on charcoal to give the title compound as yellow liquid.

MS: 382.1 (M−H)⁻, 324.9, 305.1, 282.9, 261.8, 255.2, 221.4, 175.6.

c] (S)-4-Benzyl-3-[(2S)-3-(4-{2-[2-(4-chloro-phenyl)-5-methyl-oxazol-4-yl]-ethoxy}-2-methyl-phenyl)-2-ethoxy-propionyl]-oxazolidin-2-one To a ice cold solution of (S)-4-benzyl-3-[(2S)-2-ethoxy-3-(4-hydroxy-2-methyl-phenyl)-propionyl]-oxazolidin-2-one (100 mg, 260 µmol), 2-[2-(4-chloro-phenyl)-5-methyl-oxazol-4-yl]-ethanol (93 mg, 390 µmol) (prepared from methyl 3-oxopentanoate and 4-chloro-benzamide in analogy to the sequence described for the synthesis of 2-(5-methyl-2-phenyl-oxazol-4-yl)-ethanol in M. Scalone, PCT WO 01/79202 A1) and triphenylphosphine (103 mg, 390 mmol) in tetrahydrofuran (2.5 ml) was added diethyl azodicarboxylate (61 µl, 390 µmol). The cooling bath was removed and stirring was continued for 12 h. Evaporation of the solvent under reduced pressure gave a yellow oil which was purified by column chromatography (silica gel, cyclohexane/AcOEt) to give 70 mg (120 µmol, 45%) of the title compound as colorless oil.

MS: 626.3 (M+Na)⁺, 603.2 (M)⁺, 557.2, 479.3, 381.2, 351.1, 273.2, 187.2.

d] (S)-3-(4-{2-[2-(4-Chloro-phenyl)-5-methyl-oxazol-4-yl]-ethoxy}-2-methyl-phenyl)-2-ethoxy-propionic acid (S)-4-Benzyl-3-[(2S)-3-(4-{2-[2-(4-chloro-phenyl)-5-methyl-oxazol-4-yl]-ethoxy}-2-methyl-phenyl)-2-ethoxy-propionyl]-oxazolidin-2-one (70 mg, 120 µmol) was dissolved in ice-cooled THF (0.7 ml) and treated with 1 N NaOH (0.3 ml, 300 mmol) at 0° C. for 2 h. The reaction mixture was poured onto ice water, extracted two times with diethyl ether and the combined organic layers were washed with ice water. The combined aqueous layers were acidified with 1 N HCl and extracted two times with ethyl acetate. The combined extracts were washed with brine and dried over sodium sulfate. Evaporation of the solvent gave 47 mg (110 mmol, 91%) of the title compound as yellow liquid.

MS: 442.1 (M–H)⁻, 396.1, 362.0, 223.6, 176.4.

Example 8 a] 1-Ethyl-3-(phenylmethoxy)-benzene

To a suspension of potassium carbonate (17 g, 123 mmol) in N,N-dimethylformamide (40 ml) was added a solution of 3-ethyl-phenol (14.8 ml, 123 mmol) in N,N-dimethylformamide (40 ml) at 2° C. under an argon atmosphere. After stirring for 50 min at 2° C., benzyl bromide (14.6 ml, 123 mmol) was added over a period of 15 min at 2° C. The suspension was stirred for additional 30 min at 2° C. and for 12 h at ambient temperature. After adding ice water (250 ml), the solution was extracted two times with diethyl ether. The combined extracts were washed two times with brine and dried over sodium sulfate. Evaporation of the solvent gave a yellow oil which was purified by column chromatography (silica gel, cyclohexane) to yield 24.3 g (114 mmol, 93%) of the title compound as yellow liquid.

MS: 212.2 (M+H)⁺, 183.1, 91.2, 65.1.

b] 1-Bromo-2-ethyl-4-(phenylmethoxy)-benzene

To a solution of 1-ethyl-3-(phenylmethoxy)-benzene (15 g, 71 mmol) in THF (200 ml) were added N-bromosuccinimide (16.3 g, 92 mmol) and concentrated sulfuric acid (2.4 ml). The solution was stirred for 5 h at ambient temperature. Sodium bicarbonate (3.6 g) and 10% aqueous NaHSO₃ solution (400 ml) were added under ice cooling. The resulting mixture was stirred for 10 min and then poured into ethyl acetate. The phases were separated and the aqueous phase was extracted with ethyl acetate. The combined extracts were washed with ice water and brine and dried over sodium sulfate. Removal of the solvent under reduced pressure gave a yellow oil which was purified by column chromatography (silica gel, cyclohexane) to yield 17.1 g (58.7 mmol, 83%) of the title compound as colorless liquid.

MS: 292.0 (M)⁺, 290.0 (M)⁺, 212.2, 91.1, 65.2.

c] 4-Benzyloxy-2-ethyl-benzaldehyde

A 1.6 M solution of n-BuLi in hexane (44.4 ml, 69.9 mmol) was added within 10 min to a stirred cooled (–85° C.) solution of 1-bromo-2-ethyl-4-(phenylmethoxy)-benzene (18.5 g, 63.5 mmol) in dry THF (22 ml). The mixture was stirred for 1 h at –85° C. under an argon atmosphere. N,N-Dimethylformamide (25.5 ml, 330.4 mmol) was added and the temperature was allowed to rise slowly to room temperature. An aqueous saturated NH₄Cl solution (70 ml) was added under ice cooling. The mixture was extracted two times with dichloromethane, the combined extracts were washed with brine and dried over sodium sulfate. Removal of the solvent under reduced pressure gave a yellow oil which was purified by column chromatography (silica gel, cyclohexane/AcOEt) to yield 11.9 g (49.5 mmol, 78%) of the title compound as yellow oil.

MS: 240.1 (M+H)⁺, 91.1, 77.1, 65.2.

d] (S)-4-Benzyl-3-[(2S,3R)-3-(4-benzyloxy-2-ethyl-phenyl)-2-ethoxy-3-hydroxy-propionyl]-oxazolidin-2-one In analogy to the procedure described in example 1 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, *Tetrahedron: Asymmetry* 1999, 10, 1353-1367) was reacted with 4-benzyloxy-2-ethyl-benzaldehyde in the presence of triethylamine and di-n-butyl-boron triflate to give (S)-4-benzyl-3-[(2S,3R)-3-(4-benzyloxy-2-ethyl-phenyl)-2-ethoxy-3-hydroxy-propionyl]-oxazolidin-2-one as yellow foam. According to ¹H-NMR spectroscopy, one of the four isomers is strongly predominating. The configuration was tentatively assigned as 2S,3R according to D. Haigh et al., *Tetrahedron: Asymmetry* 1999, 10, 1353-1367.

MS: 526.3 (M+Na)⁺, 521.3 (M+NH₄)⁺, 486.2, 381.2, 309.2, 281.2, 253.3, 178.1.

e] (2S,3R)-3-(4-Benzyloxy-2-ethyl-phenyl)-2-ethoxy-3-hydroxy-propionic acid methyl ester In analogy to the procedure described in example 1 b], (S)-4-benzyl-3-[(2S,3R)-3-(4-benzyloxy-2-ethyl-phenyl)-2-ethoxy-3-hydroxy-propionyl]-oxazolidin-2-one was treated with sodium methoxide in methanol to give (2S,3R)-3-(4-benzyloxy-2-ethyl-phenyl)-2-ethoxy-3-hydroxy-propionic acid methyl ester as colorless liquid. According to ¹H-NMR spectroscopy, one single diastereomer was obtained.

MS: 381.2 (M+Na)⁺, 376.3 (M+NH₄)⁺, 341.3, 295.3, 253.2, 225.3.

f] (2S)-3-(4-Benzyloxy-2-ethyl-phenyl)-2-ethoxy-propionic acid methyl ester

In analogy to the procedure described in example 1 c], (2S,3R)-3-(4-benzyloxy-2-ethyl-phenyl)-2-ethoxy-3-hydroxy-propionic acid methyl ester was treated with triethylsilane in trifluoroacetic acid to yield (2S)-3-(4-benzyloxy-2-ethyl-phenyl)-2-ethoxy-propionic acid methyl ester as colorless liquid.

MS: 365.2 (M+Na)⁺, 360.2 (M+NH₄)⁺, 297.3, 283.2, 237.2, 209.3, 181.2.

g] (2S)-2-Ethoxy-3-(2-ethyl-4-hydroxy-phenyl)-propionic acid methyl ester

In analogy to the procedure described in example 1 d], (2S)-3-(4-benzyloxy-2-ethyl-phenyl)-2-ethoxy-propionic acid methyl ester was hydrogenated over 10% palladium on charcoal to give (2S)-2-ethoxy-3-(2-ethyl-4-hydroxy-phenyl)-propionic acid methyl ester as colorless liquid.

MS: 275.2 (M+Na)⁺, 270.3 (M+NH₄)⁺, 253.3 (M+H)⁺, 207.2, 175.2, 165.3, 147.2.

h] (S)-2-Ethoxy-3-[2-ethyl-4-(5-methyl-2-phenyl-oxazol-4-ylmethoxy)-phenyl]-propionic acid methyl ester In analogy to the procedure described in example 1 f], (2S)-2-ethoxy-3-(2-ethyl-4-hydroxy-phenyl)-propionic acid methyl ester was reacted with 4-chloromethyl-5-methyl-2-phenyl-oxazole in the presence of cesium carbonate and potassium iodide to yield (S)-2-ethoxy-3-[2-ethyl-4-(5-methyl-2-phenyl-oxazol-4-ylmethoxy)-phenyl]-propionic acid methyl ester as colorless liquid.

MS: 446.3 (M+Na)$^+$, 424.3 (M+H)$^+$, 378.3, 213.3, 172.3.

i] (S)-2-Ethoxy-3-[2-ethyl-4-(5-methyl-2-phenyl-oxazol-4-ylmethoxy)-phenyl]-propionic acid In analogy to the procedure described in example 1 g], (S)-2-ethoxy-3-[2-ethyl-4-(5-methyl-2-phenyl-oxazol-4-ylmethoxy)-phenyl]-propionic acid methyl ester was treated with LiOH to obtain (S)-2-ethoxy-3-[2-ethyl-4-(5-methyl-2-phenyl-oxazol-4-ylmethoxy)-phenyl]-propionic acid as colorless foam.

MS: 408.2 (M−H)$^-$, 362.0, 318.2, 236.7, 190.0.

Example 9 a] (S)-2-Ethoxy-3-{2-ethyl-4-[2-(4-fluoro-3-methyl-phenyl)-5-methyl-oxazol-4-ylmethoxy]-phenyl}-propionic acid methyl ester In analogy to the procedure described in example 1 f], (2S)-2-ethoxy-3-(2-ethyl-4-hydroxy-phenyl)-propionic acid methyl ester (example 8 g]) was reacted with 4-chloromethyl-2-(4-fluoro-3-methyl-phenyl)-5-methyl-oxazole (example 5 b]) in the presence of cesium carbonate and potassium iodide to yield (S)-2-ethoxy-3-{2-ethyl-4-[2-(4-fluoro-3-methyl-phenyl)-5-methyl-oxazol-4-ylmethoxy]-phenyl}-propionic acid methyl ester as colorless liquid.

MS: 478.3 (M+Na)$^+$, 456.3 (M+H)$^+$, 371.3, 271.3, 245.3, 204.2.

b] (S)-2-Ethoxy-3-{2-ethyl-4-[2-(4-fluoro-3-methyl-phenyl)-5-methyl-oxazol-4-ylmethoxy]-phenyl}-propionic acid In analogy to the procedure described in example 1 g], (S)-2-ethoxy-3-{2-ethyl-4-[2-(4-fluoro-3-methyl-phenyl)-5-methyl-oxazol-4-ylmethoxy]-phenyl}-propionic acid methyl ester was treated with LiOH to obtain (S)-2-ethoxy-3-{2-ethyl-4-[2-(4-fluoro-3-methyl-phenyl)-5-methyl-oxazol-4-ylmethoxy]-phenyl}-propionic acid as colorless solid.

MS: 440.3 (M−H)$^-$, 393.9, 350.1, 255.2, 237.4, 203.6.

Example 10 a] (S)-2-Ethoxy-3-{2-ethyl-4-[2-(2-fluoro-phenyl)-5-methyl-oxazol-4-ylmethoxy]-phenyl}-propionic acid methyl ester In analogy to the procedure described in example 1 f], (2S)-2-ethoxy-3-(2-ethyl-4-hydroxy-phenyl)-propionic acid methyl ester (example 8 g]) was reacted with 4-chloromethyl-2-(2-fluoro-phenyl)-5-methyl-oxazole (prepared from 2-fluoro-benzaldehyde and diacetyl monoxyme followed by treatment with POCl$_3$ in analogy to the procedures described in examples 5 a] and 2 b]) in the presence of cesium carbonate and potassium iodide to yield (S)-2-ethoxy-3-{2-ethyl-4-[2-(2-fluoro-phenyl)-5-methyl-oxazol-4-ylmethoxy]-phenyl}-propionic acid methyl ester as colorless liquid.

MS: 464.2 (M+Na)$^+$, 459.3 (M+NH$_4$)$^+$, 442.2 (M+H)$^+$, 396.2, 231.2, 190.3.

b] (S)-2-Ethoxy-3-{2-ethyl-4-[2-(2-fluoro-phenyl)-5-methyl-oxazol-4-ylmethoxy]-phenyl}-propionic acid In analogy to the procedure described in example 1 g], (S)-2-ethoxy-3-{2-ethyl-4-[2-(2-fluoro-phenyl)-5-methyl-oxazol-4-ylmethoxy]-phenyl}-propionic acid methyl ester was treated with LiOH to obtain (S)-2-ethoxy-3-{2-ethyl-4-[2-(2-fluoro-phenyl)-5-methyl-oxazol-4-ylmethoxy]-phenyl}-propionic acid as colorless liquid.

MS: 450.2 (M+Na)$^+$, 428.3 (M+H)$^+$, 382.2, 231.2, 190.3.

Example 11 a] (S)-2-Ethoxy-3-[2-ethyl-4-(5-methyl-2-o-tolyl-oxazol-4-ylmethoxy)-phenyl]-propionic acid methyl ester In analogy to the procedure described in example 1 f], (2S)-2-ethoxy-3-(2-ethyl-4-hydroxy-phenyl)-propionic acid methyl ester (example 8 g]) was reacted with 4-chloromethyl-5-methyl-2-o-tolyl-oxazole (example 1 e]) in the presence of cesium carbonate and potassium iodide to yield (S)-2-ethoxy-3-[2-ethyl-4-(5-methyl-2-o-tolyl-oxazol-4-ylmethoxy)-phenyl]-propionic acid methyl ester as colorless liquid.

MS: 460.2 (M+Na)$^+$, 438.3 (M+H)$^+$, 407.2, 227.2, 186.3.

b] (S)-2-Ethoxy-3-[2-ethyl-4-(5-methyl-2-o-tolyl-oxazol-4-ylmethoxy)-phenyl]-propionic acid In analogy to the procedure described in example 1 g], (S)-2-ethoxy-3-[2-ethyl-4-(5-methyl-2-o-tolyl-oxazol-4-ylmethoxy)-phenyl]-propionic acid methyl ester was treated with LiOH to obtain (S)-2-ethoxy-3-[2-ethyl-4-(5-methyl-2-o-tolyl-oxazol-4-ylmethoxy)-phenyl]-propionic acid as colorless liquid.

MS: 446.2 (M+Na)$^+$, 424.3 (M+H)$^+$, 372.4, 230.2, 186.3.

Example 12 a] (S)-2-Ethoxy-3-{2-ethyl-4-[2-(4-isopropoxy-phenyl)-5-methyl-oxazol-4-ylmethoxy]-phenyl}-propionic acid methyl ester In analogy to the procedure described in example 1 f], (2S)-2-ethoxy-3-(2-ethyl-4-hydroxy-phenyl)-propionic acid methyl ester (example 8 g]) was reacted with 4-chloromethyl-2-(4-isopropoxy-phenyl)-5-methyl-oxazole (example 2 b]) in the presence of cesium carbonate and potassium iodide to yield (S)-2-ethoxy-3-{2-ethyl-4-[2-(4-isopropoxy-phenyl)-5-methyl-oxazol-4-ylmethoxy]-phenyl}-propionic acid methyl ester as colorless liquid.

MS: 504.4 (M+Na)$^+$, 482.4 (M+H)$^+$, 271.2, 230.2, 188.3.

b] (S)-2-Ethoxy-3-{2-ethyl-4-[2-(4-isopropoxy-phenyl)-5-methyl-oxazol-4-ylmethoxy]-phenyl}-propionic acid In analogy to the procedure described in example 1 g], (S)-2-ethoxy-3-{2-ethyl-4-[2-(4-isopropoxy-phenyl)-5-methyl-oxazol-4-ylmethoxy]-phenyl}-propionic acid methyl ester was treated with LiOH to obtain (S)-2-ethoxy-3-{2-ethyl-4-[2-(4-isopropoxy-phenyl)-5-methyl-oxazol-4-ylmethoxy]-phenyl}-propionic acid as colorless liquid.

MS: 490.2 (M+Na)$^+$, 468.2 (M+H)$^+$, 416.1, 371.4, 323.3, 271.3, 230.2, 188.3.

Example 13 a] 1-Bromo-2-fluoro-4-(phenylmethoxy)-benzene

In analogy to the procedure described in example 8 b], 1-fluoro-3-(phenylmethoxy)-benzene (for the preparation of 1-fluoro-3-(phenylmethoxy)-benzene see: A. A. Durrani, J. H. P. Tyman, *J. Chem. Soc., Perkin Trans.* 1 1979, 8, 2079-2087) was treated with N-bromosuccinimide in the presence of concentrated sulfuric acid to give 1-bromo-2-fluoro-4-(phenylmethoxy)-benzene as colorless oil.

b] 4-Benzyloxy-2-fluoro-benzaldehyde

In analogy to the procedure described in example 8 c], 1-bromo-2-fluoro-4-(phenylmethoxy)-benzene was treated with n-BuLi and N,N-dimethylformamide in dry tetrahydrofuran to yield 4-benzyloxy-2-fluoro-benzaldehyde as off-white crystals.

MS: 230.1 (M)$^+$, 91.0, 65.2.

c] (S)-4-Benzyl-3-[(2S,3R)-3-(4-benzyloxy-2-fluoro-phenyl)-2-ethoxy-3-hydroxy-propionyl]-oxazolidin-2-one In analogy to the procedure described in example 1 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, *Tetrahedron: Asymmetry* 1999, 10, 1353-1367) was reacted with 4-benzyloxy-2-fluoro-benzaldehyde in the presence of triethylamine and di-n-butylboron triflate to give (S)-4-benzyl-3-[(2S,3R)-3-(4-benzyloxy-2-fluoro-phenyl)-2-ethoxy-3-hydroxy-propionyl]-oxazolidin-2-one as colorless foam. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353-1367.

MS: 516.2 (M+Na)$^+$, 476.2, 435.3, 419.3, 387.1, 330.2, 279.1, 227.2, 203.1.

d] (2S,3R)-3-(4-Benzyloxy-2-fluoro-phenyl)-2-ethoxy-3-hydroxy-propionic acid methyl ester In analogy to the procedure described in example 1 b], (S)-4-benzyl-3-[(2S,3R)-3-(4-benzyloxy-2-fluoro-phenyl)-2-ethoxy-3-hydroxy-propionyl]-oxazolidin-2-one was treated with sodium methoxide in methanol to give (2S,3R)-3-(4-benzyloxy-2-fluoro-phenyl)-2-ethoxy-3-hydroxy-propionic acid methyl ester as colorless liquid. According to $^1$H-NMR spectroscopy, one single diastereomer was obtained.

MS: 371.3 (M+Na)$^+$, 331.3, 303.2, 279.2, 242.2.

e] (2S)-3-(4-Benzyloxy-2-fluoro-phenyl)-2-ethoxy-propionic acid methyl ester In analogy to the procedure described in example 1 c], (2S,3R)-3-(4-benzyloxy-2-fluoro-phenyl)-2-ethoxy-3-hydroxy-propionic acid methyl ester was treated with triethylsilane in trifluoroacetic acid to yield (2S)-3-(4-benzyloxy-2-fluoro-phenyl)-2-ethoxy-propionic acid methyl ester as colorless liquid.

MS: 355.2 (M+Na)$^+$, 350.3 (M+NH$_4$)$^+$, 333.3 (M+H)$^+$, 287.2, 273.3, 245.3.

f] (2S)-2-Ethoxy-3-(2-fluoro-4-hydroxy-phenyl)-propionic acid methyl ester

In analogy to the procedure described in example 1 d], (2S)-3-(4-benzyloxy-2-fluoro-phenyl)-2-ethoxy-propionic acid methyl ester was hydrogenated over 10% palladium on charcoal to give (2S)-2-ethoxy-3-(2-fluoro-4-hydroxy-phenyl)-propionic acid methyl ester as colorless liquid.

MS: 265.2 (M+Na)$^+$, 260.2 (M+NH$_4$)$^+$, 243.3 (M+H)$^+$, 197.1, 183.2, 155.3.

g] (S)-2-Ethoxy-3-[2-fluoro-4-(5-methyl-2-phenyl-oxazol-4-ylmethoxy)-phenyl]-propionic acid methyl ester In analogy to the procedure described in example 1 f], (2S)-2-ethoxy-3-(2-fluoro-4-hydroxy-phenyl)-propionic acid methyl ester was reacted with 4-chloromethyl-5-methyl-2-phenyl-oxazole in the presence of cesium carbonate and potassium iodide to yield (S)-2-ethoxy-3-[2-fluoro-4-(5-methyl-2-phenyl-oxazol-4-ylmethoxy)-phenyl]-propionic acid methyl ester as colorless liquid.

MS: 436.2 (M+Na)$^+$, 414.2 (M+H)$^+$, 354.4, 213.3, 172.3.

h] (S)-2-Ethoxy-3-[2-fluoro-4-(5-methyl-2-phenyl-oxazol-4-ylmethoxy)-phenyl]-propionic acid In analogy to the procedure described in example 1 g], (S)-2-ethoxy-3-[2-fluoro-4-(5-methyl-2-phenyl-oxazol-4-ylmethoxy)-phenyl]-propionic acid methyl ester was treated with LiOH to obtain (S)-2-ethoxy-3-[2-fluoro-4-(5-methyl-2-phenyl-oxazol-4-ylmethoxy)-phenyl]-propionic acid as colorless solid.

MS: 422.2 (M+Na)$^+$, 400.4 (M+H)$^+$, 304.0, 269.2, 241.3, 213.3, 187.3, 172.3.

Example 14 a] (S)-2-Ethoxy-3-{2-fluoro-4-[2-(2-fluoro-phenyl)-5-methyl-oxazol-4-ylmethoxy]-phenyl}-propionic acid methyl ester In analogy to the procedure described in example 1 f], (2S)-2-ethoxy-3-(2-fluoro-4-hydroxy-phenyl)-propionic acid methyl ester (example 13 f]) was reacted with 4-chloromethyl-2-(2-fluoro-phenyl)-5-methyl-oxazole (prepared from 2-fluoro-benzaldehyde and diacetyl monoxyme followed by treatment with POCl$_3$ in analogy to the procedures described in examples 5 a] and 2 b]) in the presence of cesium carbonate and potassium iodide to yield (S)-2-ethoxy-3-{2-fluoro-4-[2-(2-fluoro-phenyl)-5-methyl-oxazol-4-ylmethoxy]-phenyl}-propionic acid methyl ester as colorless liquid.

MS: 454.3 (M+Na)$^+$, 449.3 (M+NH$_4$)$^+$, 432.4 (M+H)$^+$, 371.4, 304.2, 269.0, 231.3.

b] (S)-2-Ethoxy-3-{2-fluoro-4-[2-(2-fluoro-phenyl)-5-methyl-oxazol-4-ylmethoxy]-phenyl}-propionic acid In analogy to the procedure described in example 1 g], (S)-2-ethoxy-3-{2-fluoro-4-[2-(2-fluoro-phenyl)-5-methyl-oxazol-4-ylmethoxy]-phenyl}-propionic acid methyl ester was treated with LiOH to obtain (S)-2-ethoxy-3-{2-fluoro-4-[2-(2-fluoro-phenyl)-5-methyl-oxazol-4-ylmethoxy]-phenyl}-propionic acid as colorless liquid.

MS: 416.2 (M−H)$^−$, 370.1, 326.2, 255.3, 227.2.

Example 15 a] (S)-4-Benzyl-3-[(2S,3R)-3-(4-benzyloxy-2-chloro-phenyl)-2-ethoxy-3-hydroxy-propionyl]-oxazolidin-2-one In analogy to the procedure described in example 1 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, *Tetrahedron: Asymmetry* 1999, 10, 1353-1367) was reacted with 4-benzyloxy-2-chloro-benzaldehyde (for the preparation of 4-benzyloxy-2-chloro-benzaldehyde see: T. Kimachi, M. Kawase, S. Matsuki, K. Tanaka, F. Yoneda, *J. Chem. Soc., Perkin Trans.* 1 1990, 253-256) in the presence of triethylamine and di-n-butylboron triflate to give (S)-4-benzyl-3-[(2S,3R)-3-(4-benzyloxy-2-chloro-phenyl)-2-ethoxy-3-hydroxy-propionyl]-oxazolidin-2-one as colorless liquid. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353-1367.

MS: 532.3 $(M+Na)^+$, 527.2 $(M+NH_4)^+$, 446.1, 381.2, 315.1, 287.2, 243.2, 178.2.

b] (2S,3R)-3-(4-Benzyloxy-2-chloro-phenyl)-2-ethoxy-3-hydroxy-propionic acid methyl ester In analogy to the procedure described in example 1 b], (S)-4-benzyl-3-[(2S,3R)-3-(4-benzyloxy-2-chloro-phenyl)-2-ethoxy-3-hydroxy-propionyl]-oxazolidin-2-one was treated with sodium methoxide in methanol to give (2S,3R)-3-(4-benzyloxy-2-chloro-phenyl)-2-ethoxy-3-hydroxy-propionic acid methyl ester as colorless liquid. According to $^1$H-NMR spectroscopy, one single diastereomer was obtained.

MS: 387.1 $(M+Na)^+$, 382.2 $(M+NH_4)^+$, 328.2, 319.2, 279.2, 203.2.

c] (2S)-3-(4-Benzyloxy-2-chloro-phenyl)-2-ethoxy-propionic acid methyl ester In analogy to the procedure described in example 1 c], (2S,3R)-3-(4-benzyloxy-2-chloro-phenyl)-2-ethoxy-3-hydroxy-propionic acid methyl ester was treated with triethylsilane in trifluoroacetic acid to yield (2S)-3-(4-benzyloxy-2-chloro-phenyl)-2-ethoxy-propionic acid methyl ester as colorless liquid.

MS: 371.4 $(M+Na)^+$, 366.2 $(M+NH_4)^+$, 303.2, 269.2, 222.2, 187.2.

d] (2S)-3-(2-Chloro-4-hydroxy-phenyl)-2-ethoxy-propionic acid methyl ester

Dimethyl sulfide (5.8 ml, 79 mmol) and boron trifluoride diethyl etherate (46% purity, 4.3 ml, 16 mmol) were added to a ice cold solution of (2S)-3-(4-benzyloxy-2-chloro-phenyl)-2-ethoxy-propionic acid methyl ester (1.1 g, 3.2 mmol) in dichloromethane (34 ml) under an argon atmosphere. The mixture was stirred for 5 h at ambient temperature, poured into ice water/brine 1/1 and extracted two times with dichloromethane. The combined extracts were washed with ice water/brine 1/1 and dried over sodium sulfate. Removal of the solvent under reduced pressure gave a colorless oil which was purified by column chromatography (silica gel, cyclohexane/AcOEt) to yield 0.6 g (2.3 mmol, 74%) of the title compound as colorless oil.

MS: 281.0 $(M+Na)^+$, 276.1 $(M+NH_4)^+$, 251.3, 213.3, 187.2.

e] (S)-3-[2-Chloro-4-(5-methyl-2-phenyl-oxazol-4-ylmethoxy)-phenyl]-2-ethoxy-propionic acid methyl ester In analogy to the procedure described in example 1 f], (2S)-3-(2-chloro-4-hydroxy-phenyl)-2-ethoxy-propionic acid methyl ester was reacted with 4-chloromethyl-5-methyl-2-phenyl-oxazole in the presence of cesium carbonate and potassium iodide to yield (S)-3-[2-chloro-4-(5-methyl-2-phenyl-oxazol-4-ylmethoxy)-phenyl]-2-ethoxy-propionic acid methyl ester as colorless liquid.

MS: 452.3 $(M+Na)^+$, 430.3 $(M+H)^+$, 251.3, 213.3, 172.2.

f] (S)-3-[2-Chloro-4-(5-methyl-2-phenyl-oxazol-4-ylmethoxy)-phenyl]-2-ethoxy-propionic acid In analogy to the procedure described in example 1 g], (S)-3-[2-chloro-4-(5-methyl-2-phenyl-oxazol-4-ylmethoxy)-phenyl]-2-ethoxy-propionic acid methyl ester was treated with LiOH to obtain (S)-3-[2-chloro-4-(5-methyl-2-phenyl-oxazol-4-ylmethoxy)-phenyl]-2-ethoxy-propionic acid as colorless solid.

MS: 438.0 $(M+Na)^+$, 416.1 $(M+H)^+$, 371.4, 304.1, 263.1, 213.3, 172.3.

Example 16 a] (S)-3-{2-Chloro-4-[2-(4-fluoro-3-methyl-phenyl)-5-methyl-oxazol-4-ylmethoxy]-phenyl}-2-ethoxy-propionic acid methyl ester In analogy to the procedure described in example 1 f], (2S)-3-(2-chloro-4-hydroxy-phenyl)-2-ethoxy-propionic acid methyl ester (example 15 d]) was reacted with 4-chloromethyl-2-(4-fluoro-3-methyl-phenyl)-5-methyl-oxazole (example 5 b]) in the presence of cesium carbonate and potassium iodide to yield (S)-3-{2-chloro-4-[2-(4-fluoro-3-methyl-phenyl)-5-methyl-oxazol-4-ylmethoxy]-phenyl}-2-ethoxy-propionic acid methyl ester as colorless liquid.

MS: 484.2 $(M+Na)^+$, 462.2 $(M+H)^+$, 345.1, 245.3, 204.2, 166.4.

b] (S)-3-{2-Chloro-4-[2-(4-fluoro-3-methyl-phenyl)-5-methyl-oxazol-4-ylmethoxy]-phenyl}-2-ethoxy-propionic acid In analogy to the procedure described in example 1 g], (S)-3-{2-chloro-4-[2-(4-fluoro-3-methyl-phenyl)-5-methyl-oxazol-4-ylmethoxy]-phenyl}-2-ethoxy-propionic acid methyl ester was treated with LiOH to obtain (S)-3-{2-chloro-4-[2-(4-fluoro-3-methyl-phenyl)-5-methyl-oxazol-4-ylmethoxy]-phenyl}-2-ethoxy-propionic acid as colorless solid.

MS: 470.0 $(M+Na)^+$, 448.2 $(M+H)^+$, 371.4, 275.2, 245.3, 204.2, 187.3.

Example 17 a] (S)-3-{2-Chloro-4-[2-(4-isopropoxy-phenyl)-5-methyl-oxazol-4-ylmethoxy]-phenyl}-2-ethoxy-propionic acid methyl ester In analogy to the procedure described in example 1 f], (2S)-3-(2-chloro-4-hydroxy-phenyl)-2-ethoxy-propionic acid methyl ester (example 15 d]) was reacted with 4-chloromethyl-2-(4-isopropoxy-phenyl)-5-methyl-oxazole (example 2 b]) in the presence of cesium carbonate and potassium iodide to yield (S)-3-{2-chloro-4-[2-(4-isopropoxy-phenyl)-5-methyl-oxazol-4-ylmethoxy]-phenyl}-2-ethoxy-propionic acid methyl ester as colorless liquid.

MS: 510.3 (M+Na)$^+$, 488.3 (M+H)$^+$, 271.3, 230.2, 188.3.

b] (S)-3-{2-Chloro-4-[2-(4-isopropoxy-phenyl)-5-methyl-oxazol-4-ylmethoxy]-phenyl}-2-ethoxy-propionic acid In analogy to the procedure described in example 1 g], (S)-3-{2-chloro-4-[2-(4-isopropoxy-phenyl)-5-methyl-oxazol-4-ylmethoxy]-phenyl}-2-ethoxy-propionic acid methyl ester was treated with LiOH to obtain (S)-3-{2-chloro-4-[2-(4-isopropoxy-phenyl)-5-methyl-oxazol-4-ylmethoxy]-phenyl}-2-ethoxy-propionic acid as colorless foam.

MS: 496.1 (M+Na)$^+$, 474.2 (M+H)$^+$, 424.3, 271.2, 230.2, 188.3, 172.2.

Example 18 a] (S)-3-{2-Chloro-4-[2-(2-fluoro-phenyl)-5-methyl-oxazol-4-ylmethoxy]-phenyl}-2-ethoxy-propionic acid methyl ester In analogy to the procedure described in example 1 f], (2S)-3-(2-chloro-4-hydroxy-phenyl)-2-ethoxy-propionic acid methyl ester (example 15 d]) was reacted with 4-chloromethyl-2-(2-fluoro-phenyl)-5-methyl-oxazole (prepared from 2-fluoro-benzaldehyde and diacetyl monoxyme followed by treatment with POCl$_3$ in analogy to the procedures described in examples 5 a] and 2 b]) in the presence of cesium carbonate and potassium iodide to yield (S)-3-{2-chloro-4-[2-(2-fluoro-phenyl)-5-methyl-oxazol-4-ylmethoxy]-phenyl}-2-ethoxy-propionic acid methyl ester as colorless liquid.

MS: 470.1 (M+Na)$^+$, 448.2 (M+H)$^+$, 269.1, 231.2, 190.3, 163.3.

b] (S)-3-{2-Chloro-4-[2-(2-fluoro-phenyl)-5-methyl-oxazol-4-ylmethoxy]-phenyl}-2-ethoxy-propionic acid In analogy to the procedure described in example 1 g], (S)-3-{2-chloro-4-[2-(2-fluoro-phenyl)-5-methyl-oxazol-4-ylmethoxy]-phenyl}-2-ethoxy-propionic acid methyl ester was treated with LiOH to obtain (S)-3-{2-chloro-4-[2-(2-fluoro-phenyl)-5-methyl-oxazol-4-ylmethoxy]-phenyl}-2-ethoxy-propionic acid as colorless solid.

MS: 456.1 (M+Na)$^+$, 434.2 (M+H)$^+$, 428.3, 382.1, 279.1, 231.2, 190.3.

Example 19 a] (S)-3-[2-Chloro-4-(5-methyl-2-o-tolyl-oxazol-4-ylmethoxy)-phenyl]-2-ethoxy-propionic acid methyl ester In analogy to the procedure described in example 1 f], (2S)-3-(2-chloro-4-hydroxy-phenyl)-2-ethoxy-propionic acid methyl ester (example 15 d]) was reacted with 4-chloromethyl-5-methyl-2-o-tolyl-oxazole (example 1 e]) in the presence of cesium carbonate and potassium iodide to yield (S)-3-[2-chloro-4-(5-methyl-2-o-tolyl-oxazol-4-ylmethoxy)-phenyl]-2-ethoxy-propionic acid methyl ester as colorless liquid.

MS: 444.2 (M+H)$^+$, 319.3, 279.2, 227.3, 186.3, 181.2, 166.3.

b] (S)-3-[2-Chloro-4-(5-methyl-2-o-tolyl-oxazol-4-ylmethoxy)-phenyl]-2-ethoxy-propionic acid In analogy to the procedure described in example 1 g], (S)-3-[2-chloro-4-(5-methyl-2-o-tolyl-oxazol-4-ylmethoxy)-phenyl]-2-ethoxy-propionic acid methyl ester was treated with LiOH to obtain (S)-3-[2-chloro-4-(5-methyl-2-o-tolyl-oxazol-4-ylmethoxy)-phenyl]-2-ethoxy-propionic acid as colorless liquid.

MS: 430.3 (M+H)$^+$, 390.2, 349.3, 292.4, 279.2, 186.3, 176.2, 161.3.

Example 20 a] (S)-3-{2-Chloro-4-[2-(2-methoxy-phenyl)-5-methyl-oxazol-4-ylmethoxy]-phenyl}-2-ethoxy-propionic acid methyl ester In analogy to the procedure described in example 1 f], (2S)-3-(2-chloro-4-hydroxy-phenyl)-2-ethoxy-propionic acid methyl ester (example 15 d]) was reacted with 4-chloromethyl-2-(2-methoxy-phenyl)-5-methyl-oxazole (prepared from 2-methoxy-benzaldehyde and diacetyl monoxyme followed by treatment with POCl$_3$ in analogy to the procedures described in examples 5 a] and 2 b]) in the presence of cesium carbonate and potassium iodide to yield (S)-3-{2-chloro-4-[2-(2-methoxy-phenyl)-5-methyl-oxazol-4-ylmethoxy]-phenyl}-2-ethoxy-propionic acid methyl ester as colorless liquid.

MS: 482.2 (M+Na)$^+$, 360.2 (M+H)$^+$, 391.2, 330.3, 284.1, 254.2, 202.2.

b] (S)-3-{2-Chloro-4-[2-(2-methoxy-phenyl)-5-methyl-oxazol-4-ylmethoxy]-phenyl}-2-ethoxy-propionic acid In analogy to the procedure described in example 1 g], (S)-3-{2-chloro-4-[2-(2-methoxy-phenyl)-5-methyl-oxazol-4-ylmethoxy]-phenyl}-2-ethoxy-propionic acid methyl ester was treated with LiOH to obtain (S)-3-{2-chloro-4-[2-(2-methoxy-phenyl)-5-methyl-oxazol-4-ylmethoxy]-phenyl}-2-ethoxy-propionic acid as colorless foam.

MS: 468.1 (M+Na)$^+$, 446.2 (M+H)$^+$, 371.4, 329.2, 269.2, 202.1.

Example 21 a] 1-Bromo-2-trifluoromethyl-4-(phenylmethoxy)-benzene

A solution of 1-trifluoromethyl-3-(phenylmethoxy)-benzene (5.7 g, 22.6 mmol) in glacial acetic acid (25 ml) with sodium acetate (2.7 g, 32.5 mmol) was cooled to 0° C. and bromine (1.6 ml, 31.7 mmol) was added slowly with stirring. A calcium chloride guard tube was fitted and the mixture was stirred in the dark, at room temperature, for 24 h. The resulting slurry was diluted with dichloromethane and washed with 10% aqueous sodium thiosulphate, aqueous potassium carbonate, and water. The organic layer was dried over sodium sulfate and the solvent was removed under reduced pressure to give a yellow oil, which was purified by column chromatography (silica gel, cyclohexane) to yield 6 g of a colorless oil. According to $^1$H-NMR the oil consists of a 1/1 mixture of starting material and the title compound. This mixture was used in the next step without further purification.

b] 4-Benzyloxy-2-trifluoromethyl-benzaldehyde

In analogy to the procedure described in example 8 c], 1-bromo-2-trifluoromethyl-4-(phenylmethoxy)-benzene was treated with n-BuLi and N,N-dimethylformamide in dry tetrahydrofuran to yield 4-benzyloxy-2-trifluoromethyl-benzaldehyde as colorless liquid.
MS: 298.3 $(M+NH_4)^+$, 281.1 $(M)^+$, 236.1, 224.3, 181.2.

c] (S)-4-Benzyl-3-[(2S,3R)-3-(4-benzyloxy-2-trifluoromethyl-phenyl)-2-ethoxy-3-hydroxy-propionyl]-oxazolidin-2-one In analogy to the procedure described in example 1 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, Tetrahedron: Asymmetry 1999, 10, 1353-1367) was reacted with 4-benzyloxy-2-trifluoromethyl-benzaldehyde in the presence of triethylamine and di-n-butylboron triflate to give (S)-4-benzyl-3-[(2S,3R)-3-(4-benzyloxy-2-trifluoromethyl-phenyl)-2-ethoxy-3-hydroxy-propionyl]-oxazolidin-2-one as colorless liquid. According to $^1$H-NMR spectroscopy, one of the four isomers is strongly predominating. The configuration was tentatively assigned as 2S,3R according to D. Haigh et al., Tetrahedron: Asymmetry 1999, 10, 1353-1367.
MS: 566.3 $(M+Na)^+$, 561.4 $(M+NH_4)^+$, 526.3, 458.2, 349.3, 301.3.

d] (2S,3R)-3-(4-Benzyloxy-2-trifluoromethyl-phenyl)-2-ethoxy-3-hydroxy-propionic acid methyl ester In analogy to the procedure described in example 1 b], (S)-4-benzyl-3-[(2S,3R)-3-(4-benzyloxy-2-trifluoromethyl-phenyl)-2-ethoxy-3-hydroxy-propionyl]-oxazolidin-2-one was treated with sodium methoxide in methanol to give (2S,3R)-3-(4-benzyloxy-2-trifluoromethyl-phenyl)-2-ethoxy-3-hydroxy-propionic acid methyl ester as colorless liquid. According to $^1$H-NMR spectroscopy, one single diastereomer was obtained.
MS: 421.2 $(M+Na)^+$, 416.2 $(M+NH_4)^+$, 381.3, 353.2, 313.3, 222.2, 192.4.

e] (2S)-3-(4-Benzyloxy-2-trifluoromethyl-phenyl)-2-ethoxy-propionic acid methyl ester In analogy to the procedure described in example 1 c], (2S,3R)-3-(4-benzyloxy-2-trifluoromethyl-phenyl)-2-ethoxy-3-hydroxy-propionic acid methyl ester was treated with triethylsilane in trifluoroacetic acid to yield (2S)-3-(4-benzyloxy-2-trifluoromethyl-phenyl)-2-ethoxy-propionic acid methyl ester as colorless liquid.
MS: 405.4 $(M+Na)^+$, 400.4 $(M+NH_4)^+$, 337.2, 269.2.

f] (2S)-2-Ethoxy-3-(4-hydroxy-2-trifluoromethyl-phenyl)-propionic acid methyl ester In analogy to the procedure described in example 1 d], (2S)-3-(4-benzyloxy-2-trifluoromethyl-phenyl)-2-ethoxy-propionic acid methyl ester was hydrogenated over 10% palladium on charcoal to give (2S)-2-ethoxy-3-(4-hydroxy-2-trifluoromethyl-phenyl)-propionic acid methyl ester as yellow solid.
MS: 291.1 $(M-H)^-$, 255.2, 206.0, 174.1, 141.1.

g] (S)-2-Ethoxy-3-[4-(5-methyl-2-phenyl-oxazol-4-ylmethoxy)-2-trifluoromethyl-phenyl]-propionic acid methyl ester In analogy to the procedure described in example 1 f], (2S)-2-ethoxy-3-(4-hydroxy-2-trifluoromethyl-phenyl)-propionic acid methyl ester was reacted with 4-chloromethyl-5-methyl-2-phenyl-oxazole in the presence of cesium carbonate and potassium iodide to yield (S)-2-ethoxy-3-[4-(5-methyl-2-phenyl-oxazol-4-ylmethoxy)-2-trifluoromethyl-phenyl]-propionic acid methyl ester as colorless liquid.
MS: 486.3 $(M+Na)^+$, 464.3 $(M+H)^+$, 411.0, 371.4, 304.2, 279.3.

h] (S)-2-Ethoxy-3-[4-(5-methyl-2-phenyl-oxazol-4-ylmethoxy)-2-trifluoromethyl-phenyl]-propionic acid In analogy to the procedure described in example 1 g], (S)-2-ethoxy-3-[4-(5-methyl-2-phenyl-oxazol-4-ylmethoxy)-2-trifluoromethyl-phenyl]-propionic acid methyl ester was treated with LiOH to obtain (S)-2-ethoxy-3-[4-(5-methyl-2-phenyl-oxazol-4-ylmethoxy)-2-trifluoromethyl-phenyl]-propionic acid as colorless solid.
MS: 448.2 $(M-H)^-$, 431.1, 402.2, 277.2, 231.1.

Example 22 a] (S)-2-Ethoxy-3-{4-[2-(2-fluoro-phenyl)-5-methyl-oxazol-4-ylmethoxy]-2-trifluoromethyl-phenyl}-propionic acid methyl ester In analogy to the procedure described in example 1 f], (2S)-2-ethoxy-3-(4-hydroxy-2-trifluoromethyl-phenyl)-propionic acid methyl ester (example 21 f]) was reacted with with 4-chloromethyl-2-(2-fluoro-phenyl)-5-methyl-oxazole (prepared from 2-fluoro-benzaldehyde and diacetyl monoxyme followed by treatment with POCl$_3$ in analogy to the procedures described in examples 5 a] and 2 b]) in the presence of cesium carbonate and potassium iodide to yield (S)-2-ethoxy-3-{4-[2-(2-fluoro-phenyl)-5-methyl-oxazol-4-ylmethoxy]-2-trifluoromethyl-phenyl}-propionic acid methyl ester as colorless solid.
MS: 504.3 $(M+Na)^+$, 482.3 $(M+H)^+$, 428.5, 345.2, 303.8, 269.2, 231.2.

b] (S)-2-Ethoxy-3-{4-[2-(2-fluoro-phenyl)-5-methyl-oxazol-4-ylmethoxy]-2-trifluoromethyl-phenyl}-propionic acid In analogy to the procedure described in example 1 g], (S)-2-ethoxy-3-{4-[2-(2-fluoro-phenyl)-5-methyl-oxazol-4-ylmethoxy]-2-trifluoromethyl-phenyl}-propionic acid methyl ester was treated with LiOH to obtain (S)-2-ethoxy-3-{4-[2-(2-fluoro-phenyl)-5-methyl-oxazol-4-ylmethoxy]-2-trifluoromethyl-phenyl}-propionic acid as colorless liquid.
MS: 466.3 $(M-H)^-$, 420.1, 376.3, 316.9, 277.1, 231.2.

Example 23 a] 2-Hydroxy-4-[2-(5-methyl-2-phenyl-oxazol-4-yl)-ethoxy]-benzaldehyde

A solution of 2,4-dihydroxy-benzaldehyde (2 g, 14.5 mmol) in 20 ml THF was cooled to 0° C. To this solution were added triphenylphosphine (9.7 g, 37 mmol), 2-(2-phenyl-5-methyl-oxazol-4-yl)-ethanol (2.84 g, 14 mmol) and finally during 0.75 hours a solution of di-tert-butyl azodicarboxylate (8.52 g, 37 mmol) in 20 ml THF. The reaction mixture was stirred overnight at room temperature, evaporated to dryness, purified by chromatography ($SiO_2$; AcOEt/heptane) and the product was crystallized from AcOEt/ether/heptane to yield 2.2 g (46%) of the title compound as a colorless solid.

b] 2-[Dimethyl-(1,1,2-trimethyl-propyl)-silanyloxy]-4-[2-(5-methyl-2-phenyl-oxazol-4-yl)-ethoxy]-benzaldehyde To a solution of 2-hydroxy-4-[2-(5-methyl-2-phenyl-oxazol-4-yl)-ethoxy]-benzaldehyde (540 mg, 1.67 mmol) in 8 ml N,N-dimethylformamide cooled to 0° C., were added 398 mg (5.85 mol) imidazole and 1.1 ml (5.85 mmol) thexyldimethylchlorosilane. The reaction mixture was stirred 50 minutes at 0° C., diluted with AcOEt, washed with water/ice, HCl (1M)/ice and brine and the aqueous layer was extracted with AcOEt. The combined organic layers were dried over $Na_2SO_4$ and evaporated. Chromatography ($SiO_2$; AcOEt/heptane) delivered 346 mg (45%) of the title compound as an oil.

MS: $(M+H^+)^+$ 466.3.

c] (S)-4-Benzyl-3-((2S,3R)-3-{2-[dimethyl-(1,1,2-trimethyl-propyl)-silanyloxy]-4-[2-(5-methyl-2-phenyl-oxazol-4-yl)-ethoxy]-phenyl}-3-hydroxy-2-methoxy-propionyl)-oxazolidin-2-one 1.8 g (7.21 mmol) (S)-4-Benzyl-3-methoxyacetyl-oxazolidin-2-one (for the preparation of (S)-4-benzyl-3-methoxyacetyl-oxazolidin-2-one see: D. Hunziker, N. Wu, K. Kenoshita, D. E. Cane, C. Khosla, Tetrahedron Lett. 1999, 40, 635-638) were dissolved under an argon atmosphere in 10 ml $CH_2Cl_2$ and treated with 1.44 ml (8.42 mmol) Hünig's base. After cooling to −78° C., $nBu_2BOTf$ was added slowly (7.21 ml of 1M solution in $CH_2Cl_2$) and enolborinate formation allowed to proceed for 0.25 hours at −78° C. and for 1 hour at 0° C. After recooling to −78° C., a solution of 2.8 g (6 mmol) of 2-[dimethyl-(1,1,2-trimethyl-propyl)-silanyloxy]-4-[2-(5-methyl-2-phenyl-oxazol-4-yl)-ethoxy]-benzaldehyde in 10 ml $CH_2Cl_2$ was added via dropping funnel during 90 minutes and the mixture kept for 95 minutes at −78° C. and for one hour at 0° C. Pouring onto crashed ice, twofold extraction with AcOEt, washing with brine and water, drying over magnesium sulfate, and evaporation of the solvents, followed by chromatography (silica gel, heptane/AcOEt) left finally 2.905 g (67%) of the title compound as a yellow oil. According to $^1$H-NMR spectroscopy, one of the four isomers is strongly predominating. The configuration was tentatively assigned as 2S,3R according to D. Haigh et al., Tetrahedron: Asymmetry 1999, 10, 1353-1367.

MS: $(M+Na^+)$+ 737.3, $(M+H^+)$+ 715.3.

d] (S)-4-Benzyl-3-(3-{2-[dimethyl-(1,1,2-trimethyl-propyl)-silanyloxy]-4-[2-(5-methyl-2-phenyl-oxazol-4-yl)-ethoxy]-phenyl}-2-(2S)-methoxy-propionyl)-oxazolidin-2-one The above prepared (S)-4-benzyl-3-((2S,3R)-3-{2-[dimethyl-(1,1,2-trimethyl-propyl)-silanyloxy]-4-[2-(5-methyl-2-phenyl-oxazol-4-yl)-ethoxy]-phenyl}-3-hydroxy-2-methoxy-propionyl)-oxazolidin-2-one (2.8 g, 3.91 mmol) was dissolved in 10 ml of trifluoroacetic acid, treated at 0° C. with 10 ml of triethylsilane and then kept for 3 hours at ambient temperature. The reaction mixture was then poured onto crashed ice/AcOEt/NaOH (1M), the organic layer was washed with water and brine, dried over magnesium sulfate and evaporated to dryness. Flash chromatography ($SiO_2$, heptane/AcOEt) delivered 1.6 g (58%) of the title compound (purity ~80%) as a yellow foam.

MS: 596.4 $(M)^+$.

e] (S)-4-Benzyl-3-(3-[2-hydroxy-4-[2-(5-methyl-2-phenyl-oxazol-4-yl)-ethoxy]-phenyl]-(2S)-2-methoxy-propionyl)-oxazolidin-2-one To a solution of (S)-4-benzyl-3-(3-{2-[dimethyl-(1,1,2-trimethyl-propyl)-silanyloxy]-4-[2-(5-methyl-2-phenyl-oxazol-4-yl)-ethoxy]-phenyl}-2-(2S)-methoxy-propionyl)-oxazolidin-2-one (1.6 g, 2.29 mmol) in 10 ml methanol, was added $NH_4F$ (169 mg, 4.58 mmol) and the reaction mixture kept at r.t. for 2 hours. It was then diluted with AcOEt, washed with water/ice and brine, the aqueous layer was extracted with AcOEt, the combined organic layers dried over $Na_2SO_4$ and evaporated. The crude product (1.22 g) was found to be a mixture of the title compound and of (S)-3-{2-hydroxy-4-[2-(5-methyl-2-phenyl-oxazol-4-yl)-ethoxy]-phenyl}-2-methoxy-propionic acid methyl ester and used without purification for the last step.

f] (S)-3-{2-Hydroxy-4-[2-(5-methyl-2-phenyl-oxazol-4-yl)-ethoxy]-phenyl}-2-methoxy-propionic acid 1.22 g of the mixture prepared above was dissolved in 5 ml of THF and treated with 5 ml of 1N NaOH. The reaction mixture was kept at 0° C. overnight. Then, it was washed twice with ether. The aqueous layer was acidified (pH 3 with HCl (1M)/ice), extracted twice with AcOEt, the organic layers were dried over magnesium sulfate, and evaporated to give a crude product, which was purified by crystalization from AcOEt/heptane to remove the chiral auxiliary. Thereby, 0.240 g (27%) of the title compound was obtained as a white solid. According to chiral HPLC (Chiralpak-AD), an enantiomeric excess of close to 100% was observed.

MS: 396.2 $(M–H)^-$.

Example 24 a] (S)-4-Benzyl-3-[(2S,3R)-3-(4-benzyloxy-2-methoxy-phenyl)-2-ethoxy-3-hydroxy-propionyl]-oxazolidin-2-one In analogy to the procedure described in example 1 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, Tetrahedron: Asymmetry 1999, 10, 1353-1367) was reacted with 4-benzyloxy-2-methoxybenzaldehyde in the presence of triethylamine and di-n-butylboron triflate to give (S)-4-benzyl-3-[(2S,3R)-3-(4-benzyloxy-2-methoxy-phenyl)-2-ethoxy-3-hydroxy-propionyl]-oxazolidin-2-one as light yellow solid. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353-1367.

MS: 528.3 (M+Na)$^+$, 523.3 (M+NH$_4$)$^+$, 488.3, 442.4, 311.2, 239.3.

b] (2S,3R)-3-(4-Benzyloxy-2-methoxy-phenyl)-2-ethoxy-3-hydroxy-propionic acid methyl ester In analogy to the procedure described in example 1 b], (S)-4-benzyl-3-[(2S,3R)-3-(4-benzyloxy-2-methoxy-phenyl)-2-ethoxy-3-hydroxy-propionyl]-oxazolidin-2-one was treated with sodium methoxide in methanol to give (2S,3R)-3-(4-benzyloxy-2-methoxy-phenyl)-2-ethoxy-3-hydroxy-propionic acid methyl ester as colorless liquid. According to $^1$H-NMR spectroscopy, one single diastereomer was obtained.

MS: 383.2 (M+Na)$^+$, 378.2 (M+NH$_4$)$^+$, 343.2, 311.2, 283.2, 239.3, 163.2.

c] (2S)-2-Ethoxy-3-(4-hydroxy-2-methoxy-phenyl)-propionic acid methyl ester

A solution of (2S,3R)-3-(4-benzyloxy-2-methoxy-phenyl)-2-ethoxy-3-hydroxy-propionic acid methyl ester (100 mg, 200 μmol) and oxalic acid dihydrate (150 mg, 1.2 mmol) in isopropanol (2 ml) was hydrogenated at a pressure of 50 atmospheres over 10% palladium on charcoal (20 mg) at ambient temperature for 6.5 h. The catalyst was filtered off and the solvent evaporated under reduced pressure. The residue was dissolved in ice water/aqueous sodium bicarbonate solution 1/1 and extracted two times with ethyl acetate. The combined extracts were washed two times with ice water/brine 1/1 and dried over sodium sulfate. The solvent was removed under reduced pressure to give a yellow liquid which was purified by column chromatography (silica gel, cyclohexane/AcOEt) to yield 43 mg (170 μmol, 85%) of the title compound as light yellow liquid.

MS: 277.1 (M+Na)$^+$, 209.2, 195.3, 181.2, 177.2, 167.2.

d] (S)-2-Ethoxy-3-[2-methoxy-4-(5-methyl-2-phenyl-oxazol-4-ylmethoxy)-phenyl]-propionic acid methyl ester In analogy to the procedure described in example 1 f], (2S)-2-ethoxy-3-(4-hydroxy-2-methoxy-phenyl)-propionic acid methyl ester was reacted with 4-chloromethyl-5-methyl-2-phenyl-oxazole in the presence of cesium carbonate and potassium iodide to yield (S)-2-ethoxy-3-[2-methoxy-4-(5-methyl-2-phenyl-oxazol-4-ylmethoxy)-phenyl]-propionic acid methyl ester as colorless liquid.

MS: 448.2 (M+Na)$^+$, 426.3 (M+H)$^+$, 380.2, 319.2, 213.3, 172.2.

e] (S)-2-Ethoxy-3-[2-methoxy-4-(5-methyl-2-phenyl-oxazol-4-ylmethoxy)-phenyl]-propionic acid In analogy to the procedure described in example 1 g], (S)-2-ethoxy-3-[2-methoxy-4-(5-methyl-2-phenyl-oxazol-4-ylmethoxy)-phenyl]-propionic acid methyl ester was treated with LiOH to obtain (S)-2-ethoxy-3-[2-methoxy-4-(5-methyl-2-phenyl-oxazol-4-ylmethoxy)-phenyl]-propionic acid as colorless solid.

MS: 410.6 (M–H)$^-$, 369.9, 304.2, 285.2, 261.3, 238.9, 229.6, 191.3.

Example 25 a] (S)-2-Ethoxy-3-{4-[2-(4-isopropyl-phenyl)-5-methyl-oxazol-4-ylmethoxy]-2-methoxy-phenyl}-propionic acid methyl ester In analogy to the procedure described in example 1 f], (2S)-2-ethoxy-3-(4-hydroxy-2-methoxy-phenyl)-propionic acid methyl ester (example 24 c]) was reacted with 4-chloromethyl-2-(4-isopropyl-phenyl)-5-methyl-oxazole (prepared from 4-isopropyl-benzaldehyde and diacetyl monoxyme followed by treatment with POCl$_3$ in analogy to the procedures described in examples 5 a] and 2 b]) in the presence of cesium carbonate and potassium iodide to yield (S)-2-ethoxy-3-{4-[2-(4-isopropyl-phenyl)-5-methyl-oxazol-4-ylmethoxy]-2-methoxy-phenyl}-propionic acid methyl ester as orange liquid.

MS: 490.2 (M+Na)$^+$, 468.2 (M+H)$^+$, 344.3, 311.2, 255.2, 214.4, 198.4.

b] (S)-2-Ethoxy-3-{4-[2-(4-isopropyl-phenyl)-5-methyl-oxazol-4-ylmethoxy]-2-methoxy-phenyl}-propionic acid In analogy to the procedure described in example 1 g], (S)-2-ethoxy-3-{4-[2-(4-isopropyl-phenyl)-5-methyl-oxazol-4-ylmethoxy]-2-methoxy-phenyl}-propionic acid methyl ester was treated with LiOH to obtain (S)-2-ethoxy-3-{4-[2-(4-isopropyl-phenyl)-5-methyl-oxazol-4-ylmethoxy]-2-methoxy-phenyl}-propionic acid as colorless solid.

MS: 476.2 (M+Na)$^+$, 454.3 (M+H)$^+$, 404.5, 255.2, 214.3.

Example 26 a] (S)-2-Ethoxy-3-{4-[2-(4-fluoro-3-methyl-phenyl)-5-methyl-oxazol-4-ylmethoxy]-2-methoxy-phenyl}-propionic acid methyl ester In analogy to the procedure described in example 1 f], (2S)-2-ethoxy-3-(4-hydroxy-2-methoxy-phenyl)-propionic acid methyl ester (example 24 c]) was reacted with 4-chloromethyl-2-(4-fluoro-3-methyl-phenyl)-5-methyl-oxazole (examples 5 b]) in the presence of cesium carbonate and potassium iodide to yield (S)-2-ethoxy-3-{4-[2-(4-fluoro-3-methyl-phenyl)-5-methyl-oxazol-4-ylmethoxy]-2-methoxy-phenyl}-propionic acid methyl ester as colorless liquid.

MS: 480.4 (M+Na)$^+$, 458.3 (M+H)$^+$, 412.2, 245.3, 204.2, 177.2.

b] (S)-2-Ethoxy-3-[4-{2-(4-fluoro-3-methyl-phenyl)-5-methyl-oxazol-4-ylmethoxy]-2-methoxy-phenyl}-propionic acid In analogy to the procedure described in example 1 g], (S)-2-ethoxy-3-{4-[2-(4-fluoro-3-methyl-phenyl)-5-methyl-oxazol-4-ylmethoxy]-2-methoxy-phenyl}-propionic acid methyl ester was treated with LiOH to obtain (S)-2-ethoxy-3-{4-[2-(4-fluoro-3-methyl-phenyl)-5-methyl-oxazol-4-ylmethoxy]-2-methoxy-phenyl}-propionic acid as colorless solid.

MS: 466.1 (M+Na)$^+$, 444.2 (M+H)$^+$, 392.1, 365.2, 297.3, 245.3, 204.2.

Example 27 a] (S)-2-Ethoxy-3-{4-[2-(4-isopropoxy-phenyl)-5-methyl-oxazol-4-ylmethoxy]-2-methoxy-phenyl}-propionic acid methyl ester In analogy to the procedure described in example 1 f], (2S)-2-ethoxy-3-(4-hydroxy-2-methoxy-phenyl)-propionic acid methyl ester (example 24 c]) was reacted with 4-chloromethyl-2-(4-isopropoxy-phenyl)-5-methyl-oxazole (examples 2 b]) in the presence of cesium carbonate and potassium iodide to yield (S)-2-ethoxy-3-{4-[2-(4-isopropoxy-phenyl)-5-methyl-oxazol-4-ylmethoxy]-2-methoxy-phenyl}-propionic acid methyl ester as colorless liquid.

MS: 506.5 (M+Na)$^+$, 484.3 (M+H)$^+$, 323.3, 271.3, 230.2, 188.3.

b] (S)-2-Ethoxy-3-{4-[2-(4-isopropoxy-phenyl)-5-methyl-oxazol-4-ylmethoxy]-2-methoxy-phenyl}-propionic acid In analogy to the procedure described in example 1 g], (S)-2-ethoxy-3-{4-[2-(4-isopropoxy-phenyl)-5-methyl-oxazol-4-ylmethoxy]-2-methoxy-phenyl}-propionic acid methyl ester was treated with LiOH to obtain (S)-2-ethoxy-3-{4-[2-(4-isopropoxy-phenyl)-5-methyl-oxazol-4-ylmethoxy]-2-methoxy-phenyl}-propionic acid as colorless solid.

MS: 492.2 (M+Na)$^+$, 470.2 (M+H)$^+$, 357.2, 335.2, 279.2, 235.2, 187.3.

Example 28 a] (S)-3-{4-[2-(3-Chloro-phenyl)-5-methyl-oxazol-4-ylmethoxy]-2-methoxy-phenyl}-2-ethoxy-propionic acid methyl ester In analogy to the procedure described in example 1 f], (2S)-2-ethoxy-3-(4-hydroxy-2-methoxy-phenyl)-propionic acid methyl ester (example 24 c]) was reacted with 4-chloromethyl-2-(3-chloro-phenyl)-5-methyl-oxazole (prepared from 3-chloro-benzaldehyde and diacetyl monoxyme followed by treatment with POCl$_3$ in analogy to the procedures described in examples 5 a] and 2 b]) in the presence of cesium carbonate and potassium iodide to yield (S)-3-{4-[2-(3-chloro-phenyl)-5-methyl-oxazol-4-ylmethoxy]-2-methoxy-phenyl}-2-ethoxy-propionic acid methyl ester as colorless liquid.

MS: 482.2 (M+Na)$^+$, 460.2 (M+H)$^+$, 414.1, 357.2, 335.3, 279.2, 235.2, 206.1.

b] (S)-3-{4-[2-(3-Chloro-phenyl)-5-methyl-oxazol-4-ylmethoxy]-2-methoxy-phenyl}-2-ethoxy-propionic acid In analogy to the procedure described in example 1 g], (S)-3-{4-[2-(3-chloro-phenyl)-5-methyl-oxazol-4-ylmethoxy]-2-methoxy-phenyl}-2-ethoxy-propionic acid methyl ester was treated with LiOH to obtain (S)-3-{4-[2-(3-chloro-phenyl)-5-methyl-oxazol-4-ylmethoxy]-2-methoxy-phenyl}-2-ethoxy-propionic acid as colorless liquid.

MS: 468.1 (M+Na)$^+$, 446.1 (M+H)$^+$, 394.2, 352.2, 302.2, 269.2, 206.1, 149.1.

Example 29 a] 4-Benzyloxy-2,6-dimethyl-benzaldehyde

In analogy to the procedure described in example 8 a], 4-hydroxy-2,6-dimethyl-benzaldehyde was reacted with benzyl bromide in the presence of potassium carbonate to yield 4-benzyloxy-2,6-dimethyl-benzaldehyde as orange liquid.

MS: 241.2 (M+H)$^+$, 181.0.

b] (S)-4-Benzyl-3-[(2S,3R)-3-(4-benzyloxy-2,6-dimethyl-phenyl)-2-ethoxy-3-hydroxy-propionyl]-oxazolidin-2-one In analogy to the procedure described in example 1 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, *Tetrahedron: Asymmetry* 1999, 10, 1353-1367) was reacted with 4-benzyloxy-2,6-dimethyl-benzaldehyde in the presence of triethylamine and di-n-butylboron triflate to give (S)-4-benzyl-3-[(2S,3R)-3-(4-benzyloxy-2,6-dimethyl-phenyl)-2-ethoxy-3-hydroxy-propionyl]-oxazolidin-2-one as colorless liquid. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353-1367.

MS: 526.3 (M+Na)$^+$, 486.3, 425.3, 358.2, 309.1, 281.2, 253.1, 237.2, 178.2.

c] (2S,3R)-3-(4-Benzyloxy-2,6-dimethyl-phenyl)-2-ethoxy-3-hydroxy-propionic acid methyl ester In analogy to the procedure described in example 1 b], (S)-4-benzyl-3-[(2S,3R)-3-(4-benzyloxy-2,6-dimethyl-phenyl)-2-ethoxy-3-hydroxy-propionyl]-oxazolidin-2-one was treated with sodium methoxide in methanol to give (2S,3R)-3-(4-benzyloxy-2,6-dimethyl-phenyl)-2-ethoxy-3-hydroxy-propionic acid methyl ester as colorless liquid. According to $^1$H-NMR spectroscopy, one single diastereomer was obtained.

MS: 381.2 (M+Na)$^+$, 376.3 (M+NH$_4$)$^+$, 341.2, 313.2, 269.2, 213.3, 187.2.

d] (2S)-3-(4-Benzyloxy-2,6-dimethyl-phenyl)-2-ethoxy-propionic acid methyl ester In analogy to the procedure described in example 1 c], (2S,3R)-3-(4-benzyloxy-2,6-dimethyl-phenyl)-2-ethoxy-3-hydroxy-propionic acid methyl ester was treated with triethylsilane in trifluoroacetic acid to yield (2S)-3-(4-benzyloxy-2,6-dimethyl-phenyl)-2-ethoxy-propionic acid methyl ester as colorless liquid.

MS: 360.3 (M+NH$_4$)$^+$, 284.1, 269.2, 201.1, 163.3.

e] (2S)-2-Ethoxy-3-(4-hydroxy-2,6-dimethyl-phenyl)-propionic acid methyl ester In analogy to the procedure described in example 1 d], (2S)-3-(4-benzyloxy-2,6-dimethyl-phenyl)-2-ethoxy-propionic acid methyl ester was hydrogenated over 10% palladium on charcoal to give (2S)-2-ethoxy-3-(4-hydroxy-2,6-dimethyl-phenyl)-propionic acid methyl ester as colorless liquid.

MS: 275.2 (M+Na)⁺, 270.3 (M+NH₄)⁺, 253.3 (M+H)⁺, 207.2, 165.3.

f] (S)-3-[2,6-Dimethyl-4-(5-methyl-2-phenyl-oxazol-4-ylmethoxy)-phenyl]-2-ethoxy-propionic acid methyl ester In analogy to the procedure described in example 1 f], (2S)-2-ethoxy-3-(4-hydroxy-2,6-dimethyl-phenyl)-propionic acid methyl ester was reacted with 4-chloromethyl-5-methyl-2-phenyl-oxazole in the presence of cesium carbonate and potassium iodide to yield (S)-3-[2,6-dimethyl-4-(5-methyl-2-phenyl-oxazol-4-ylmethoxy)-phenyl]-2-ethoxy-propionic acid methyl ester as colorless liquid.
MS: 446.4 (M+Na)⁺, 357.0, 275.0, 169.1.

g] (S)-3-[2,6-Dimethyl-4-(5-methyl-2-phenyl-oxazol-4-ylmethoxy)-phenyl]-2-ethoxy-propionic acid In analogy to the procedure described in example 1 g], (S)-3-[2,6-dimethyl-4-(5-methyl-2-phenyl-oxazol-4-ylmethoxy)-phenyl]-2-ethoxy-propionic acid methyl ester was treated with LiOH to obtain (S)-3-[2,6-dimethyl-4-(5-methyl-2-phenyl-oxazol-4-ylmethoxy)-phenyl]-2-ethoxy-propionic acid as colorless solid.
MS: 432.2 (M+Na)⁺, 410.2 (M+H)⁺, 355.0, 329.4, 293.4, 244.3, 174.3, 166.3.

Example 30 a] (S)-2-Ethoxy-3-{4-[2-(4-isopropoxy-phenyl)-5-methyl-oxazol-4-ylmethoxy]-2,6-dimethyl-phenyl}-propionic acid methyl ester In analogy to the procedure described in example 1 f], (2S)-2-ethoxy-3-(4-hydroxy-2,6-dimethyl-phenyl)-propionic acid methyl ester (example 29 e]) was reacted with 4-chloromethyl-2-(4-isopropoxy-phenyl)-5-methyl-oxazole (example 2 b]) in the presence of cesium carbonate and potassium iodide to yield (S)-2-ethoxy-3-{4-[2-(4-isopropoxy-phenyl)-5-methyl-oxazol-4-ylmethoxy]-2,6-dimethyl-phenyl}-propionic acid methyl ester as colorless liquid.
MS: 504.3 (M+Na)⁺, 482.3 (M+H)⁺, 299.3, 271.2, 230.2, 188.3, 161.3.

b] (S)-2-Ethoxy-3-{4-[2-(4-isopropoxy-phenyl)-5-methyl-oxazol-4-ylmethoxy]-2,6-dimethyl-phenyl}-propionic acid In analogy to the procedure described in example 1 g], (S)-2-ethoxy-3-{4-[2-(4-isopropoxy-phenyl)-5-methyl-oxazol-4-ylmethoxy]-2,6-dimethyl-phenyl}-propionic acid methyl ester was treated with LiOH to obtain (S)-2-ethoxy-3-{4-[2-(4-isopropoxy-phenyl)-5-methyl-oxazol-4-ylmethoxy]-2,6-dimethyl-phenyl}-propionic acid as colorless foam.
MS: 490.2 (M+Na)⁺, 468.2 (M+H)⁺, 416.2, 305.2, 271.3, 230.2, 188.3.

Example 31 a] (S)-2-Ethoxy-3-{4-[2-(4-isopropyl-phenyl)-5-methyl-oxazol-4-ylmethoxy]-2,6-dimethyl-phenyl}-propionic acid methyl ester In analogy to the procedure described in example 1 f], (2S)-2-ethoxy-3-(4-hydroxy-2,6-dimethyl-phenyl)-propionic acid methyl ester (example 29 e]) was reacted with 4-chloromethyl-2-(4-isopropyl-phenyl)-5-methyl-oxazole (prepared from 4-isopropyl-benzaldehyde and diacetyl monoxyme followed by treatment with POCl₃ in analogy to the procedures described in examples 5 a] and 2 b]) in the presence of cesium carbonate and potassium iodide to yield (S)-2-ethoxy-3-{4-[2-(4-isopropyl-phenyl)-5-methyl-oxazol-4-ylmethoxy]-2,6-dimethyl-phenyl}-propionic acid methyl ester as colorless liquid.
MS: 488.3 (M+Na)⁺, 466.3 (M+H)⁺, 255.2, 214.4, 187.3.

b] (S)-2-Ethoxy-3-{4-[2-(4-isopropyl-phenyl)-5-methyl-oxazol-4-ylmethoxy]-2,6-dimethyl-phenyl}-propionic acid In analogy to the procedure described in example 1 g], (S)-2-ethoxy-3-{4-[2-(4-isopropyl-phenyl)-5-methyl-oxazol-4-ylmethoxy]-2,6-dimethyl-phenyl}-propionic acid methyl ester was treated with LiOH to obtain (S)-2-ethoxy-3-{4-[2-(4-isopropyl-phenyl)-5-methyl-oxazol-4-ylmethoxy]-2,6-dimethyl-phenyl}-propionic acid as colorless solid.
MS: 474.2 (M+Na)⁺, 452.3 (M+H)⁺, 400.4, 357.1, 279.2, 214.4.

Example 32 a] (S)-3-{4-[2-(3-Chloro-phenyl)-5-methyl-oxazol-4-ylmethoxy]-2,6-dimethyl-phenyl}-2-ethoxy-propionic acid methyl ester In analogy to the procedure described in example 1 f], (2S)-2-ethoxy-3-(4-hydroxy-2,6-dimethyl-phenyl)-propionic acid methyl ester (example 29 e]) was reacted with 4-chloromethyl-2-(3-chloro-phenyl)-5-methyl-oxazole (prepared from 3-chloro-benzaldehyde and diacetyl monoxyme followed by treatment with POCl₃ in analogy to the procedures described in examples 5 a] and 2 b]) in the presence of cesium carbonate and potassium iodide to yield (S)-3-{4-[2-(3-chloro-phenyl)-5-methyl-oxazol-4-ylmethoxy]-2,6-dimethyl-phenyl}-2-ethoxy-propionic acid methyl ester as colorless liquid.
MS: 480.3 (M+Na)⁺, 458.3 (M+H)⁺, 412.2, 330.2, 302.2, 247.2, 206.1.

b] (S)-3-{4-[2-(3-Chloro-phenyl)-5-methyl-oxazol-4-ylmethoxy]-2,6-dimethyl-phenyl}-2-ethoxy-propionic acid In analogy to the procedure described in example 1 g], (S)-3-{4-[2-(3-chloro-phenyl)-5-methyl-oxazol-4-ylmethoxy]-2,6-dimethyl-phenyl}-2-ethoxy-propionic acid methyl ester was treated with LiOH to obtain (S)-3-{4-[2-(3-chloro-phenyl)-5-methyl-oxazol-4-ylmethoxy]-2,6-dimethyl-phenyl}-2-ethoxy-propionic acid as colorless solid.
MS: 466.2 (M+Na)⁺, 444.2 (M+H)⁺, 380.2, 305.2, 287.2, 254.3, 215.3, 206.2, 198.2.

Example 33 a] (S)-2-Ethoxy-3-[4-[2-(4-fluoro-3-methyl-phenyl)-5-methyl-oxazol-4-ylmethoxy]-2,6-dimethyl-phenyl]-propionic acid methyl ester In analogy to the procedure described in example 1 f], (2S)-2-ethoxy-3-(4-hydroxy-2,6-dimethyl-phenyl)-propionic acid methyl ester (example 29 e]) was reacted with 4-chloromethyl-2-(4-fluoro-3-methyl-phenyl)-5-methyl-oxazole (example 5 b]) in the presence of cesium carbonate and potassium iodide to yield (S)-2-ethoxy-3-{4-[2-(4-fluoro-3-methyl-phenyl)-5-methyl-oxazol-4-ylmethoxy]-2,6-dimethyl-phenyl}-propionic acid methyl ester as colorless liquid.

MS: 478.3 (M+Na)+, 456.3 (M+H)+, 371.4, 339.1, 304.1, 245.3, 222.2, 204.2.

b] (S)-2-Ethoxy-3-{4-[2-(4-fluoro-3-methyl-phenyl)-5-methyl-oxazol-4-ylmethoxy]-2,6-dimethyl-phenyl}-propionic acid In analogy to the procedure described in example 1 g], (S)-2-ethoxy-3-{4-[2-(4-fluoro-3-methyl-phenyl)-5-methyl-oxazol-4-ylmethoxy]-2,6-dimethyl-phenyl}-propionic acid methyl ester was treated with LiOH to obtain (S)-2-ethoxy-3-{4-[2-(4-fluoro-3-methyl-phenyl)-5-methyl-oxazol-4-ylmethoxy]-2,6-dimethyl-phenyl}-propionic acid as colorless solid.

MS: 464.2 (M+Na)+, 442.3 (M+H)+, 349.3, 285.1, 266.2, 245.4, 225.3, 187.2.

Example 34 a] 3-(4-Benzyloxy-2-methyl-phenyl)-2(Z,E)-ethoxy-acrylic acid ethyl ester

A suspension of (1,2-diethoxy-2-oxoethyl)triphenyl phosphonium chloride [Tetrahedron 50(25), 7543-56(1994)] (35.5 g, 82.9 mmol) and DBU (13.6 ml, 91.2 mmol) in THF (60 ml) was stirred for 10 min at ambient temperature. 4-Benzyloxy-2-methyl-benzaldehyde (12.5 g, 55.2 mmol) was added and the reaction mixture was heated under reflux for 16 h. The solvent was concentrated at reduced pressure, the residue was taken up in AcOEt and washed with saturated aqueous NH$_4$Cl solution and brine. The organic layer was dried over sodium sulfate, the solvent removed under reduced pressure and the residue purified by column chromatography (silica gel, hexane/AcOEt) to give 14.5 g (42.6 mmol, 77%) of the title compound as yellow liquid.

MS: 340.2 (M)+, 249.2, 147.1, 91.1.

b] [rac]-2-Ethoxy-3-(4-hydroxy-2-methyl-phenyl)-propionic acid ethyl ester

A solution of 3-(4-benzyloxy-2-methyl-phenyl)-2(Z,E)-ethoxy-acrylic acid ethyl ester (1 g, 2.9 mmol) in ethanol (50 ml) was hydrogenated over 10% palladium on charcoal (250 mg) at ambient temperature for 2 h. The catalyst was filtered off and the solvent evaporated under reduced pressure to give 600 mg (2.4 mmol, 81%) of the title compound as yellow liquid which was used in the next step without further purification.

MS: 270.4 (M+NH$_4$)+, 253 (M)+, 207.2, 165.3.

c] [rac]-3-{4-[2-(3,5-Dichloro-phenyl)-5-methyl-oxazol-4-ylmethoxy]-2-methyl-phenyl}-2-ethoxy-propionic acid ethyl ester In analogy to the procedure described in example 1 f], [rac]-2-ethoxy-3-(4-hydroxy-2-methyl-phenyl)-propionic acid ethyl ester was reacted with 4-chloromethyl-2-(3,5-dichloro-phenyl)-5-methyl-oxazole (prepared from 3,5-dichloro-benzaldehyde and diacetyl monoxyme followed by treatment with POCl$_3$ in analogy to the procedures described in examples 2 a] and b]) in the presence of cesium carbonate and potassium iodide to yield [rac]-3-{4-[2-(3,5-dichloro-phenyl)-5-methyl-oxazol-4-ylmethoxy]-2-methyl-phenyl}-2-ethoxy-propionic acid ethyl ester as colorless liquid.

MS: 493.3 (M+H)+, 453.3, 375.4, 331.4, 275.2, 240.2, 200.2.

d] (S)-3-[4-[2-(3,5-Dichloro-phenyl)-5-methyl-oxazol-4-ylmethoxy]-2-methyl-phenyl]-2-ethoxy-propionic acid In analogy to the procedure described in example 1 g], [rac]-3-{4-[2-(3,5-dichloro-phenyl)-5-methyl-oxazol-4-ylmethoxy]-2-methyl-phenyl}-2-ethoxy-propionic acid ethyl ester was treated with LiOH to obtain [rac]-3-{4-[2-(3,5-dichloro-phenyl)-5-methyl-oxazol-4-ylmethoxy]-2-methyl-phenyl}-2-ethoxy-propionic acid as colorless liquid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 486.1 (M+Na)+, 466.1 (M+H)+, 464.2 (M+H)+, 433.1, 351.0, 293.2, 269.2, 187.2.

Example 35 a] [rac]-3-{4-[2-(3,5-Dimethyl-phenyl)-5-methyl-oxazol-4-ylmethoxy]-2-methyl-phenyl}-2-ethoxy-propionic acid ethyl ester In analogy to the procedure described in example 1 f], [rac]-2-ethoxy-3-(4-hydroxy-2-methyl-phenyl)-propionic acid ethyl ester (example 34 b]) was reacted with 4-chloromethyl-2-(3,5-dimethyl-phenyl)-5-methyl-oxazole (prepared from 3,5-dimethyl-benzaldehyde and diacetyl monoxyme followed by treatment with POCl$_3$ in analogy to the procedures described in examples 2 a] and b]) in the presence of cesium carbonate and potassium iodide to yield [rac]-3-{4-[2-(3,5-dimethyl-phenyl)-5-methyl-oxazol-4-ylmethoxy]-2-methyl-phenyl}-2-ethoxy-propionic acid ethyl ester as colorless liquid.

MS: 474.2 (M+Na)+, 452.3 (M+H)+, 431.4, 375.3, 331.3, 275.2, 241.3, 200.2.

b] (S)-3-{4-[2-(3,5-Dimethyl-phenyl)-5-methyl-oxazol-4-ylmethoxy]-2-methyl-phenyl}-2-ethoxy-propionic acid In analogy to the procedure described in example 1 g], [rac]-3-{4-[2-(3,5-dimethyl-phenyl)-5-methyl-oxazol-4-ylmethoxy]-2-methyl-phenyl}-2-ethoxy-propionic acid ethyl ester was treated with LiOH to obtain [rac]-3-{4-[2-(3,5-dimethyl-phenyl)-5-methyl-oxazol-4-ylmethoxy]-2-methyl-phenyl}-2-ethoxy-propionic acid as colorless liquid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 422.3 (M−H)−, 375.9, 339.2, 319.3, 305.6, 282.2, 255.4, 222.9.

Example 36 a] [rac]-2-Ethoxy-3-{2-methyl-4-[5-methyl-2-(2-trifluoromethyl-phenyl)-oxazol-4-ylmethoxy]-phenyl}-propionic acid ethyl ester In analogy to the procedure described in example 1 f], [rac]-2-ethoxy-3-(4-hydroxy-2-methyl-phenyl)-propionic acid ethyl ester (example 34 b]) was reacted with 4-chloromethyl-5-methyl-2-(2-trifluoromethyl-phenyl)-oxazole (prepared from 2-trifluoromethyl-benzaldehyde and diacetyl monoxyme followed by treatment with POCl$_3$ in analogy to the procedures described in examples 5 a] and 2 b]) in the presence of cesium carbonate and potassium iodide to yield [rac]-2-ethoxy-3-{2-methyl-4-[5-methyl-2-(2-trifluoromethyl-phenyl)-oxazol-4-ylmethoxy]-phenyl}-propionic acid ethyl ester as colorless liquid.

MS: 514.2 (M+Na)$^+$, 492.2 (M+H)$^+$, 448.2, 407.2, 322.2, 281.1, 266.3, 240.2.

b] (S)-2-Ethoxy-3-{2-methyl-4-[5-methyl-2-(2-trifluoromethyl-phenyl)-oxazol-4-ylmethoxy]-phenyl}-propionic acid In analogy to the procedure described in example 1 g], [rac]-2-ethoxy-3-{2-methyl-4-[5-methyl-2-(2-trifluoromethyl-phenyl)-oxazol-4-ylmethoxy]-phenyl}-propionic acid ethyl ester was treated with LiOH to obtain [rac]-2-ethoxy-3-{2-methyl-4-[5-methyl-2-(2-trifluoromethyl-phenyl)-oxazol-4-ylmethoxy]-phenyl}-propionic acid as colorless liquid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 462.2 (M–H)$^-$, 416.4, 372.1, 353.4, 337.3, 309.5, 255.0, 223.0.

Example 37 a] [rac]-2-Ethoxy-3-{2-methyl-4-[5-methyl-2-(3-trifluoromethyl-phenyl)-oxazol-4-ylmethoxy]-phenyl}-propionic acid ethyl ester In analogy to the procedure described in example 1 f], [rac]-2-ethoxy-3-(4-hydroxy-2-methyl-phenyl)-propionic acid ethyl ester (example 34 b]) was reacted with 4-chloromethyl-5-methyl-2-(3-trifluoromethyl-phenyl)-oxazole (prepared from 3-trifluoromethyl-benzaldehyde and diacetyl monoxyme followed by treatment with POCl$_3$ in analogy to the procedures described in examples 5 a] and 2 b]) in the presence of cesium carbonate and potassium iodide to yield [rac]-2-ethoxy-3-{2-methyl-4-[5-methyl-2-(3-trifluoromethyl-phenyl)-oxazol-4-ylmethoxy]-phenyl}-propionic acid ethyl ester as colorless liquid.

MS: 514.3 (M+Na)$^+$, 509.4 (M+NH$_4$)$^+$, 492.2 (M+H)$^+$, 446.1, 281.1, 240.2.

b] (S)-2-Ethoxy-3-{2-methyl-4-[5-methyl-2-(3-trifluoromethyl-phenyl)-oxazol-4-ylmethoxy]-phenyl}-propionic acid In analogy to the procedure described in example 1 g], [rac]-2-ethoxy-3-{2-methyl-4-[5-methyl-2-(3-trifluoromethyl-phenyl)-oxazol-4-ylmethoxy]-phenyl}-propionic acid ethyl ester was treated with LiOH to obtain [rac]-2-ethoxy-3-{2-methyl-4-[5-methyl-2-(3-trifluoromethyl-phenyl)-oxazol-4-ylmethoxy]-phenyl}-propionic acid as colorless solid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 462.1 (M–H)$^-$, 404.8, 387.0, 353.2, 319.0, 282.9, 268.7, 255.2, 241.0, 226.9.

Example 38 a] [rac]-2-Ethoxy-3-{4-[2-(4-fluoro-phenyl)-5-methyl-oxazol-4-ylmethoxy]-2-methyl-phenyl}-propionic acid ethyl ester In analogy to the procedure described in example 1 f], [rac]-2-ethoxy-3-(4-hydroxy-2-methyl-phenyl)-propionic acid ethyl ester (example 34 b]) was reacted with 4-chloromethyl-2-(4-fluoro-phenyl)-5-methyl-oxazole (prepared from 4-fluoro-benzaldehyde and diacetyl monoxyme followed by treatment with POCl$_3$ in analogy to the procedures described in examples 2 a] and b]) in the presence of cesium carbonate and potassium iodide to yield [rac]-2-ethoxy-3-{4-[2-(4-fluoro-phenyl)-5-methyl-oxazol-4-ylmethoxy]-2-methyl-phenyl}-propionic acid ethyl ester as colorless liquid.

MS: 442.2 (M+H)$^+$, 391.2, 319.3, 231.2, 198.2, 190.3, 181.2, 166.3.

b] (S)-2-Ethoxy-3-{4-[2-(4-fluoro-phenyl)-5-methyl-oxazol-4-ylmethoxy]-2-methyl-phenyl}-propionic acid In analogy to the procedure described in example 1 g], [rac]-2-ethoxy-3-{4-[2-(4-fluoro-phenyl)-5-methyl-oxazol-4-ylmethoxy]-2-methyl-phenyl}-propionic acid ethyl ester was treated with LiOH to obtain [rac]-2-ethoxy-3-{4-[2-(4-fluoro-phenyl)-5-methyl-oxazol-4-ylmethoxy]-2-methyl-phenyl}-propionic acid as colorless liquid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 412.2 (M–H)$^-$, 366.0, 322.3, 303.1, 283.3, 254.8, 222.9, 194.6.

Example 39 a] [rac]-2-Ethoxy-3-{2-methyl-4-[5-methyl-2-(4-trifluoromethyl-phenyl)-oxazol-4-ylmethoxy]-phenyl}-propionic acid ethyl ester In analogy to the procedure described in example 1 f], [rac]-2-ethoxy-3-(4-hydroxy-2-methyl-phenyl)-propionic acid ethyl ester (example 34 b]) was reacted with 4-chloromethyl-5-methyl-2-(4-trifluoromethyl-phenyl)-oxazole (prepared from 4-trifluoromethyl-benzaldehyde and diacetyl monoxyme followed by treatment with POCl$_3$ in analogy to the procedures described in examples 2 a] and b]) in the presence of cesium carbonate and potassium iodide to yield [rac]-2-ethoxy-3-{2-methyl-4-[5-methyl-2-(4-trifluoromethyl-phenyl)-oxazol-4-ylmethoxy]-phenyl}-propionic acid ethyl ester as colorless liquid.

MS: 514.2 (M+Na)$^+$, 509.4 (M+NH$_4$)$^+$, 492.2 (M+H)$^+$, 446.2, 418.2, 281.1, 240.2, 172.2 b] (S)-2-Ethoxy-3-{2-methyl-4-[5-methyl-2-(4-trifluoromethyl-phenyl)-oxazol-4-ylmethoxy]-phenyl}-propionic acid In analogy to the procedure described in example 1 g], [rac]-2-ethoxy-3-{2-methyl-4-[5-methyl-2-(4-trifluoromethyl-phenyl)-oxazol-4-ylmethoxy]-phenyl}-propionic acid ethyl ester was treated with LiOH to obtain [rac]-2-ethoxy-3-{2-methyl-4-[5-methyl-2-(4-trifluoromethyl-phenyl)-oxazol-4-ylmethoxy]-phenyl}-propionic acid as colorless solid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 462.2 (M–H)$^-$, 416.2, 399.1, 372.3, 341.7, 317.1, 255.4.

Example 40 a] [rac]-2-Ethoxy-3-{4-[2-(4-isopropyl-phenyl)-5-methyl-oxazol-4-ylmethoxy]-2-methyl-phenyl}-propionic acid ethyl ester In analogy to the procedure described in example 1 f], [rac]-2-ethoxy-3-(4-hydroxy-2-methyl-phenyl)-propionic acid ethyl ester (example 34 b]) was reacted with 4-chloromethyl-2-(4-isopropyl-phenyl)-5-methyl-oxazole (prepared from 4-isopropyl-benzaldehyde and diacetyl monoxyme followed by treatment with POCl$_3$ in analogy to the procedures described in examples 5 a] and 2 b]) in the presence of cesium carbonate and potassium iodide to yield [rac]-2-ethoxy-3-{4-[2-(4-isopropyl-phenyl)-5-methyl-oxazol-4-ylmethoxy]-2-methyl-phenyl}-propionic acid ethyl ester as colorless liquid.

MS: 488.3 (M+Na)$^+$, 466.2 (M+H)$^+$, 422.3, 391.2, 279.2, 214.4.

b] (S)-2-Ethoxy-3-{4-[2-(4-isopropyl-phenyl)-5-methyl-oxazol-4-ylmethoxy]-2-methyl-phenyl}-propionic acid In analogy to the procedure described in example 1 g], [rac]-2-ethoxy-3-{4-[2-(4-isopropyl-phenyl)-5-methyl-oxazol-4-ylmethoxy]-2-methyl-phenyl}-propionic acid ethyl ester was treated with LiOH to obtain [rac]-2-ethoxy-3-{4-[2-(4-isopropyl-phenyl)-5-methyl-oxazol-4-ylmethoxy]-2-methyl-phenyl}-propionic acid as colorless liquid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 436.2 (M–H)$^-$, 410.9, 389.8, 363.3, 328.7, 305.0, 282.9, 254.9, 222.8.

Example 41 a] [rac]-2-Ethoxy-3-{2-methyl-4-[5-methyl-2-(3,4,5-trimethoxy-phenyl)-oxazol-4-ylmethoxy]-phenyl}-propionic acid ethyl ester In analogy to the procedure described in example 1 f], [rac]-2-ethoxy-3-(4-hydroxy-2-methyl-phenyl)-propionic acid ethyl ester (example 34 b]) was reacted with 4-chloromethyl-5-methyl-2-(3,4,5-trimethoxy-phenyl)-oxazole (prepared from 3,4,5-trimethoxy-benzaldehyde and diacetyl monoxyme followed by treatment with POCl$_3$ in analogy to the procedures described in examples 2 a] and b]) in the presence of cesium carbonate and potassium iodide to yield [rac]-2-ethoxy-3-{2-methyl-4-[5-methyl-2-(3,4,5-trimethoxy-phenyl)-oxazol-4-ylmethoxy]-phenyl}-propionic acid ethyl ester as yellow liquid.

MS: 536.3 (M+Na)$^+$, 514.3 (M+H)$^+$, 470.2, 340.0, 303.2, 262.2, 214.3, 168.2.

b] (S)-2-Ethoxy-3-{2-methyl-4-[5-methyl-2-(3,4,5-trimethoxy-phenyl)-oxazol-4-ylmethoxy]-phenyl}-propionic acid In analogy to the procedure described in example 1 g], [rac]-2-ethoxy-3-{2-methyl-4-[5-methyl-2-(3,4,5-trimethoxy-phenyl)-oxazol-4-ylmethoxy]-phenyl}-propionic acid ethyl ester was treated with LiOH to obtain [rac]-2-ethoxy-3-{2-methyl-4-[5-methyl-2-(3,4,5-trimethoxy-phenyl)-oxazol-4-ylmethoxy]-phenyl}-propionic acid as colorless solid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 485.3 (M)$^-$.

Example 42 a] [rac]-2-Ethoxy-3-(4-{2-[2-(2-ethoxy-4-fluoro-phenyl)-5-methyl-oxazol-4-yl]-ethoxy}-2-methyl-phenyl)-propionic acid ethyl ester In analogy to the procedure described in example 7 c], [rac]-2-ethoxy-3-(4-hydroxy-2-methyl-phenyl)-propionic acid ethyl ester (example 34 b]) was reacted with 2-[2-(2-ethoxy-4-fluoro-phenyl)-5-methyl-oxazol-4-yl]-ethanol (prepared from 4-fluoro-2-hydroxy-benzaldehyde [J. Chem. Soc., Perkin Trans. 1 (1994), (13), 1823-31] by i) treatment with ethyl iodide, potassium carbonate in N,N-dimethylformamide to give 2-ethoxy-4-fluoro-benzaldehyde; ii) conversion of 2-ethoxy-4-fluoro-benzaldehyde into 4-chloromethyl-2-(2-ethoxy-4-fluoro-phenyl)-5-methyl-oxazole in analogy to the procedures described in examples 2 a] and b]; iii) conversion of 4-chloromethyl-2-(2-ethoxy-4-fluoro-phenyl)-5-methyl-oxazole into 2-[2-(2-ethoxy-4-fluoro-phenyl)-5-methyl-oxazol-4-yl]-ethanol by treatment with sodium cyanide in DMSO followed by hydrolysis of the nitrile function with sodium hydroxide in ethanol/water at reflux and reduction of the acid formed with BH$_3$xTHF in tetrahydrofuran at room temperature) in the presence of triphenylphosphine and diethyl azodicarboxylate to yield [rac]-2-ethoxy-3-(4-{2-[2-(2-ethoxy-4-fluoro-phenyl)-5-methyl-oxazol-4-yl]-ethoxy}-2-methyl-phenyl)-propionic acid ethyl ester as light yellow liquid.

MS: 522.2 (M+Na)$^+$, 500.3 (M+H)$^+$, 456.3, 426.3, 398.2, 248.2, 220.2, 149.1.

b] (S)-2-Ethoxy-3-(4-{2-[2-(2-ethoxy-4-fluoro-phenyl)-5-methyl-oxazol-4-yl]-ethoxy}-2-methyl-phenyl)-propionic acid In analogy to the procedure described in example 1 g], [rac]-2-ethoxy-3-(4-{2-[2-(2-ethoxy-4-fluoro-phenyl)-5-methyl-oxazol-4-yl]-ethoxy}-2-methyl-phenyl)-propionic acid ethyl ester was treated with LiOH to obtain [rac]-2-ethoxy-3-(4-{2-[2-(2-ethoxy-4-fluoro-phenyl)-5-methyl-oxazol-4-yl]-ethoxy}-2-methyl-phenyl)-propionic acid as colorless solid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 470.1 (M–H)$^-$, 424.2, 387.0, 326.5, 281.1, 255.0, 204.9.

Example 43 a] [rac]-2-Ethoxy-3-{2-methyl-4-[3-(5-methyl-2-phenyl-oxazol-4-yl)-propoxy]-phenyl}-propionic acid ethyl ester In analogy to the procedure described in example 7 c], [rac]-2-ethoxy-3-(4-hydroxy-2-methyl-phenyl)-propionic acid ethyl ester (example 34 b]) was reacted with 3-(5-methyl-2-phenyl-oxazol-4-yl)-propan-1-ol (J. L. Collins, M. Dezube, J. A. Oplinger, A. Jeffrey, T. M. Willson, International Patent Appl., Publication No. WO0008002(A1), 2000) in the presence of triphenylphosphine and diethyl azodicarboxylate to yield [rac]-2-ethoxy-3-{2-methyl-4-[3-(5-methyl-2-phenyl-oxazol-4-yl)-propoxy]-phenyl}-propionic acid ethyl ester as yellow liquid.

MS: 474.3 (M+Na)$^+$, 452.5 (M+H)$^+$, 382.4, 241.3.

b] (S)-2-Ethoxy-3-{2-methyl-4-[3-(5-methyl-2-phenyl-oxazol-4-yl)-propoxy]-phenyl}-propionic acid In analogy to the procedure described in example 1 g], [rac]-2-ethoxy-3-{2-methyl-4-[3-(5-methyl-2-phenyl-oxazol-4-yl)-propoxy]-phenyl}-propionic acid ethyl ester was treated with LiOH to obtain [rac]-2-ethoxy-3-{2-methyl-4-[3-(5-methyl-2-phenyl-oxazol-4-yl)-propoxy]-phenyl}-propionic acid as colorless liquid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 422.3 (M–H)$^-$, 376.3, 299.1.

Example 44 a] (S)-2-Ethoxy-3-[2-methyl-4-(2-phenyl-oxazol-4-ylmethoxy)-phenyl]-propionic acid methyl ester In analogy to the procedure described in example 1 f], (S)-2-ethoxy-3-(4-hydroxy-2-methyl-phenyl)-propionic acid ethyl ester (example 1 d]) was reacted with 4-chloromethyl-2-phenyl-oxazole [prepared from benzamide and 1,3-dichloroacetone as described in Bioorg. Med. Chem. Lett. (2000), 10(17), 2041-2044] in the presence of cesium carbonate and potassium iodide to yield (S)-2-ethoxy-3-[2-methyl-4-(2-phenyl-oxazol-4-ylmethoxy)-phenyl]-propionic acid methyl ester as colorless liquid.

MS: 418.2 (M+Na)$^+$, 396.2 (M+H)$^+$, 350.2, 336.3, 308.1, 251.2, 186.3, 158.2.

b] (S)-2-Ethoxy-3-[2-methyl-4-(2-phenyl-oxazol-4-ylmethoxy)-phenyl]-propionic acid In analogy to the procedure described in example 1 g], (S)-2-ethoxy-3-[2-methyl-4-(2-phenyl-oxazol-4-ylmethoxy)-phenyl]-propionic acid methyl ester was treated with LiOH to obtain (S)-2-ethoxy-3-[2-methyl-4-(2-phenyl-oxazol-4-ylmethoxy)-phenyl]-propionic acid as colorless solid.

MS: 404.3 (M+Na)$^+$, 382.2 (M+H)$^+$, 325.2, 293.2, 250.2, 212.3, 172.3, 158.2.

Example 45 a] [rac]-3-{4-[2-(2-Chloro-phenyl)-oxazol-4-ylmethoxy]-2-methyl-phenyl}-2-ethoxy-propionic acid ethyl ester In analogy to the procedure described in example 1 f], [rac]-2-ethoxy-3-(4-hydroxy-2-methyl-phenyl)-propionic acid ethyl ester (example 34 b]) was reacted with 4-chloromethyl-2-(2-chloro-phenyl)-oxazole [prepared from 2-chloro-benzamide and 1,3-dichloroacetone in analogy to the procedure described for the synthesis of 4-chloromethyl-2-phenyl-oxazole in Bioorg. Med. Chem. Lett. (2000), 10(17), 2041-2044] in the presence of cesium carbonate and potassium iodide to yield [rac]-3-{4-[2-(2-chloro-phenyl)-oxazol-4-ylmethoxy]-2-methyl-phenyl}-2-ethoxy-propionic acid-ethyl ester as colorless liquid.

MS: 466.1 (M+Na)$^+$, 444.2 (M+H)$^+$, 371.4, 327.0, 192.2, 163.4.

b] (S)-3-{4-[2-(2-Chloro-phenyl)-oxazol-4-ylmethoxy]-2-methyl-phenyl}-2-ethoxy-propionic acid In analogy to the procedure described in example 1 g], [rac]-3-{4-[2-(2-chloro-phenyl)-oxazol-4-ylmethoxy]-2-methyl-phenyl}-2-ethoxy-propionic acid ethyl ester was treated with LiOH to obtain [rac]-3-{4-[2-(2-chloro-phenyl)-oxazol-4-ylmethoxy]-2-methyl-phenyl}-2-ethoxy-propionic acid as colorless liquid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 438.2 (M+Na)⁺, 416.1 (M+H)⁺, 340.4, 280.2, 220.4, 192.2, 173.1.

Example 46 a] [rac]-2-Ethoxy-3-{4-[2-(3-methoxy-phenyl)-oxazol-4-ylmethoxy]-2-methyl-phenyl}-propionic acid ethyl ester In analogy to the procedure described in example 1 f], [rac]-2-ethoxy-3-(4-hydroxy-2-methyl-phenyl)-propionic acid ethyl ester (example 34 b]) was reacted with 4-chloromethyl-2-(3-methoxy-phenyl)-oxazole [prepared from 3-methoxy-benzamide and 1,3-dichloroacetone in analogy to the procedure described for the synthesis of 4-chloromethyl-2-phenyl-oxazole in Bioorg. Med. Chem. Lett. (2000), 10(17), 2041-2044] in the presence of cesium carbonate and potassium iodide to yield [rac]-2-ethoxy-3-{4-[2-(3-methoxy-phenyl)-oxazol-4-ylmethoxy]-2-methyl-phenyl}-propionic acid ethyl ester as colorless liquid.

MS: 462.2 (M+Na)⁺, 440.2 (M+H)⁺, 394.2, 366.2, 291.4.

b] (S)-2-Ethoxy-3-{4-[2-(3-methoxy-phenyl)-oxazol-4-ylmethoxy]-2-methyl-phenyl}-propionic acid In analogy to the procedure described in example 1 g], [rac]-2-ethoxy-3-{4-[2-(3-methoxy-phenyl)-oxazol-4-ylmethoxy]-2-methyl-phenyl}-propionic acid ethyl ester was treated with LiOH to obtain [rac]-2-ethoxy-3-{4-[2-(3-methoxy-phenyl)-oxazol-4-ylmethoxy]-2-methyl-phenyl}-propionic acid as colorless liquid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 434.3 (M+Na)⁺, 412.2 (M+H)⁺, 360.1, 304.1, 261.2, 229.2, 188.3, 160.3.

Example 47 a] [rac]-3-(4-Benzyloxy-2-ethoxy-phenyl)-2-ethoxy-3-hydroxy-propionic acid ethyl ester [mixture of diastereomers]

LDA was prepared by adding 13.3 ml n-BuLi (1.5 M, hexane) to a solution of 2.85 ml (20.0 mmol) of diisopropylamine in 90 ml of abs. THF at −5° C. After cooling to −78° C., 2.81 ml (20.0 mmol) of ethyl ethoxyacetate, dissolved in 10 ml of abs. THF, was added and the mixture kept for 15 minutes at that temperature to ensure complete deprotonation. 2.05 g (8.0 mmol) of 4-benzyloxy-2-ethoxy-benzaldehyde [prepared from 2-hydroxy-4-benzyloxy-benzaldehyde and ethyl iodide in analogy to the procedure described for 4-benzyloxy-2-isopropoxy-benzaldehyde in Chemical & Pharmaceutical Bulletin (1998), 46(2), 222-230: 2-hydroxy-4-benzyloxy-benzaldehyde, isopropyl bromide, potassium iodide, potassium carbonate, N,N-dimethylformamide, 100° C.], dissolved in 20 ml of abs. THF, was then added. After stirring for 30 minutes at dry ice temperature, the reaction mixture was quenched with ammonium chloride solution, warmed up to 0° C., then extracted twice with AcOEt, washed with water, dried over sodium sulfate, and evaporated to dryness. Flash chromatography (SiO₂, hexane/AcOEt=9:1 to 1:1) yielded 3.09 g (99% of theory) of [rac]-3-(4-benzyloxy-2-ethoxy-phenyl)-2-ethoxy-3-hydroxy-propionic acid ethyl ester [mixture of diastereomers] as light yellow oil.

MS: 371.4 [(M+H)⁺–H₂O].

b] 3-(4-Benzyloxy-2-ethoxy-phenyl)-2(Z,E)-ethoxy-acrylic acid ethyl ester 3.26 g (8.39 mmol) of [rac]-3-(4-benzyloxy-2-ethoxy-phenyl)-2-ethoxy-3-hydroxy-propionic acid ethyl ester [mixture of diastereomers] and 0.15 g (0.84 mmol) 4-toluene sulfonic acid were stirred in 200 ml benzene at reflux for 30 minutes. Evaporation to dryness followed by flash chromatography (SiO₂, hexane/AcOEt=95:5 to 4:1) yielded 2.12 g (68% of theory) of 3-(4-benzyloxy-2-ethoxy-phenyl)-2(Z,E)-ethoxy-acrylic acid ethyl ester as light yellow oil.

MS: 370.1 (M)⁺.

c] [rac]-2-Ethoxy-3-(2-ethoxy-4-hydroxy-phenyl)-propionic acid ethyl ester 0.90 g of Pd/C (10%) were added under argon to 4.49 g (12.1 mmol) of 3-(4-benzyloxy-2-ethoxy-phenyl)-2(Z,E)-ethoxy-acrylic acid ethyl ester dissolved in 80 ml of ethanol. The atmosphere was then replaced with H₂, and the suspension was rapidly stirred at room temperature for two hours. Filtration over dicalite and evaporation of the solvents left 4.23 g of a light brown oil. Flash chromatography (SiO₂, hexane/AcOEt=95:5 to 1:1) yielded 3.41 g (99% of theory) of [rac]-2-ethoxy-3-(2-ethoxy-4-hydroxy-phenyl)-propionic acid ethyl ester as light yellow oil.

MS: 281.0 (M–H)⁻.

d] (S)-3-{4-[2-(4-tert-Butyl-phenyl)-5-methyl-oxazol-4-ylmethoxy]-2-ethoxy-phenyl}-2-ethoxy-propionic acid In analogy to the procedure described in example 1 f], [rac]-2-ethoxy-3-(2-ethoxy-4-hydroxy-phenyl)-propionic acid ethyl ester was reacted with 2-(4-tert-butyl-phenyl)-4-chloromethyl-5-methyl-oxazole (prepared from 4-tert-butyl-benzaldehyde and diacetyl monoxyme followed by treatment with POCl₃ in analogy to the procedures described in examples 5 a] and 2 b]) in N,N-dimethylformamide in the presence of potassium carbonate to yield [rac]-3-{4-[2-(4-tert-butyl-phenyl)-5-methyl-oxazol-4-ylmethoxy]-2-ethoxy-phenyl}-2-ethoxy-propionic acid ethyl ester, which was further saponified in analogy to the procedure described in example 1 g], to yield [rac]-3-{4-[2-(4-tert-butyl-phenyl)-5-methyl-oxazol-4-ylmethoxy]-2-ethoxy-phenyl}-2-ethoxy-propionic acid as colorless amorphous solid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 480.4 (M–H)⁻.

Example 48

(S)-2-Ethoxy-3-{2-ethoxy-4-[2-(4-isopropoxy-phenyl)-5-methyl-oxazol-4-ylmethoxy]-phenyl}-propionic acid In analogy to the procedure described in example 1 f], [rac]-2-ethoxy-3-(2-ethoxy-4-hydroxy-phenyl)-propionic acid ethyl ester (example 47 c]) was reacted with 4-chloromethyl-2-(4-isopropoxy-phenyl)-5-methyl-oxazole (example 2 b]) in N,N-dimethylformamide in the presence of potassium carbonate to yield [rac]-2-ethoxy-3-{2-ethoxy-4-[2-(4-isopropoxy-phenyl)-5-methyl-oxazol-4-ylmethoxy]-phenyl}-propionic acid ethyl ester, which was further saponified in analogy to the procedure described in example 1 g], to yield [rac]-2-ethoxy-3-{2-ethoxy-4-[2-(4-isopropoxy-phenyl)-5-methyl-oxazol-4-ylmethoxy]-phenyl}-propionic acid as colorless solid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 482.3 (M−H)⁻.

Example 49

(S)-3-[4-[2-(3-Chloro-phenyl)-5-methyl-oxazol-4-ylmethoxy]-2-ethoxy-phenyl]-2-ethoxy-propionic acid In analogy to the procedure described in example 1 f], [rac]-2-ethoxy-3-(2-ethoxy-4-hydroxy-phenyl)-propionic acid ethyl ester (example 47 c]) was reacted with 4-chloromethyl-2-(3-chloro-phenyl)-5-methyl-oxazole (prepared from 3-chloro-benzaldehyde and diacetyl monoxyme followed by treatment with POCl₃ in analogy to the procedures described in examples 5 a] and 2 b]) in N,N-dimethylformamide in the presence of potassium carbonate to yield [rac]-3-{4-[2-(3-chloro-phenyl)-5-methyl-oxazol-4-ylmethoxy]-2-ethoxy-phenyl}-2-ethoxy-propionic acid ethyl ester, which was further saponified in analogy to the procedure described in example 1 g], to yield [rac]-3-{4-[2-(3-chloro-phenyl)-5-methyl-oxazol-4-ylmethoxy]-2-ethoxy-phenyl}-2-ethoxy-propionic acid as colorless solid, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 458.2 (M−H)⁻.

Example 50

(S)-2-Ethoxy-3-{2-ethoxy-4-[2-(5-methyl-2-phenyl-oxazol-4-yl)-ethoxy]-phenyl}-propionic acid In analogy to the procedure described in example 7 c], [rac]-2-ethoxy-3-(2-ethoxy-4-hydroxy-phenyl)-propionic acid ethyl ester (example 47 c]) was reacted with 2-(5-methyl-2-phenyl-oxazol-4-yl)-ethanol in tetrahydrofuran in the presence of triphenylphosphine and DBAD (di-tert-butyl azodicarboxylate) to yield [rac]-2-ethoxy-3-{2-ethoxy-4-[2-(5-methyl-2-phenyl-oxazol-4-yl)-ethoxy]-phenyl}-propionic acid ethyl ester, which was further saponified in analogy to the procedure described in example 1 g], to yield [rac]-2-ethoxy-3-{2-ethoxy-4-[2-(5-methyl-2-phenyl-oxazol-4-yl)-ethoxy]-phenyl}-propionic acid as colorless oil, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 438.2 (M−H)⁻.

Example 51

(S)-2-Ethoxy-3-{2-ethoxy-4-[3-(5-methyl-2-phenyl-oxazol-4-yl)-propoxy]-phenyl}-propionic acid In analogy to the procedure described in example 7 c], [rac]-2-ethoxy-3-(2-ethoxy-4-hydroxy-phenyl)-propionic acid ethyl ester (example 47 c]) was reacted with 3-(5-methyl-2-phenyl-oxazol-4-yl)-propan-1-ol (J. L. Collins, M. Dezube, J. A. Oplinger, A. Jeffrey, T. M. Willson, International Patent Appl., Publication No. WO0008002(A1), 2000) in tetrahydrofuran in the presence of triphenylphosphine and DBAD (di-tert-butyl azodicarboxylate) to yield [rac]-2-ethoxy-3-{2-ethoxy-4-[3-(5-methyl-2-phenyl-oxazol-4-yl)-propoxy]-phenyl}-propionic acid ethyl ester, which was further saponified in analogy to the procedure described in example 1 g], to yield [rac]-2-ethoxy-3-{2-ethoxy-4-[3-(5-methyl-2-phenyl-oxazol-4-yl)-propoxy]-phenyl}-propionic acid as colorless oil, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 452.2 (M−H)⁻.

Example 52 a] [rac]-3-(4-Benzyloxy-2-isopropoxy-phenyl)-2-ethoxy-3-hydroxy-propionic acid ethyl ester [mixture of diastereomers]

In analogy to the procedure described in example 47 a], 4-benzyloxy-2-isopropoxy-benzaldehyde [Chemical & Pharmaceutical Bulletin (1998), 46(2), 222-230] was reacted with the enolate of ethyl ethoxyacetate, to yield [rac]-3-(4-benzyloxy-2-isopropoxy-phenyl)-2-ethoxy-3-hydroxy-propionic acid ethyl ester as a mixture of diastereomers in form of a light yellow oil.

MS: 402.0 (M)⁺.

b] [rac]-2-Ethoxy-3-(4-hydroxy-2-isopropoxy-phenyl)-propionic acid ethyl ester 0.80 g of Pd/C (10%) and 6.0 g of oxalic acid dihydrate were added under argon to 3.20 g (7.95 mmol) of [rac]-3-(4-benzyloxy-2-isopropoxy-phenyl)-2-ethoxy-3-hydroxy-propionic acid ethyl ester [mixture of diastereomers] dissolved in 60 ml of isopropanol. This solution was stirred for 24 hours at room temperature and 50 bar H$_2$. Filtration over dicalite and evaporation of the solvents, followed by flash chromatography (SiO$_2$, hexane/AcOEt=9:1 to 1:1) left 0.69 g (29% of theory) of [rac]-2-ethoxy-3-(4-hydroxy-2-isopropoxy-phenyl)-propionic acid ethyl ester as yellow oil.

MS: 295.2 (M−H)$^-$.

c] (S)-3-{4-[2-(4-tert-Butyl-phenyl)-5-methyl-oxazol-4-ylmethoxy]-2-isopropoxy-phenyl}-2-ethoxy-propionic acid In analogy to the procedure described in example 1 f], [rac]-2-ethoxy-3-(4-hydroxy-2-isopropoxy-phenyl)-propionic acid ethyl ester was reacted with 2-(4-tert-butyl-phenyl)-4-chloromethyl-5-methyl-oxazole (prepared from 4-tert-butyl-benzaldehyde and diacetyl monoxyme followed by treatment with POCl$_3$ in analogy to the procedures described in examples 5 a] and 2 b]) in N,N-dimethylformamide in the presence of potassium carbonate to yield [rac]-3-{4-[2-(4-tert-butyl-phenyl)-5-methyl-oxazol-4-ylmethoxy]-2-isopropoxy-phenyl}-2-ethoxy-propionic acid ethyl ester, which was further saponified in analogy to the procedure described in example 1 g], to yield [rac]-3-{4-[2-(4-tert-butyl-phenyl)-5-methyl-oxazol-4-ylmethoxy]-2-isopropoxy-phenyl}-2-ethoxy-propionic acid as colorless viscous oil, which can be separated into its antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine and quinidine or by separation of the antipodes by specific chromatographic methods using either a chiral adsorbens or a chiral eluent to give the title compound.

MS: 494.3 (M−H)$^-$.

Example 53 a] (S)-2-Ethoxy-3-[2-fluoro-4-(5-methyl-2-o-tolyl-oxazol-4-ylmethoxy)-phenyl]-propionic acid methyl ester In analogy to the procedure described in example 1 f], (2S)-2-ethoxy-3-(2-fluoro-4-hydroxy-phenyl)-propionic acid methyl ester (example 13 f]) was reacted with 4-chloromethyl-5-methyl-2-o-tolyl-oxazole (example 1 e]) in the presence of cesium carbonate and potassium iodide to yield (S)-2-ethoxy-3-[2-fluoro-4-(5-methyl-2-o-tolyl-oxazol-4-ylmethoxy)-phenyl]-propionic acid methyl ester as colorless oil.

MS: 450.4 (M+Na)$^+$, 445.4 (M+NH$_4$)$^+$, 428.5 (M+H)$^+$, 391.4, 279.3, 227.4, 186.3.

b] (S)-2-Ethoxy-3-[2-fluoro-4-(5-methyl-2-o-tolyl-oxazol-4-ylmethoxy)-phenyl]-propionic acid In analogy to the procedure described in example 1 g], (S)-2-ethoxy-3-[2-fluoro-4-(5-methyl-2-o-tolyl-oxazol-4-ylmethoxy)-phenyl]-propionic acid methyl ester was treated with LiOH to obtain (S)-2-ethoxy-3-[2-fluoro-4-(5-methyl-2-o-tolyl-oxazol-4-ylmethoxy)-phenyl]-propionic acid as colorless liquid.

MS: 412.2 (M−H)$^-$, 366.2.

Example A

Tablets containing the following ingredients can be manufactured in a conventional manner:

| Ingredients | Per tablet |
| --- | --- |
| Compound of formula (I) | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

Example C

Injection solutions can have the following composition:

| | |
| --- | --- |
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

The invention claimed is:

1. A method for the treatment of a disease selected from the group consisting of diabetes, non-insulin dependent diabetes mellitus, elevated blood pressure, increased lipid and cholesterol levels, atherosclerotic diseases and metabolic syndrome
   comprising administering, to a patient in need thereof, a therapeutically effective amount of an optically active compound according to formula (I):

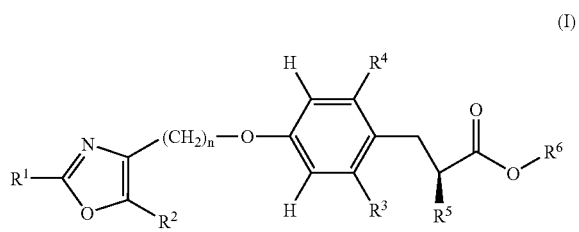

wherein:
(a) R$^1$ is aryl;
(b) R$^2$ is selected from the group consisting of lower-alkyl and fluoro-lower-alkyl;
(c) R$^3$ and R$^4$ independently from each other are selected from the group consisting of hydrogen, hydroxy, halogen, lower-alkyl, fluoro-lower-alkyl, hydroxy-lower-alkyl, lower-alkoxy-lower-alkyl, lower-alkoxy, fluoro-lower-alkoxy, hydroxy-lower-alkoxy, lower-alkoxy-lower-alkoxy, and lower-alkenyl; wherein at least one of $R^3$ and $R^4$ is not hydrogen;

(d) $R^5$ is selected from the group consisting of lower-alkoxy, fluoro-lower-alkoxy, lower-alkenyloxy, fluoro-lower-alkenyloxy, aryloxy, aryl-lower-alkoxy, and aryl-fluoro-lower-alkoxy;

(e) $R^6$ is selected from the group consisting of hydrogen and lower-alkyl; and (f) n is 1;

or pharmaceutically acceptable salts and/or pharmaceutically acceptable esters thereof.

2. The method according to claim 1, wherein the disease is non-insulin dependent diabetes mellitus.

3. The method according to claim 1, wherein $R^1$ is phenyl optionally substituted with 1 to 3 substituents independently selected from the group consisting of lower-alkyl, lower-alkoxy, halogen, and fluoro-lower-alkyl.

4. The method according to claim 1, wherein $R^1$ is selected from the group consisting of phenyl, 2-methyl-phenyl, 4-isopropoxy-phenyl, 4-fluoro-3-methyl-phenyl, 2-fluoro-phenyl, 4-isopropyl-phenyl, 2-ethoxy-4-fluoro-phenyl, 3-methoxy-phenyl, and 4-tert-butyl-phenyl.

5. The method according to claim 1, wherein $R^2$ is lower-alkyl.

6. The method according to claim 1, wherein $R^2$ is methyl.

7. The method according to claim 6, wherein $R^1$ is selected from the group consisting of phenyl, 2-methyl-phenyl, 4-isopropoxy-phenyl, 4-fluoro-3-methyl-phenyl, 2-fluoro-phenyl, 4-isopropyl-phenyl, 2-ethoxy-4-fluoro-phenyl, 3-methoxy-phenyl, or 4-tert-butyl-phenyl.

8. The method according to claim 1, wherein $R^3$ and $R^4$ independently from each other are selected from the group consisting of hydrogen, hydroxy, halogen, lower-alkyl, fluoro-lower-alkyl, and lower-alkoxy; wherein at least one of $R^3$ and $R^4$ is not hydrogen.

9. The method according to claim 1, wherein $R^3$ is hydrogen or methyl.

10. The method according to claim 1, wherein $R^4$ is selected from the group consisting of methyl, ethyl, fluoro, chloro, trifluoromethyl, hydroxy, methoxy, ethoxy, and isopropoxy.

11. The method according to claim 7, wherein $R^4$ is selected from the group consisting of methyl, ethyl, fluoro, chloro, trifluoromethyl, hydroxy, methoxy, ethoxy, and isopropoxy.

12. The method according to claim 11, wherein $R^1$ is selected from the group consisting of phenyl, 2-methyl-phenyl, 4-isopropoxy-phenyl, 4-fluoro-3-methyl-phenyl, 2-fluoro-phenyl, 4-isopropyl-phenyl, 2-ethoxy-4-fluoro-phenyl, 3-methoxy-phenyl, and 4-tert-butyl-phenyl.

13. The method according to claim 12, wherein $R^2$ is methyl.

14. The method according to claim 1, wherein $R^5$ is lower-alkoxy.

15. The method according to claim 1, wherein $R^5$ is methoxy or ethoxy.

16. The method according to claim 15, wherein $R^1$ is selected from the group consisting of phenyl, 2-methyl-phenyl, 4-isopropoxy-phenyl, 4-fluoro-3-methyl-phenyl, 2-fluoro-phenyl, 4-isopropyl-phenyl, 2-ethoxy-4-fluoro-phenyl, 3-methoxy-phenyl, and 4-tert-butyl-phenyl.

17. The method according to claim 16, wherein $R^2$ is methyl.

18. The method according to claim 17, wherein $R^3$ is hydrogen or methyl.

19. The method according to claim 18, wherein $R^4$ is selected from the group consisting of methyl, ethyl, fluoro, chloro, trifluoromethyl, hydroxy, methoxy, ethoxy, and isopropoxy.

20. The method according to claim 1, wherein $R^6$ is hydrogen.

21. The method according to claim 19, wherein $R^6$ is hydrogen.

22. The method according to claim 1, wherein $R^1$ is phenyl substituted with methyl and/or fluorine, $R^2$ is lower-alkyl, $R^3$ is hydrogen, $R^4$ is lower-alkyl, $R^5$ is lower-alkoxy, and $R^6$ is hydrogen.

23. The method according to claim 1, wherein $R^1$ is 2-methyl-phenyl or 2-fluoro-phenyl, $R^2$ is methyl, $R^3$ is hydrogen, $R^4$ is methyl, $R^5$ is ethoxy, and $R^6$ is hydrogen.

24. The method according to claim 1, wherein the compound is selected from the group consisting of:
   (S)-2-Ethoxy-3-[2-methyl-4-(5-methyl-2-o-tolyl-oxazol-4-ylmethoxy)-phenyl]-propionic acid,
   (S)-2-Ethoxy-3-{4-[2-(4-isopropyl-phenyl)-5-methyl-oxazol-4-ylmethoxy]-2-methoxy-phenyl}-propionic acid,
   (S)-2-Ethoxy-3-{4-[2-(4-isopropyl-phenyl)-5-methyl-oxazol-4-ylmethoxy]-2,6-dimethyl-phenyl}-propionic acid,
   (S)-3-{4-[2-(4-tert-Butyl-phenyl)-5-methyl-oxazol-4-ylmethoxy]-2-ethoxy-phenyl}-2-ethoxy-propionic acid, and
   (S)-3-{4-[2-(4-tert-Butyl-phenyl)-5-methyl-oxazol-4-ylmethoxy]-2-isopropoxy-phenyl}-2-ethoxy-propionic acid, or pharmaceutically acceptable salts and/or pharmaceutically acceptable esters thereof.

25. The method according to claim 1, wherein the compound is selected from the group consisting of:
   (S)-2-Ethoxy-3-{4-[2-(4-isopropoxy-phenyl)-5-methyl-oxazol-4-ylmethoxy]-2-methyl-phenyl}-propionic acid, and
   (S)-2-Ethoxy-3-{4-[2-(3-methoxy-phenyl)-oxazol-4-ylmethoxy]-2-methyl-phenyl}-propionic acid, or pharmaceutically acceptable salts and/or pharmaceutically acceptable esters thereof.

26. The method according to claim 1, wherein the compound is selected from the group consisting of:
   (S)-2-Ethoxy-3-[2-methyl-4-(5-methyl-2-phenyl-oxazol-4-ylmethoxy)-phenyl]-propionic acid,
   (S)-2-Ethoxy-3-[2-fluoro-4-(5-methyl-2-phenyl-oxazol-4-ylmethoxy)-phenyl]-propionic acid,
   (S)-3-[2-Chloro-4-(5-methyl-2-phenyl-oxazol-4-ylmethoxy)-phenyl]-2-ethoxy-propionic acid,
   (S)-2-Ethoxy-3-[4-(5-methyl-2-phenyl-oxazol-4-ylmethoxy)-2-trifluoromethyl-phenyl]-propionic acid,
   (S)-3-[2,6-Dimethyl-4-(5-methyl-2-phenyl-oxazol-4-ylmethoxy)-phenyl]-2-ethoxy-propionic acid,
   (S)-3-{2-Hydroxy-4-[2-(5-methyl-2-phenyl-oxazol-4-yl)-ethoxy]-phenyl}-2-methoxy-propionic acid, and
   (S)-2-Ethoxy-3-{2-methyl-4-[3-(5-methyl-2-phenyl-oxazol-4-yl)-propoxy]-phenyl}-propionic acid, or pharmaceutically acceptable salts and/or pharmaceutically acceptable esters thereof.

27. The method according to claim 1, wherein the compound is selected from the group consisting of:
   (S)-2-Ethoxy-3-{4-[2-(4-fluoro-3-methyl-phenyl)-5-methyl-oxazol-4-ylmethoxy]-2-methyl-phenyl}-propionic acid, (S)-2-Ethoxy-3-{2-ethyl-4-[2-(4-fluoro-3-methyl-phenyl)-5-methyl-oxazol-4-ylmethoxy]-phenyl}-propionic acid, and (S)-3-{2-Chloro-4-[2-(4-fluoro-3-methyl-phenyl)-5-methyl-oxazol-4-ylmethoxy]-phenyl}-2-ethoxy-propionic acid, or pharmaceutically acceptable salts and/or pharmaceutically acceptable esters thereof.

28. The method according to claim 1, wherein the compound is selected from the group consisting of:

(S)-2-Ethoxy-3-{4-[2-(2-fluoro-phenyl)-5-methyl-oxazol-4-ylmethoxy]-2-methyl-phenyl}-propionic acid, (S)-3-{2-Chloro-4-[2-(2-fluoro-phenyl)-5-methyl-oxazol-4-ylmethoxy]-phenyl}-2-ethoxy-propionic acid, and (S)-2-Ethoxy-3-(4-{2-[2-(2-ethoxy-4-fluoro-phenyl)-5-methyl-oxazol-4-yl]-ethoxy}-2methyl-phenyl)-propionic acid, or pharmaceutically acceptable salts and/or pharmaceutically acceptable esters thereof.

29. The method according to claim 1, wherein the compound is (S)-2-Ethoxy-3-{4-[2-(2-fluoro-phenyl)-5-methyl-oxazol-4-ylmethoxy]-2-methyl-phenyl}-propionic acid or pharmaceutically acceptable salts and/or pharmaceutically acceptable esters thereof.

30. The method according to claim 1, wherein the compound is (S)-2-Ethoxy-3-{4-[2-(2-fluoro-phenyl)-5-methyl-oxazol-4-ylmethoxy]-2-methyl-phenyl}-propionic acid.

* * * * *